(12) United States Patent
Yamamoto et al.

(10) Patent No.: US 8,152,521 B2
(45) Date of Patent: Apr. 10, 2012

(54) ORTHODONTIC APPLIANCE

(75) Inventors: Teruko Yamamoto, Okayama (JP);
Hiroshi Kamioka, Okayama (JP); Taiji Adachi, Kyoto (JP); Shogo Fukushima, Moriguchi (JP); Takumi Sakimura, Osaka (JP)

(73) Assignee: Panasonic Corporation, Osaka (JP)

( * ) Notice: Subject to any disclaimer, the term of this patent is extended or adjusted under 35 U.S.C. 154(b) by 493 days.

(21) Appl. No.: 11/721,085

(22) PCT Filed: Mar. 23, 2007

(86) PCT No.: PCT/JP2007/056040
§ 371 (c)(1),
(2), (4) Date: Jun. 7, 2007

(87) PCT Pub. No.: WO2007/116654
PCT Pub. Date: Oct. 18, 2007

(65) Prior Publication Data
US 2009/0061379 A1    Mar. 5, 2009

(30) Foreign Application Priority Data

Mar. 28, 2006 (JP) ................. 2006-089431
Mar. 28, 2006 (JP) ................. 2006-089439
Nov. 27, 2006 (JP) ................. 2006-317929
Nov. 27, 2006 (JP) ................. 2006-317930
Nov. 27, 2006 (JP) ................. 2006-317931
Nov. 27, 2006 (JP) ................. 2006-318006
Nov. 27, 2006 (JP) ................. 2006-318376
Nov. 27, 2006 (JP) ................. 2006-318377

(51) Int. Cl.
*A61C 3/00* (2006.01)
(52) U.S. Cl. ......................................... 433/24
(58) Field of Classification Search ................ 433/5–18, 433/24, 213, 215; 29/896.1, 896.11, 527.1; 156/60, 332; 427/2.29; 249/54; 264/16–20; 106/35
See application file for complete search history.

(56) References Cited

U.S. PATENT DOCUMENTS 4,123,844 A * 11/1978 Kurz ................................. 433/5
4,229,165 A    10/1980 Kurz
4,244,688 A    1/1981 Kurz
(Continued)

FOREIGN PATENT DOCUMENTS

DE        4020647        1/1992
(Continued)

OTHER PUBLICATIONS

English language Abstract of JP 2005-342072 A, Dec. 15, 2005.
(Continued)

*Primary Examiner* — Todd Manahan
*Assistant Examiner* — Matthew Nelson
(74) *Attorney, Agent, or Firm* — Greenblum & Bernstein P.L.C.

(57) ABSTRACT

The present invention concerns an orthodontic appliance for accelerating the tooth aligning effect and shortening the treatment period, and has an object to provide an appliance which can bring about higher aligning effect than usual ways by giving vibration to tooth to be aligned to activate bone remodeling of the targeted tooth and the alveolar bone and enhance the shift of the tooth. This appliance includes a vibrating element and a dental mouthpiece having the vibrating element built therein. The provision of the vibrating element in the dental mouthpiece facilitates the application of vibration and handling, and continues the treatment safely even at home. The inner shape of the dental mouthpiece serves aligning treatment as well as acceleration of the effect.

27 Claims, 44 Drawing Sheets

U.S. PATENT DOCUMENTS

| | | | |
|---|---|---|---|
| 4,348,177 A | | 9/1982 | Kurz |
| 4,348,178 A | * | 9/1982 | Kurz .................................. 433/6 |
| 4,382,780 A | | 5/1983 | Kurz |
| 4,484,895 A | * | 11/1984 | Smiley et al. .................. 433/215 |
| 4,511,330 A | * | 4/1985 | Smiley et al. .................... 433/18 |
| 4,676,752 A | * | 6/1987 | Lefkowitz ...................... 433/229 |
| 5,334,015 A | | 8/1994 | Blechman |
| 5,496,256 A | * | 3/1996 | Bock et al. .......................... 601/2 |
| 5,967,784 A | | 10/1999 | Powers |
| 5,975,893 A | | 11/1999 | Chishiti et al. |
| 6,077,075 A | * | 6/2000 | Bedard et al. ................. 433/167 |
| 6,183,248 B1 | | 2/2001 | Chishiti et al. |
| 6,210,162 B1 | | 4/2001 | Chishiti et al. |
| 6,217,325 B1 | | 4/2001 | Chishiti et al. |
| 6,227,850 B1 | | 5/2001 | Chishiti et al. |
| 6,227,851 B1 | | 5/2001 | Chishiti et al. |
| 6,299,440 B1 | | 10/2001 | Phan et al. |
| 6,309,215 B1 | | 10/2001 | Phan et al. |
| 6,371,759 B1 | * | 4/2002 | Schwartz ........................... 433/6 |
| 6,390,812 B1 | | 5/2002 | Chishiti et al. |
| 6,471,511 B1 | | 10/2002 | Chishiti et al. |
| 6,524,101 B1 | | 2/2003 | Phan et al. |
| 6,613,001 B1 | | 9/2003 | Dworkin |
| 6,633,747 B1 | | 10/2003 | Reiss |
| 7,163,399 B2 | | 1/2007 | Kajimoto et al. |
| 2002/0051951 A1 | | 5/2002 | Chishiti et al. |
| 2003/0207224 A1 | * | 11/2003 | Lotte ................................. 433/6 |
| 2004/0013993 A1 | | 1/2004 | Ito |
| 2004/0058295 A1 | | 3/2004 | Bergersen |
| 2004/0063073 A1 | | 4/2004 | Kajimoto et al. |
| 2004/0115587 A1 | | 6/2004 | Breining et al. |
| 2004/0157192 A1 | * | 8/2004 | Jacobs et al. ............... 433/217.1 |
| 2005/0048433 A1 | | 3/2005 | Hilliard |
| 2005/0186524 A1 | * | 8/2005 | Abolfathi et al. .................. 433/7 |
| 2005/0244768 A1 | | 11/2005 | Taub et al. |
| 2005/0266370 A1 | | 12/2005 | Suzuki |
| 2006/0115785 A1 | | 6/2006 | Li et al. |
| 2007/0065768 A1 | | 3/2007 | Nadav |
| 2008/0227046 A1 | | 9/2008 | Lowe et al. |
| 2008/0233541 A1 | * | 9/2008 | De Vreese et al. ............. 433/216 |
| 2008/0254405 A1 | * | 10/2008 | Montgomery et al. ......... 433/29 |
| 2008/0293007 A1 | | 11/2008 | Li et al. |

FOREIGN PATENT DOCUMENTS

| | | |
|---|---|---|
| DE | 19844628 | 4/2000 |
| JP | 57-173052 A | 10/1982 |
| JP | 4-46585 | 7/1992 |
| JP | 6-047064 U | 6/1994 |
| JP | 11-155273 | 6/1999 |
| JP | 2001-340412 | 12/2001 |
| JP | 2002-102255 | 4/2002 |
| JP | 2003-290250 | 10/2003 |
| JP | 2004-113625 | 4/2004 |
| JP | 2004-201895 | 7/2004 |
| JP | 2005-342072 A | 12/2005 |
| WO | 00/19928 | 4/2000 |
| WO | 02/073185 | 9/2002 |
| WO | 2005/092234 A1 | 10/2005 |
| WO | 2006/060547 | 6/2006 |

OTHER PUBLICATIONS

English language Abstract of JP2002-102255.
English language Abstract of JP2004-201895.
English language Abstract of JP2003-290250.
English language Abstract of JP2001-340412.
English language Abstract of JP 2004-113625.
English language Abstract of JP 11-155273.
Shimizu, "A study of the movement of the lateral incisor of the macaca fuscata loaded by a vibrating force," Journal of Japan Orthodontic Society, 45, pp. 56-72, 1986 (including an English language Abstract).
Ohmae et al., "Biomechanical acceleration of experimental tooth movement by ultrasonic vibration in vivo: Part 1, Homo-directional application of ultrasonication to orthodontic force," Journal of Japan Orthodontic Society, Orthod. Wave, 60(4), pp. 201-212, 2001 (including an English language Abstract).
Chiba et al., "Effects of Mechanical stimulation using resonance vibration on the periodontium" (including an English language Abstract).
Emata, "The mechanical response of the periodontal structure in the maxillary lateral incisor of the macaca fuscata yakui, loading by a vibrating force," Japanese Journal of Oral Bial., 21:571-585, 1979 (including an English language Abstract).
U.S. Appl. No. 11/721,086 to Yamamoto et al., filed Jun. 7, 2007.
U.S. Appl. No. 11/721,129 to Yamamoto et al., filed Jun. 7, 2007.
U.S. Appl. No. 11/813,375 to Yamamoto et al., filed Jul. 5, 2007.
China Office action, dated Jan. 27, 2011 along with an english language partial translation.

* cited by examiner 0.1s 0.1s  0.2s

ORTHODONTIC APPLIANCE

TECHNICAL FIELD

The present invention relates to an orthodontic appliance.

BACKGROUND ART

An orthodontic appliance equipped with an orthodontic wire to be mounted on teeth has been conventionally known. An elastic restoring force of the orthodontic wire acts as a constant static load on the teeth to correct teeth malalignment or crossbite. In other words, the orthodontic appliance is based on the principle of aligning the teeth by gradually deforming an alveolar bone supporting the teeth through the application of a constant force to the teeth, or bone remodeling.

However, the teeth alignment using the orthodontic wire takes a very long time (fastest six months, normally several years) until an orthodontic treatment is finished. This is likely to become a cause to give up the treatment easily.

In order to shorten a period of such an orthodontic treatment, technology of giving a vibration force to the teeth has been studied. For example, a study result to the effect that if a sample A in which a constant force was applied to the teeth and a sample B in which a vibration force was applied to the teeth are compared, the sample B to which the vibration force was applied is more effective in shortening the period as shown in FIG. 17A is disclosed in non-Patent Literature 1.

Similarly, a study result to the effect that if a sample C in which a constant force was applied to the teeth and a sample D in which a constant force and a vibration force were applied to the teeth are compared, the sample D to which the constant force and vibration force were applied is more effective in shortening the period as shown in FIG. 17B is disclosed in non-Patent Literature 2.

According to these studies, the application of the vibration force to the teeth remarkably shortens the period of orthodontic treatment to about ½ to ⅓ as compared to conventional technologies. Further, it is sufficient to apply a vibration force only for 1.5 hours a day according to the former Literature and only for 2 minutes at a time and once every two weeks according to the latter Literature.

It can be understood from these studies that the teeth alignment by applying a vibration force as well as a constant force to the teeth is more effective in remarkably shortening the period of orthodontic treatment than the teeth alignment only by applying a constant force to the teeth using an orthodontic wire or the like.

Appliances for putting the above studies to practical use have been conventionally proposed. Specifically, Patent Literature 1 discloses an appliance provided with a dental mouthpiece to be mounted on the teeth to urge movements of teeth to be aligned and means for applying ultrasonic vibration to tissues surrounding the mounted position of the dental mouthpiece. Further, Patent Literature 2 discloses an appliance for applying ultrasonic vibration to teeth to be aligned.

However, the appliances disclosed in the above Patent Literatures 1, 2 have a problem that ultrasonic vibration cannot be efficiently applied to the teeth to be aligned since both of them receive the application of ultrasonic vibration from the outside, for example, by pressing an ultrasonic head against the cheek skin. Further, since the respective appliances require an ultrasonic generator, there is also a problem that treatment cannot be continued unless a patient goes to a dental clinic equipped with these appliances.

[Non-Patent Literature 1] Shimizu: "Journal of Japan Orthodontic Society" 45, pp. 56-72, 1986
[Non-Patent Literature 2] Ohmae et al.: "Journal of Japan Orthodontic Society" 60(4), p. 201, 2001
[Patent Literature 1] Japanese Unexamined Patent Publication No. 2002-102255
[Patent Literature 2] Japanese Unexamined Patent Publication No. 2004-201895

DISCLOSURE OF THE INVENTION

The present invention has been worked out to solve the above problems, and has an object to provide an orthodontic appliance which can precisely apply vibration to tooth to be aligned and enables a treatment to be easily and safely continued even at home.

In order to accomplish the object, the present invention is directed to an orthodontic appliance for aligning teeth including a tooth to be aligned, comprising a vibrating element for generating mechanical vibration and applying the vibration to the tooth to be aligned; and a dental mouthpiece having the vibrating element built therein and mountable on the teeth with the vibrating element built therein.

Since the vibrating element for generating the mechanical vibration (mechanical stimuli) is built in the dental mouthpiece to be mounted on the teeth in this appliance, the vibrating element can efficiently apply the vibration to the tooth to be aligned. Further, the storage of the vibrating element in the dental mouthpiece enables a treatment to be easily and safely continued at any desired time, for example, at home without going to a dental clinic to apply mechanical vibration.

BRIEF DESCRIPTION OF THE DRAWINGS

FIGS. 7A and 7B show a dental mouthpiece according to a third embodiment of the invention, wherein FIG. 7A is an exploded perspective view and FIG. 7B is a section along the line VIIB-VIIB in FIG. 7A.

FIGS. 9A and 9B show a dental mouthpiece according to a fourth embodiment of the invention, wherein FIG. 9A is a perspective view and FIG. 9B is a section along the line IXB-IXB in FIG. 9A.

BEST MODES FOR EMBODYING THE INVENTION

Hereinafter, best modes for embodying the present invention are described in detail with reference to the accompanying drawings.

Figure 1:
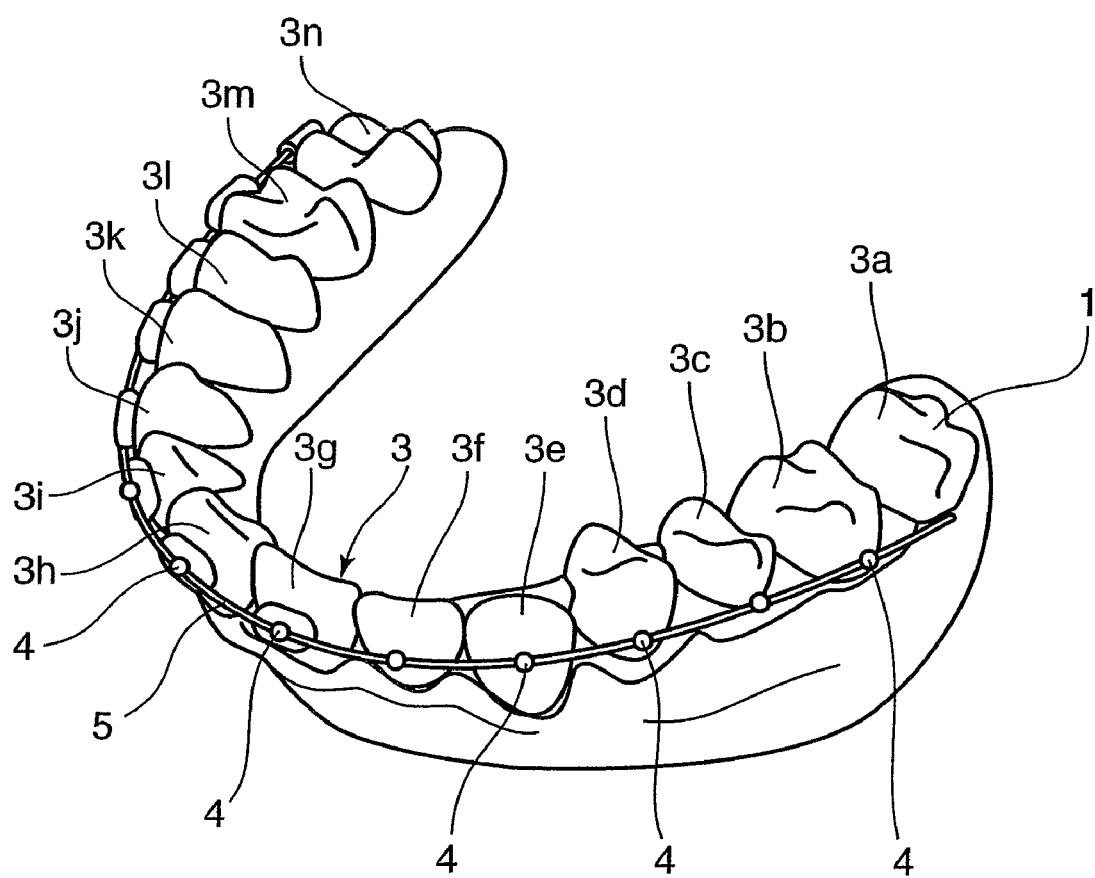
FIG. 1 is a perspective view of a dental cast of a lower dental arch.

A first embodiment of the present invention is described with reference to FIGS. 1 to 5. FIG. 1 is a perspective view of a dental cast 1 of a lower dental arch according to this embodiment, and FIG. 2 is a perspective view showing a state where a dental mouthpiece 7 according to this embodiment is mounted on teeth 3 of the dental cast 1.

The teeth 3 shown in FIG. 1 are comprised of teeth 3a to 3n, wherein the teeth 3a, 3n are posterior teeth. Braces are mounted on the teeth 3b to 3m excluding these posterior teeth. These braces include a plurality of brackets 4 to be fixed to the buccal surfaces of the teeth 3b to 3m and an orthodontic wire (arch wire) 5 arranged to connect these brackets 4. This orthodontic wire 5 is latched to the teeth 3b to 3m by the respective brackets 4. The orthodontic wire 5 is elastically deformably latched, so that an elastic restoring force thereof acts as a constant static load on the teeth 3. The application of this static load corrects malocclusion. It should be noted that braces for aligning the dentition are not limited to the one shown in FIG. 1.

Figure 2:
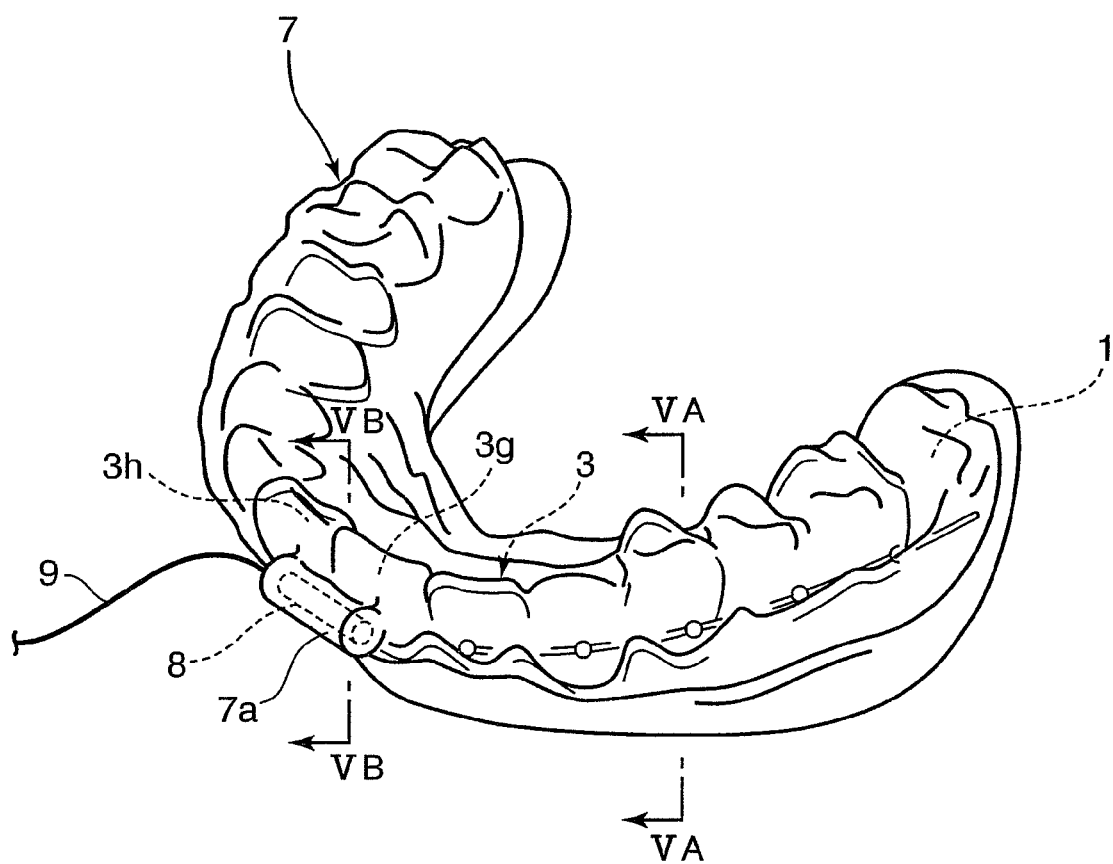
FIG. 2 is a perspective view showing a state where a dental mouthpiece according to a first embodiment of the invention is mounted on teeth.
Figure 3:
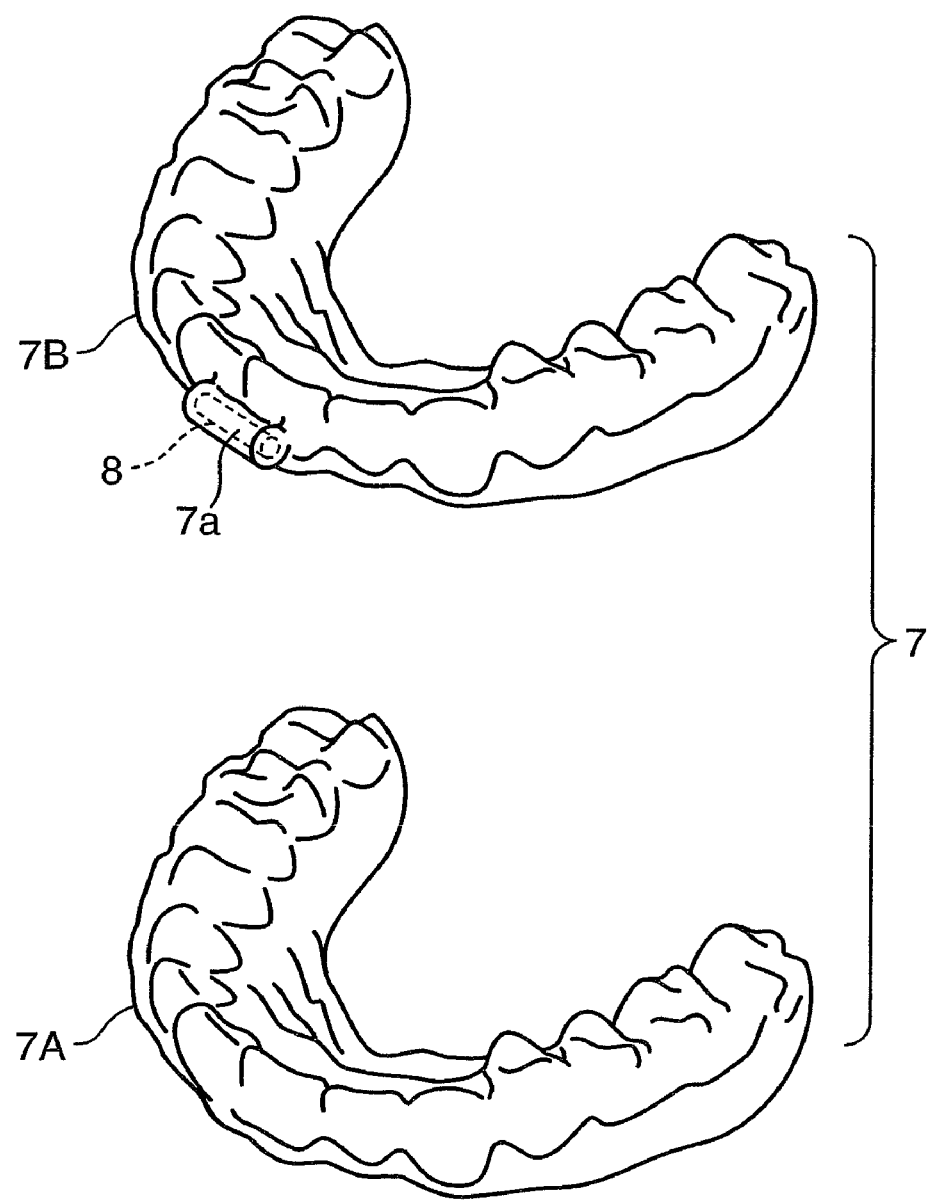
FIG. 3 is an exploded perspective view showing the dental mouthpiece of FIG. 2 when viewed from topside.

An orthodontic appliance according to this embodiment is provided with an electric motor 8 and a dental mouthpiece 7 as shown in FIGS. 2 and 3.

Figure 4:
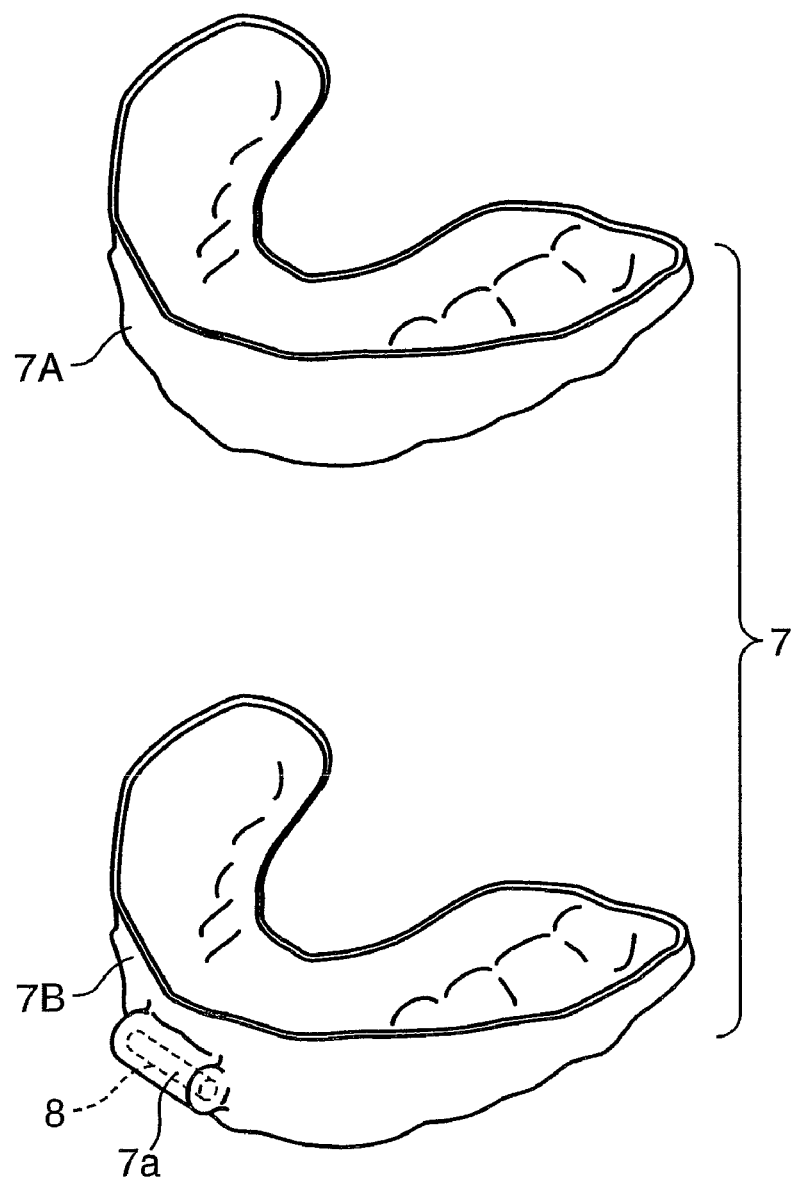
FIG. 4 is an exploded perspective view showing the dental mouthpiece of FIG. 2 from underside.

The dental mouthpiece 7 is mounted on teeth to be aligned, e.g. the teeth 3 having the orthodontic wire 5 mounted thereon. FIG. 3 is an exploded perspective view of the dental mouthpiece 7 when viewed from topside, and FIG. 4 is an exploded perspective view of the dental mouthpiece 7 when viewed from underside.

Figure 5A:
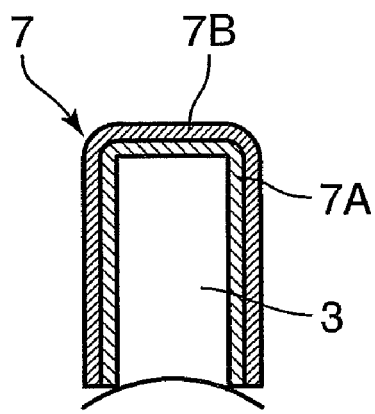
FIG. 5A is a section along the line VA-VA in FIG. 2.

The dental mouthpiece 7 has an inner and outer overlaid structure. Specifically, the dental mouthpiece 7 is comprised of an inner layer 7A to be directly mounted on the teeth 3 and an outer layer 7B mounted on the outer side of the inner layer 7A as shown in FIG. 5A.

The inner and outer layers 7A, 7B are preferably cast into suitable shapes using a material normally used for ordinary mouthpieces and having guaranteed hygienic safety, e.g. an EVA (ethylene vinyl acetate) sheet which is a polymer material (method for producing the dental mouthpiece 7 is described later). Such a material is preferable since having little influence such as side effects on teeth and gingival tissues.

The material of the dental mouthpiece according to the present invention is not limited to the EVA sheet. However, the EVA sheet is preferable because it has a high electrically insulating property and functions as a heat insulating material. Particularly, the application of the EVA sheet to the inner layer 7A can make the inner layer 7A softer. The soft inner layer 7A can alleviate the transmission of mechanical vibration (particularly high-speed components) from the electric motor 8 to be described later to the teeth 3g, 3h to be aligned. The alleviation of transmission of such vibration effectively suppresses damages of the teeth 3g, 3h to be aligned.

Figure 5B:
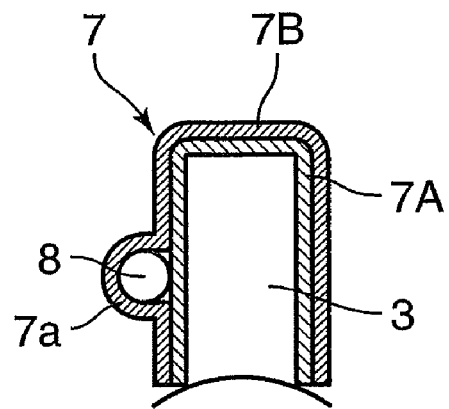
FIG. 5B is a section along the line VB-VB in FIG. 2

The electric motor 8 constitutes a vibrating element for generating mechanical vibration and is built in the dental mouthpiece 7. Since the electric motor 8 is built in, a bulge portion 7a as shown in FIG. 5B is formed at a part of the outer layer 7B corresponding to the teeth 3g, 3h to be aligned. A clearance for storing the electric motor 8 is defined between the inner surface of the bulge portion 7a and the outer surface of the inner layer 7A.

The electric motor 8 is small-sized and lightweight and generates vibration to accelerate the orthodontic alignment effect. The electric motor 8 is horizontally stored in the above clearance (i.e. in such a posture that the direction of the vibration is substantially normal to the teeth 3). This electric motor 8 has an eccentric rotary portion which is rotatable about a specified axis and whose center of gravity is deviated from this axis, wherein the rotation of the eccentric rotary portion induces mechanical vibration. The above rotary portion may, for example, be comprised of a rotary shaft and an eccentric weight mounted at a position deviated from the central axis of this rotary shaft. An electric motor generally used as a vibrator for a mobile phone or the like can be used as the electric motor 8.

The inner layer 7A is mounted inside the outer layer 7B with the electric motor 8 stored in the bulge portion 7a. Further, the outer surface of the inner layer 7A and the inner surface of the outer layer 7B are joined airtight, for example, by thermal welding or ultrasonic welding so that saliva, cleaning liquid or the like does not enter the bulge portion 7a through the interfaces, and these pieces 7A, 7B are united by this joining. The airtightness is sufficient if the inside of the bulge portion 7a is held watertight to such an extent that moisture does not actually enter.

Figure 5C:
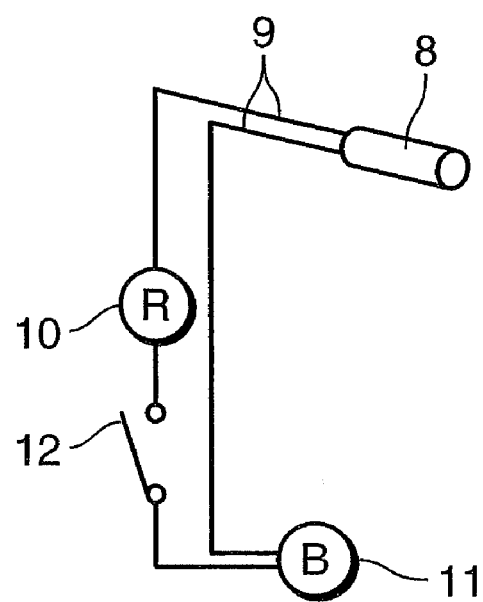
FIG. 5C is a connection diagram of an electric motor.

In this embodiment, the electric motor 8 is a direct-current (DC) motor. This orthodontic appliance includes a battery 11 as shown in FIGS. 2 and 5C as a direct-current source for the electric motor 8, and the electric motor 8 is connected with this battery 11 via a feeder cable 9. The feeder cable 9 is drawn out of the dental mouthpiece 7 from the electric motor 8 through a though hole 7f formed in the bulge portion 7a while holding the inside of the bulge portion 7a of the outer layer 7B airtight, and further drawn out of the mouth between the lips to be connected with the battery 11 via a variable resistor 10 and a switch 12.

The variable resistor 10 and the battery 11 are, for example, placed on a desk or the like near a user (patient) wearing the dental mouthpiece 7. The variable resistor 10 changes a DC current level to be supplied to the electric motor 8. The adjustment of the DC current level by this variable resistor 10 enables the adjustment of the rotating speed of the electric motor 8, i.e. the adjustment of frequency. A vibration frequency (frequency) to be adjusted is not specifically limited, but is preferably about several Hz to several hundreds Hz, for example. An alternating-current (AC) motor may be used as the electric motor 8.

Next, one example of the method for producing the dental mouthpiece 7 is described with reference to FIG. 12.

Figure 12:
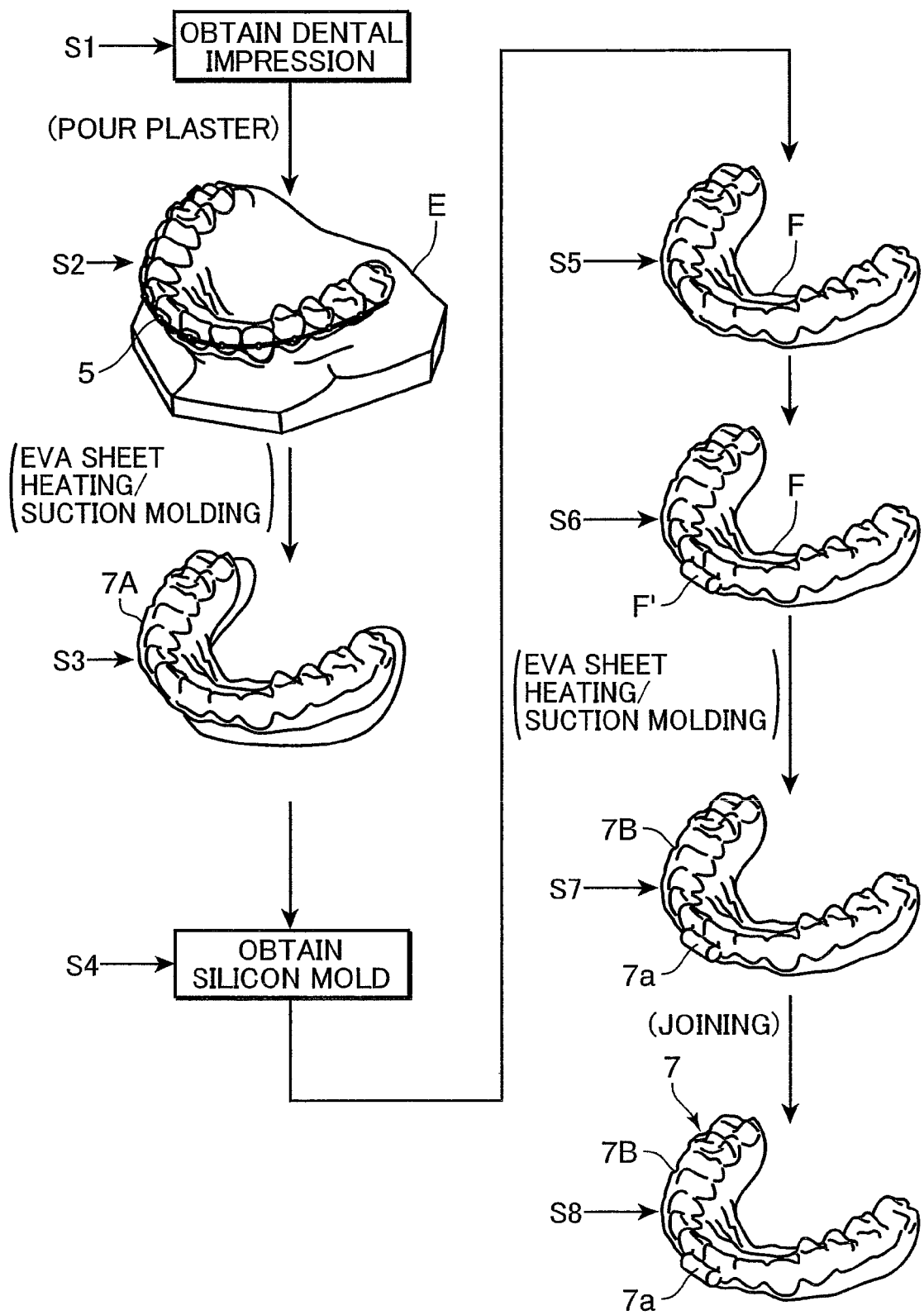
FIG. 12 is a diagram showing the process of producing a dental mouthpiece according to the present invention.

In Step S1 shown in FIG. 12, a dental impression is obtained by attaching an impression material to teeth 3 of a user. After obtaining the dental impression, the tray with impression material is taken out from the teeth 3 while keeping the teeth shape, and plaster is poured into this impression material. This plaster is taken out from the impression material after being hardened. In this way, a plaster model of dentition E for the user is completed (Step S2).

If the braces including the brackets 4 and the orthodontic wire 5 are mounted on the teeth 3 of the user, the inner layer 7A might be broken or the brackets 4 might be disengaged from the teeth by the inner layer 7A getting caught by edges of the braces upon mounting the inner layer 7A of the dental mouthpiece 7 on the teeth 3. In order to prevent such problems, wax or the like can be filled into clearances in parts of the dental cast E corresponding to the brackets 4 and the orthodontic wire 5 to eliminate the edges. This method reduces burdens on the user as compared to a method according to which dental impression is carried out after nontoxic wax or the like that can be washed away with water is filled into clearances of the brackets 4 and the orthodontic wire 5 before the impression material is attached to the teeth 3.

An EVA sheet softened by heating is placed on the teeth plaster model E of Step S2, and suction casting is applied. After this EVA sheet is cooled, the inner layer 7A is completed by taking the teeth plaster model E from the EVA sheet (Step S3).

Inner layers having different thicknesses can be fabricated by changing the thickness of the EVA sheet. The use of the thin inner layer 7A improves wearing comfort and improves the transmission characteristic of mechanical vibration from the electric motor 8. It is also possible to change the transmission characteristic of mechanical vibration to the individual teeth 3a to 3n by changing the thickness of the inner layer 7A for each tooth 3a to 3n.

The inner layer 7A is fitted to the teeth plaster model E (Step S3), and a dental impression is performed anew using silicon resin or the like in this state (Step S4). Plaster is poured into the completed silicon cast, and is taken out after being hardened. In this way, an inner layer plaster model F is completed (Step S5).

A plaster model F' that becomes the bulge portion 7a of the outer layer 7B is adhered to the inner layer plaster model F (Step S6). Further, an EVA sheet softened by heating is placed on the inner layer plaster model F, and suction casting is applied. After this EVA sheet is cooled, the outer layer 7B is completed by taking the inner layer plaster model F from the EVA sheet (Step S7).

Thereafter, the inner layer 7A is fitted inside the outer layer 7B with the electric motor 8 stored in the bulge portion 7a of the outer layer 7B. In this state, the outer surface of the inner layer 7A and the inner surface of the outer layer 7B are joined airtight by means of ultrasonic welding or adhesive to be united, whereby the dental mouthpiece 7 is completed (Step S8). The total thickness of the dental mouthpiece 7 is preferably about 1 to 6 mm.

The outer surface of the inner layer 7A and the inner surface of the outer layer 7B may be joined only at the peripheral edge portion of the bulge portion 7a of the outer layer 7B storing the electric motor 8. However, in light of cleaning and storage of the inner layer 7A and the outer layer 7B, and also cleaning and storage of the dental mouthpiece 7 after the use of it, it is preferable to join the entire outer peripheral edges of the inner layer 7A and the outer layer 7B airtight.

Since the electric motor 8 for generating mechanical vibration (mechanical stimuli) is built in the dental mouthpiece 7 to be mounted on the teeth 3 in the orthodontic appliance according to this embodiment, vibration can be efficiently applied to the teeth 3g, 3h to be aligned. Particularly, since the electric motor 8 according to this embodiment is stored in the part of the dental mouthpiece 7 corresponding to the teeth 3g, 3h to be aligned, vibration can be precisely applied to the teeth 3g, 3h to be aligned.

Further, the storage of the electric motor 8 in the dental mouthpiece 7 enables the treatment to be easily and safely continued at any desired time, for example, at home even without going to a dental clinic.

Furthermore, since the mechanical vibration of the electric motor 8 is transmitted to the teeth 3g, 3h to be aligned via the inner layer 7A, pains to the teeth resulting from the direct transmission of mechanical vibration to the teeth 3g, 3h to be aligned can be mitigated.

Further, the sealed storage of the electric motor 8 in the dental mouthpiece 7 is hygienic and enables water-washing.

The electric motor 8 as the vibrating element is inexpensive. Particularly, the electric motor for generating mechanical vibration by the rotation of the eccentric rotary portion is more inexpensive since a small-sized and lightweight electric motor generally used as the one provided with a vibrator function can be used as it is.

In the case where the electric motor 8 generates mechanical vibration by the rotation of the eccentric rotary portion, the direction of the rotary shaft of the electric motor 8 and the direction of the teeth coincide with each other if the electric motor 8 is stored in the dental mouthpiece 7 such that the vibrating direction is substantially normal to the teeth 3. The coincidence of these directions reduces uncomfortable feeling by reducing the projecting height from the dental mouthpiece 7 even if the electric motor 8 is long along the rotary shaft thereof. Further, since the vibrating direction of the electric motor 8 is normal to the teeth, the vibration of the electric motor 8 can be imparted to the teeth efficiently.

If the electric motor 8 is driven by a direct-current (DC) power source, the frequency (rotating speed) of the electric motor 8 can be easily adjusted through the adjustment of a direct-current voltage level by the variable resistor 10. Further, the use of the battery 11 as the direct-current power source enables a treatment in such a place where there is no AC outlet (e.g. outdoors).

Since the dental mouthpiece 7 is so shaped as to be mountable on the entire teeth 3, the electric motor 8 as the vibrating element for generating mechanical vibration can be precisely positioned at the teeth 3g, 3h by mounting the dental mouthpiece 7 on the teeth 3.

If the electric motor 8 is held in direct contact with the inner surface of the bulge portion 7a or the like, a vibration force outputted by the electric motor 8 is likely to be restrained. Therefore, the electric motor 8 is preferably accommodated in a cover made of metal or resin (e.g. ABS resin) so that the vibration force is not restrained, and stored into the clearance in the bulge portion 7a together with the cover in this state.

Figure 13A:
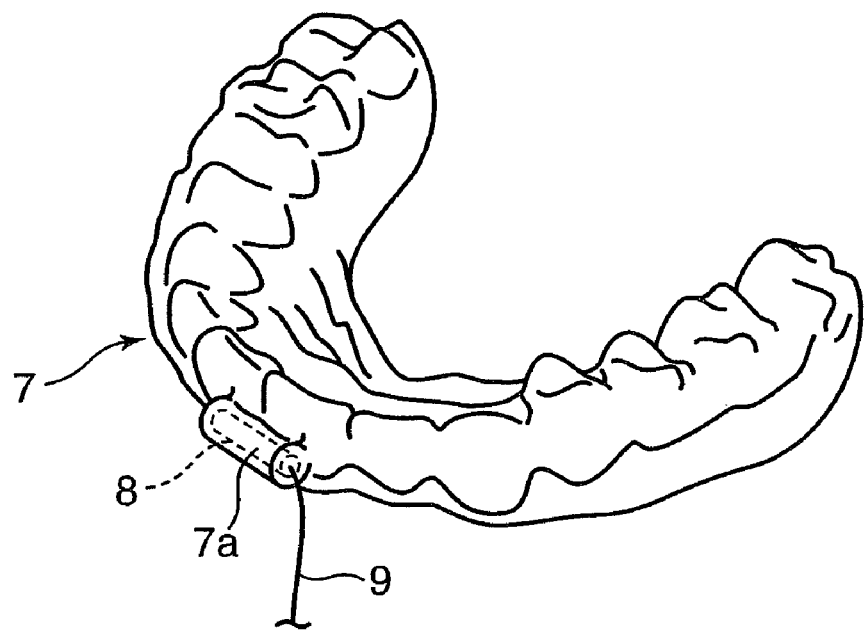
FIG. 13A is a perspective view of a dental mouthpiece according to a seventh embodiment of the invention.
Figure 13B:
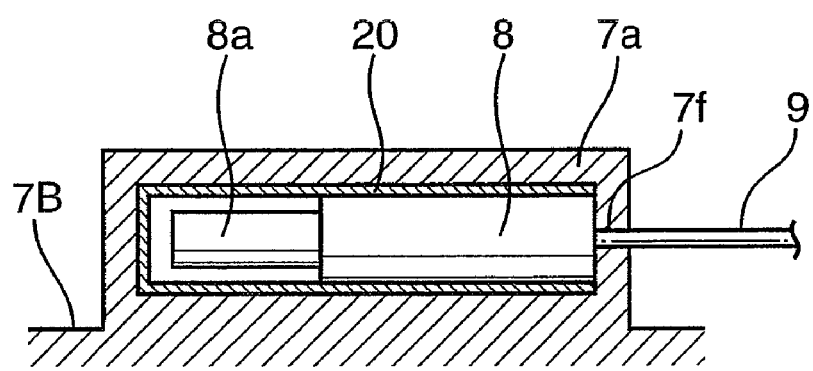
FIG. 13B is an enlarged section showing an essential portion.

For example, as shown as a seventh embodiment in FIGS. 13A and 13B, a cover 20 made of metal or resin and having a cylindrical shape with a closed top may be fitted on the casing of the electric motor 8 to enclose the eccentric weight 8a of the electric motor 8, and the electric motor 8 may be stored into the clearance in the bulge portion 7a together with the cover 20 in this state.

Figure 14A:
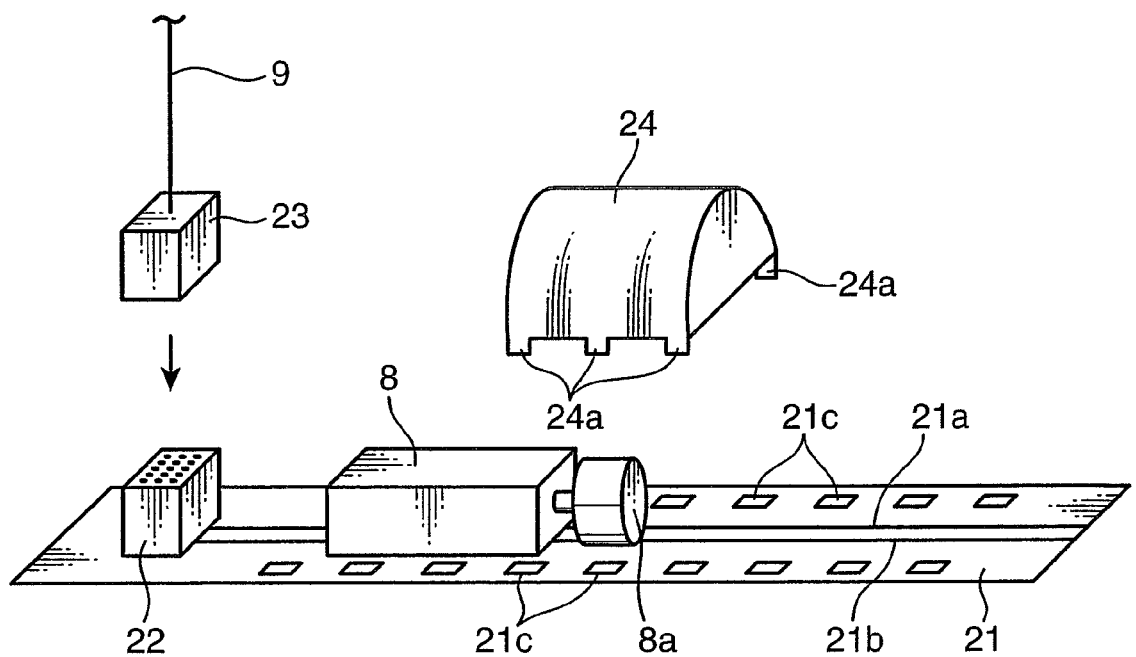
FIG. 14A is a perspective view of an electric motor portion of a dental mouthpiece according an eighth embodiment of the invention.
Figure 14B:
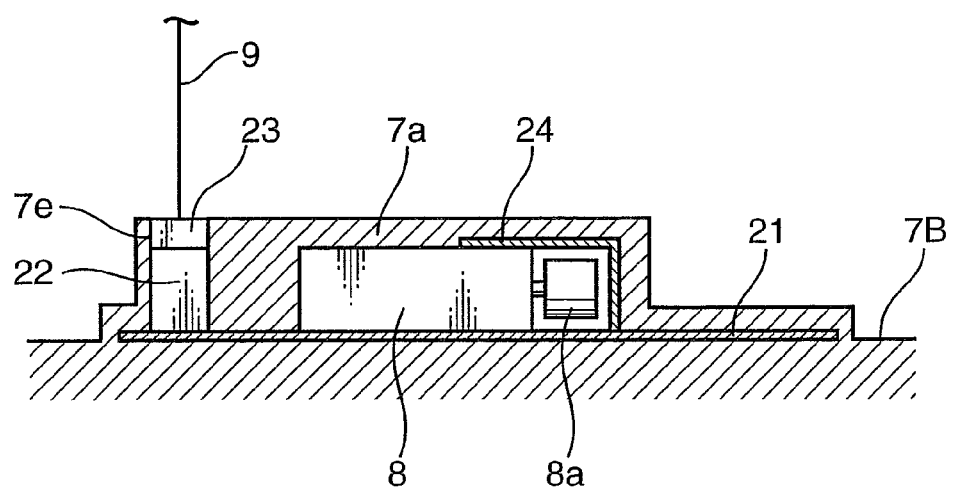
FIG. 14B is an enlarged section showing an essential portion.

Alternatively, the electric motor 8 may be mounted on a rectangular flexible printed board 21 as shown as an eighth embodiment in FIGS. 14A, 14B. A pair of power supply conductors 21a, 21b extending in lengthwise direction are formed on the flexible printed board 21. Power feed terminals (not shown) that can respectively come into contact with the conductors 21a, 21b are formed on the underside of the electric motor 8, and the mount position of the electric motor 8 on the flexible printed board 21 is adjustable in a direction along the conductors 21a, 21b. The electric motor 8 is fixed to the flexible printed board 21 by soldering the power feed terminals of the electric motor 8 and the conductors 21a, 21b to each other after the mount position is adjusted. Further, power feed terminals (not shown) of one connector (e.g. male connector) 22 can be soldered to the conductors 21a, 21b of the flexible printed board 21.

A cover 24 made of metal or resin and having a semicylindrical shape with a closed top is mounted around the casing of the electric motor 8. This cover 24 includes a plurality of claws 24a, and the flexible printed board 21 is formed with a plurality of locking holes 21c along the conductors 21a, 21b. The claws 24a are engaged with suitable ones of the locking holes 21c at positions where the cover 20 encloses the eccentric weight 8a of the electric motor 8, and the electric motor 8 is stored together with the cover 24 into the clearance inside the bulge portion 7a in this engaged state.

The dental mouthpiece 7 is formed with a covering portion 7e continuous with the bulge portion 7a and adapted to cover the one connector 22 airtight, and another connector (e.g. female connector) 23 is detachably connected with the connector 22 in the covering portion 7e in an orthogonal direction. When being connected with the one connector 22, the other connector 23 is also covered airtight by the covering portion 7e. To the other connector 23 is coupled a power feed cable 9, which is drawn out of the connector 23 to the outside while keeping the airtight state and is pulled out of the mouth between the lips.

The power feed cable 9 of the electric motor 8 shown in FIGS. 13A and 13B is also drawn out to the outside through the through hole 7f formed in the bulge portion 7a of the outer layer 7B while keeping the airtight state. This part of the dental mouthpiece 7 where the cable 9 is drawn out is preferably completely waterproofed since the dental mouthpiece 7 is fully water-washable. An exemplary structure for this purpose is shown in FIG. 15.

Figure 15A:
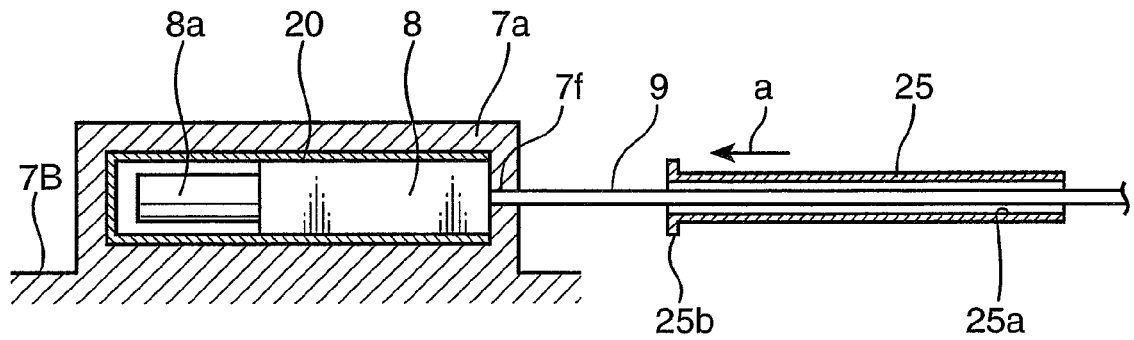
FIG. 15A is a section showing a state at the time of inserting a tube in a tube connecting structure utilizing the dental mouthpiece according to the seventh embodiment of the invention.

A tube 25 as shown in FIG. 15A is used in this structure. This tube 25 has an insertion hole 25a formed in its central part through which the power feed cable 9 is inserted, and a flange 25b is formed at the leading end of the tube 25. This tube 25 is optimally made of the same material as the dental mouthpiece 7, i.e. EVA (ethylene vinyl acetate). The use of EVA enables excellent unification. The tube 25 preferably has such a length as to be sufficiently drawn out of the mouth between the lips.

Figure 15B:
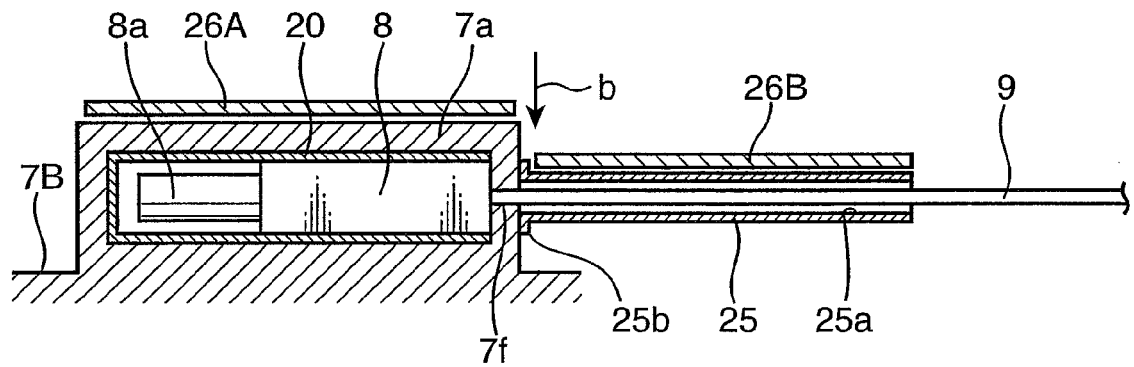
FIG. 15B is a section showing a state at the time of welding the tube.
Figure 15C:
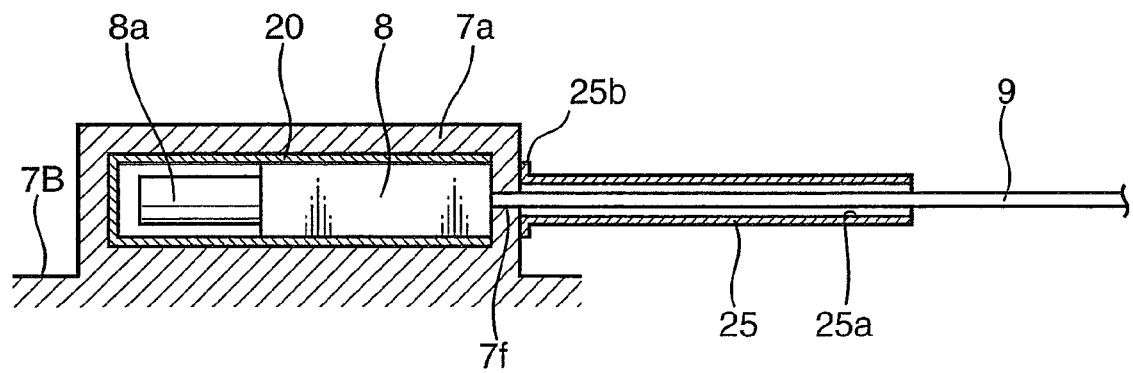
FIG. 15C is a section after the tube is welded.

The power feed cable 9 is inserted into the insertion hole 25a from the side of the flange 25b, and the flange 25b is pressed into close contact with the side surface of the bulge portion 7a as shown in FIG. 15B. The outer surface of the bulge portion 7a and that of the tube 25 are covered by heat insulating materials 26A, 26B in this close contact state. With only a part near the flange 25b exposed, the flange 25b is welded to adhere airtight to the side surface of the bulge portion 7*a* as shown in FIG. 15C. The welding can be accomplished by the above-mentioned thermal welding, ultrasonic welding or the like.

The structure obtained in this way can better improve the watertightness of the part of the dental mouthpiece 7 where the power feed cable 9 is drawn out to enable the accomplishment of complete watertightness as compared to the case where the power feed cable 9 is merely drawn out to the outside through the through hole 7*f* of the bulge portion 7*a* of the outer layer 7B. Further, since the covering of the power feed cable 9 by the tube 25 made of EVA hinders the contact of the power feed cable 9 with the buccal cavity, hygienic safety can be guaranteed even if the power feed cable 9 is, for example, made of vinyl chloride. The appearance can also be improved.

The power feed cable 9 of the other connector 23 shown in FIGS. 14A and 14B is also drawn out to the outside from the connector 23 in an airtight manner. This drawn-out part is also preferably completely waterproofed since the dental mouthpiece 7 is fully water-washable. An exemplary structure for this purpose is shown in FIG. 16.

Figure 16A:
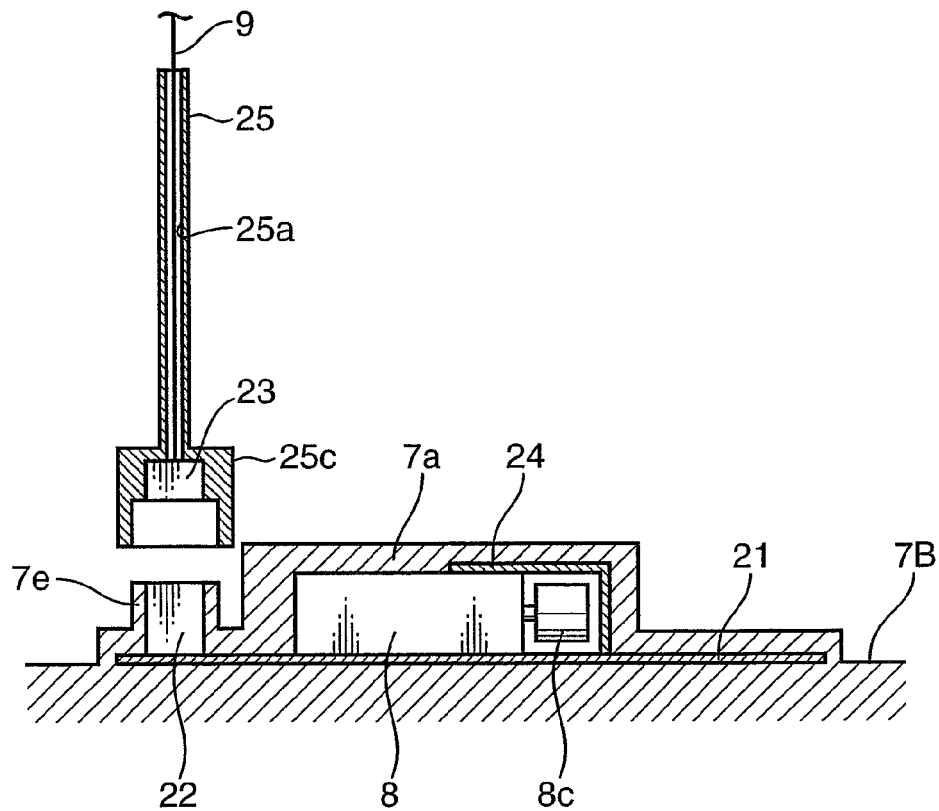
FIG. 16A is a section before connecting a connector in a tube connecting structure utilizing the dental mouthpiece of the eighth embodiment of the invention.
Figure 16B:
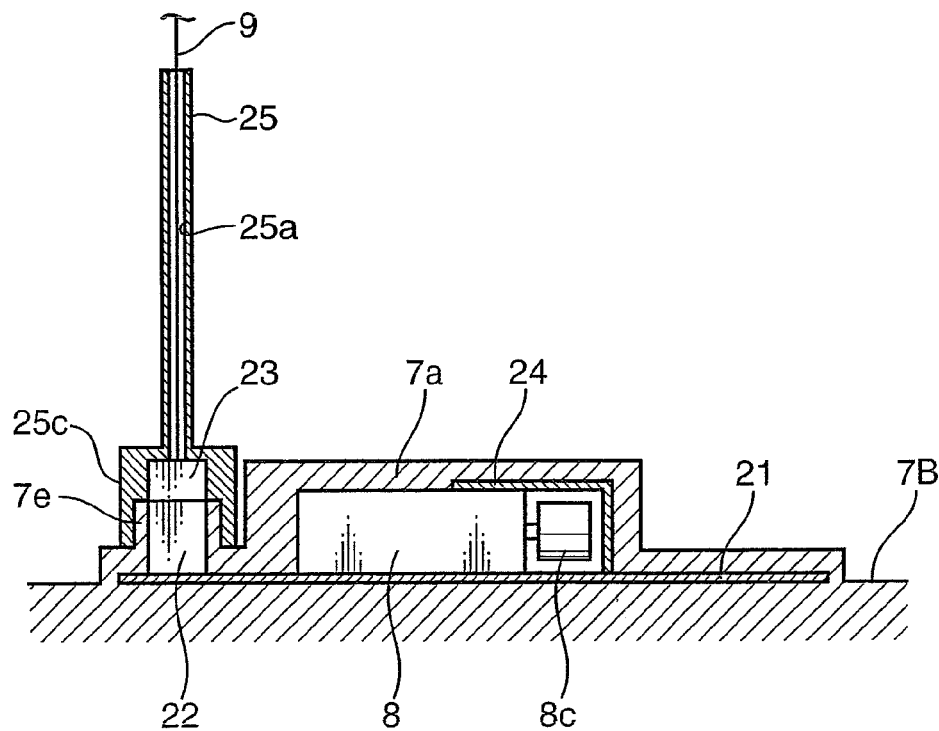
FIG. 16B is a section after the connector is coupled.
Figure 17A:
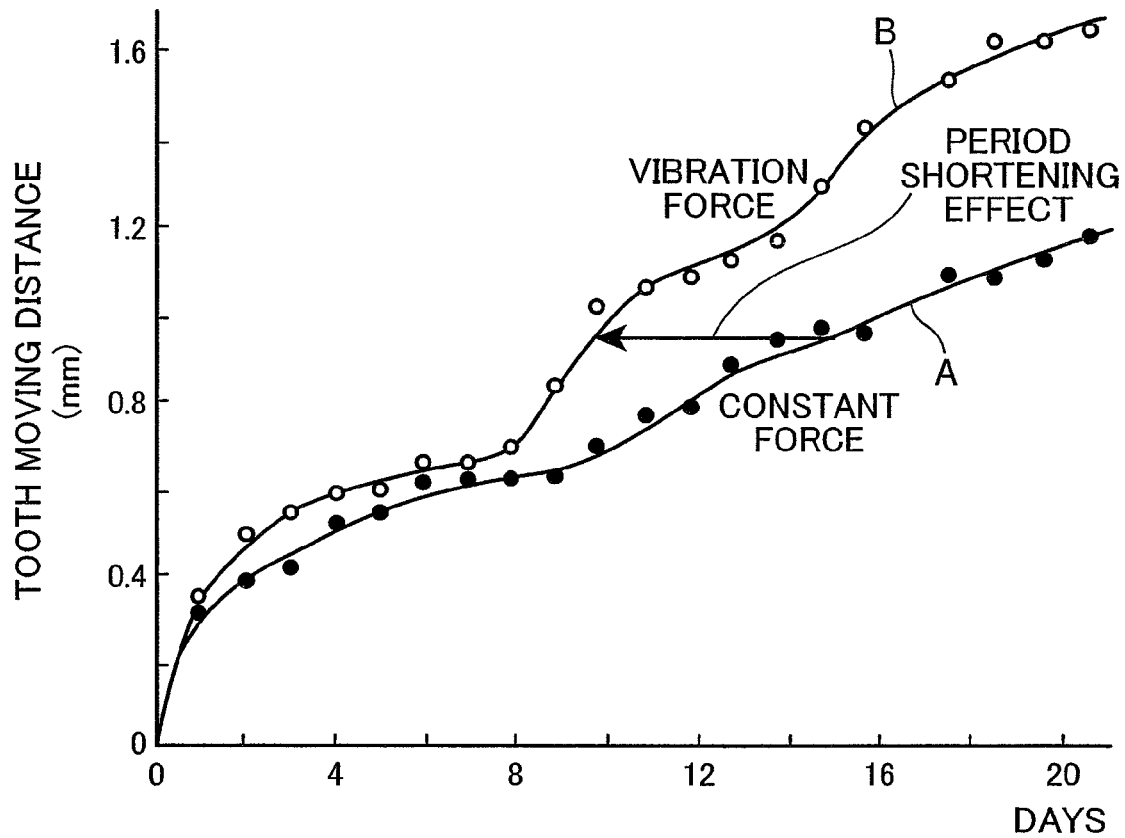
FIGS. 17A and 17B are graphs respectively showing an effect of shortening a period of orthodontic treatment.
Figure 17B:
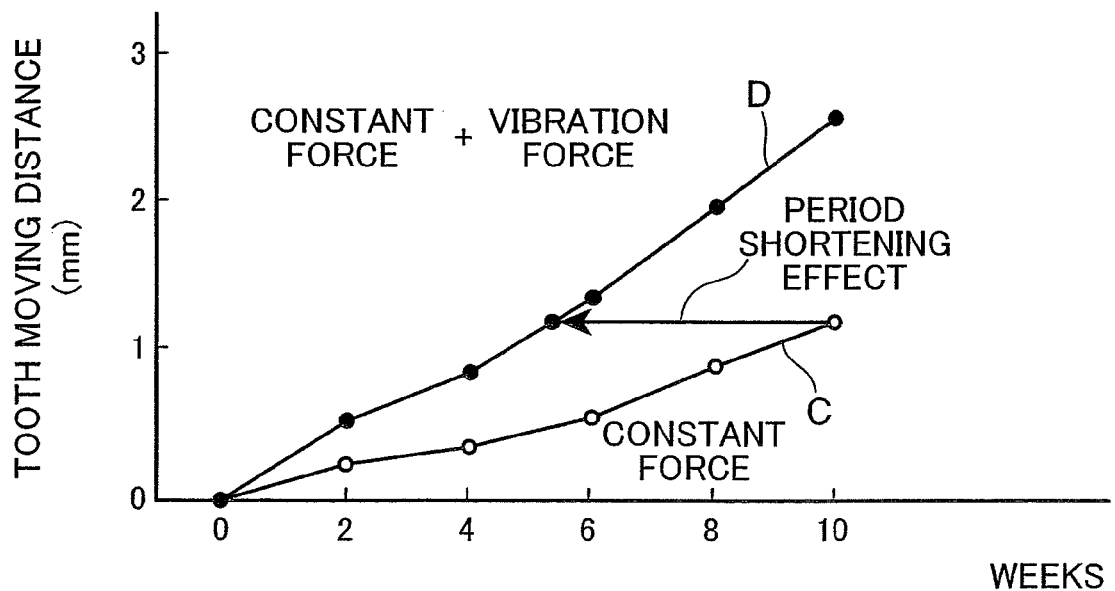

A tube 25 as shown in FIG. 16A is used in this structure. This tube 25 also has an insertion hole 25*a* formed in its central part through which the power feed cable 9 is inserted, and a tubular portion 25*c* is formed at the leading end of the tube 25. This tubular portion 25*c* covers the other connector 23 and projects further forward. This tube 25 is optimally made of the same material as the dental mouthpiece 7, i.e. EVA (ethylene vinyl acetate). The tube 25 preferably has such a length as to be sufficiently drawn out of the mouth between the lips.

The covering portion 7*e* continuous with the bulge portion 7*a* has such a tubular shape fittable inside the tubular portion 25*c* of the tube 25 in an airtight manner. The other connector 23 is detachably connectable with the connector 22 in the covering portion 7*e* from the outside in an orthogonal direction with the covering portion 7*e* fitted inside the tubular portion 25*c*.

This structure can better improve the watertightness of the part of the dental mouthpiece 7 where the power feed cable 9 is drawn out to enable the accomplishment of complete watertightness as compared to the case where the power feed cable 9 is merely drawn out to the outside from the other connector 23. Further, since the covering of the power feed cable 9 by the tube 25 made of EVA hinders the contact of the power feed cable 9 with the buccal cavity, hygienic safety can be guaranteed even if the power feed cable 9 is, for example, made of vinyl chloride. The appearance can also be improved.

It should be noted that an embodiment using a flexible board is described in detail as a twentieth embodiment later.

Figure 6:
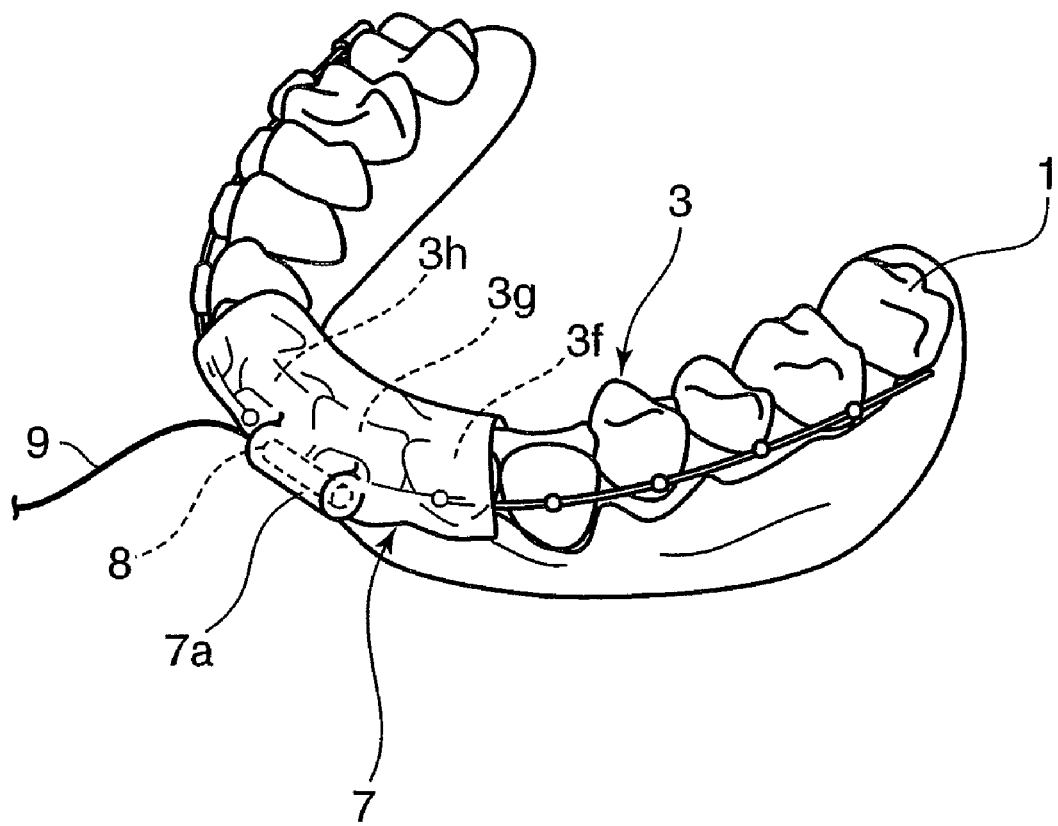
FIG. 6 is a perspective view showing a state where a dental mouthpiece according to a second embodiment of the invention is mounted on teeth.

As shown as a second embodiment in FIG. 6, the dental mouthpiece 7 may be so shaped as to be mountable on a part (teeth 3*f* to 3*h* to be aligned in the example of FIG. 6) of the teeth 3. The dental mouthpiece 7 having such a shape is small in size and reduces burdens on the user at the time of wearing the dental mouthpiece 7.

The dental mouthpiece 7 is normally also mounted on an alveolar portion of the dental cast 1. However, part of the dental mouthpiece 7 corresponding to the alveolar portion may be cut off in order to apply mechanical vibration only to the teeth 3. Such cutting reduces the mass of the dental mouthpiece 7, facilitates the vibration transmission and makes the dental mouthpiece 7 smaller.

Since the dental mouthpiece 7 of this embodiment is mounted on the entire teeth 3, it is comprised of the inner layer 7A to be directly mounted on the teeth 3 and the outer layer 7B to be mounted on the inner layer 7A. However, the inner layer 7A may be in the form of a rectangular piece as shown as a third embodiment in FIGS. 7A and 7B. This inner layer 7A in the form of a rectangular piece is united with the outer layer 7B by being joined airtight with the inner side of the outer layer 7B having the electric motor 8 stored in the bulge portion 7*a* in such a manner as to cover an opening of the bulge portion 7*a*. In this appliance, the outer layer 7B is directly mounted on the teeth 3 and the inner layer 7A functions as a mere sealing member to be joined with the outer layer 7B airtight.

Conversely, a recess for storing the vibrating element may be formed at a part of the inner layer 7A to be mounted on the teeth 3 and the outer layer 7B may be locally joined with the inner layer 7A in such a manner as to cover the vibrating element fitted into the recess from the outer side.

It is also possible to store a drive power source, a controller and the like for the electric motor 8 together with the electric motor 8 as the vibrating element in the dental mouthpiece 7 having the inner and outer overlaid structure. Such storage eliminates the need to draw the power feed cable from the dental mouthpiece 7 out of the mouth between the lips and connect it with an external device (battery, controller or the like).

Figure 9A:
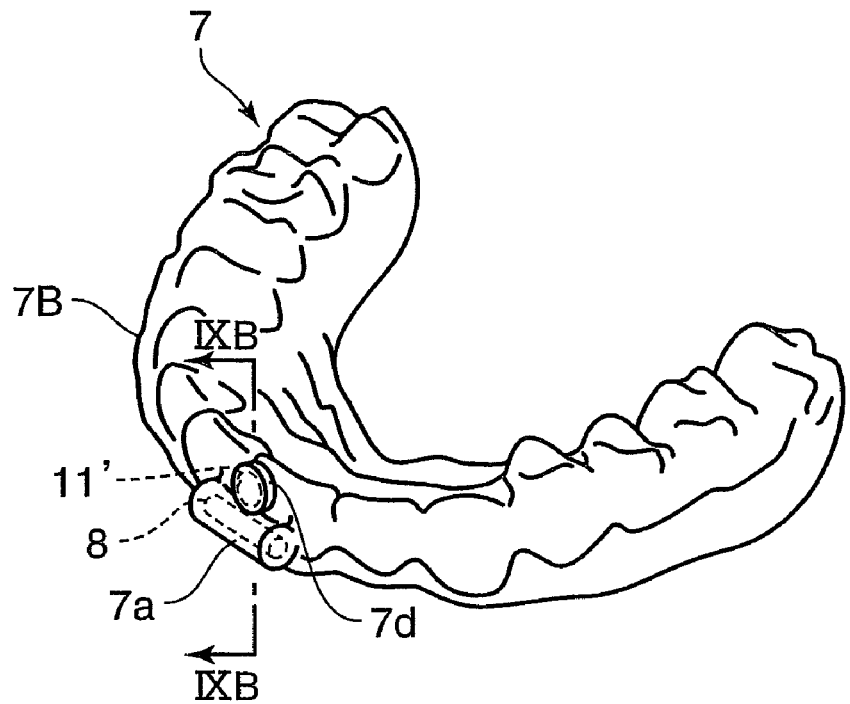
Figure 9B:
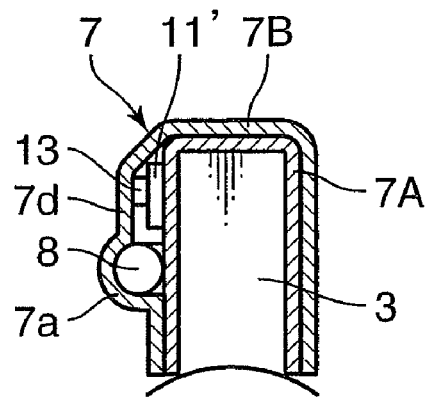

For example, in an appliance shown as a fourth embodiment in FIGS. 9A and 9B, a small-sized button battery 11' is used as a power source for the electric motor 8. An outer layer 7B is additionally formed with a bulge portion 7*d* for storing the button battery 11' in the vicinity of the bulge portion 7*a* for storing the electric motor 8. The electric motor 8 and the button battery 11' can be directly connected with each other by a power feed cable or the like in both bulge portions 7*a*, 7*d*. A switch 13 that is alternately turned on and off every time being pushed from the outer surface of the outer layer 7B can be incorporated into the power feed cable or the like.

The electric motor (vibrating element) 8, the button battery 11', the switch 13 and the like stored in the dental mouthpiece 7 are preferably insulated from each other. An ordinary insulation process may be applied for this insulation or the insulating property of the material of the dental mouthpiece 7 itself may be utilized, i.e. the dental mouthpiece 7 may be partially used as insulation walls.

It is also possible to store a flexible board forming a control unit in the dental mouthpiece 7. By mounting circuit elements such as a vibrating element, a drive power source and a controller therefor on this flexible board, the circuit elements can be more easily built in the dental mouthpiece 7. This mounting enables wiring and coupling with the outside to be omitted, enables the appearance of the appliance to be defined only by the dental mouthpiece, and enables high electrical safety to be ensured by hindering the contact of the power feed cable 9 with the inside of the buccal cavity. An improvement in wearing comfort can also be expected. Further, the practical value of the appliance can be increased by making the appliance portable.

In the foregoing embodiments, the bulge portion 7*a* is formed only at one position (position corresponding to the teeth 3*g*, 3*h* to be aligned) of the outer layer 7B of the dental mouthpiece 7. However, the bulge portions 7*a* may be formed at a plurality of positions (e.g. positions corresponding to the teeth 3*g*, 3*h* to be aligned and the teeth 3*c*, 3*d* to be aligned as shown as a fifth embodiment in FIG. 10) of the outer layer 7B of the dental mouthpiece 7 and the electric motor 8 may be stored in each of these bulge portions 7*a*.

Figure 10:
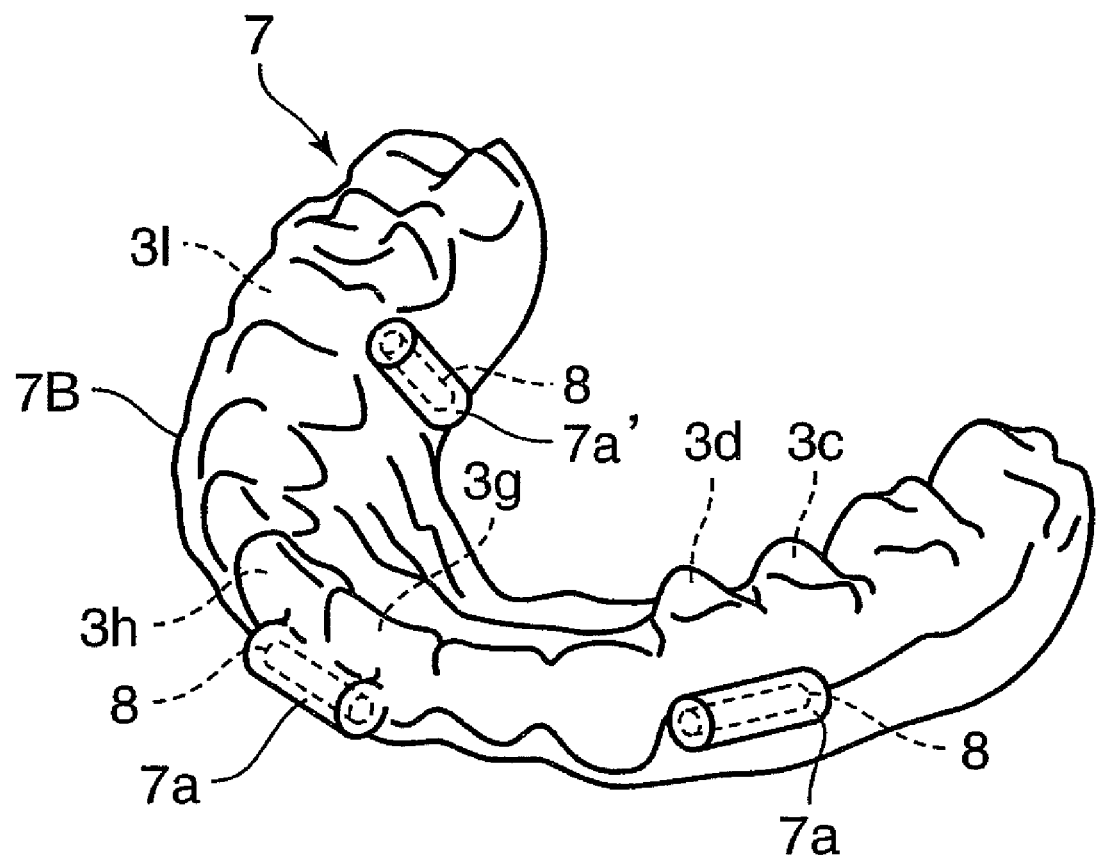
FIG. 10 is a perspective view showing a dental mouthpiece according to a fifth embodiment of the invention.

In the foregoing embodiments, the outward projecting bulge portion 7*a* is formed at the part of the front side of the outer layer 7B corresponding to the teeth 3*g*, 3*h* to be aligned and the electric motor 8 is horizontally stored in this bulge portion 7a. However, an inward projecting bulge portion 7a' may be formed at a part of the rear side of the outer layer 7B corresponding to a tooth 3l to be aligned and the electric motor 8 may be vertically stored in this bulge portion 7a' as shown in FIG. 10.

Although the dental mouthpiece 7 according to the foregoing embodiments has the overlaid structure comprised of the inner layer 7A and the outer layer 7B, the dental mouthpiece according to the present invention may have a multilayer structure comprised of three, four or more layers.

The vibrating element according to the present invention is not limited to the electric motor 8 and may be a linear motor having a moving element that reciprocally vibrates. Besides, a solenoid, a voice coil motor or the like can also be used as such.

Figure 11A:
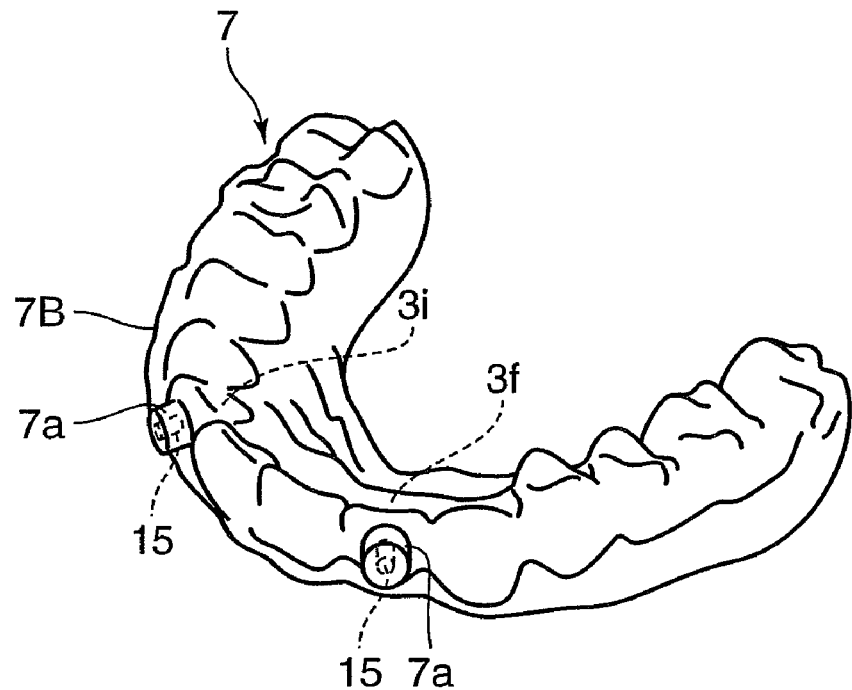
FIG. 11A is a perspective view of a dental mouthpiece according to a sixth embodiment of the invention.

Alternatively, the vibrating element may be a permanent magnet 15 as shown as a sixth embodiment in FIG. 11A. In an appliance shown in FIG. 11A, the bulge portions 7a are respectively formed at positions of the outer layer 7B corresponding to the teeth 3f, 3i to be aligned and the permanent magnet 15 is stored in each of these bulge portions 7a.

Figure 11B:
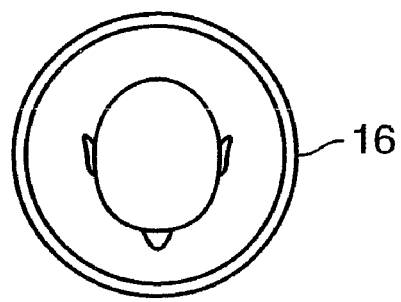
FIG. 11B is a plan view showing a user and a magnetic field generating coil.
Figure 11C:
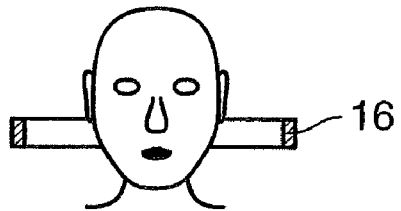
FIG. 11C is a front view showing the user and the magnetic field generating coil.

This permanent magnet 15 can generate mechanical vibration by a magnetic field generated by magnetic field generating means arranged outside the dental mouthpiece 7. This magnetic field generating means is constituted, for example, by a ring-shaped magnetic field generating coil (magnetic field generating means) 16 separate from the dental mouthpiece 7 as shown in FIGS. 11B and 11C. This magnetic field generating coil 16 is arranged around the head of a user wearing the dental mouthpiece 7 while being separated from the user and generates a magnetic field for causing the permanent magnet 15 to generate mechanical vibration.

In this appliance, it is sufficient to build only the permanent magnet 15 in the dental mouthpiece 7. This can reduce the size of the dental mouthpiece 7 and reduce burdens on the user at the time of wearing the dental mouthpiece 7. This also increases the practical value of the dental mouthpiece 7 by making the dental mouthpiece 7 portable.

In the appliances according to the respective embodiments, there is a possibility of transmitting mechanical vibration not only to the teeth to be aligned at the stored position of the vibrating element, but also to the other teeth 3a to 3n of the teeth 3, depending on the built-in position of the vibrating element (electric motor 8 or permanent magnet 15). This enables the treatment of the entire teeth 3a to 3n of the teeth 3.

The dental mouthpiece 7 of the foregoing embodiments is for imparting the vibration force to the constant aligning force by being mounted on the teeth 3 having the orthodontic wire 5 mounted thereon. However, this dental mouthpiece 7 may be mounted on the teeth 3 having no orthodontic wire 5 mounted thereon and transmit only the vibration force by the electric motor 8 to the teeth 3.

It is also possible to shape the dental mouthpiece 7 in such a manner as to apply a constant force (aligning force) to the teeth 3g, 3h to be aligned. Specifically, an instant teeth is elastic-deformedly mounted with a dental mouthpiece having a targeted teeth shape (dental mouthpiece having a shape different from the instant teeth shape) to thereby impart the elastic restoring force of the dental mouthpiece to the instant teeth as an aligning force. In the case where a dental mouthpiece is made from a high resilient and soft material, such dental mouthpiece can be applied with a great elastic deformation. However, in the case where a dental mouthpiece is made from a low resilient and hard material, such dental mouthpiece cannot be applied with a great elastic deformation, in other words, such dental mouthpiece cannot be used for teeth greatly different from the shape of the dental mouthpiece. However, such hard mouthpiece can form a precise shape, and impart a delicate aligning force to the teeth. Accordingly, there are provided a mouthpiece which has a shape in agreement with a targeted teeth shape, and a mouthpiece which has an intermediate shape between an instant teeth shape and a targeted teeth shape.

Figure 8A:
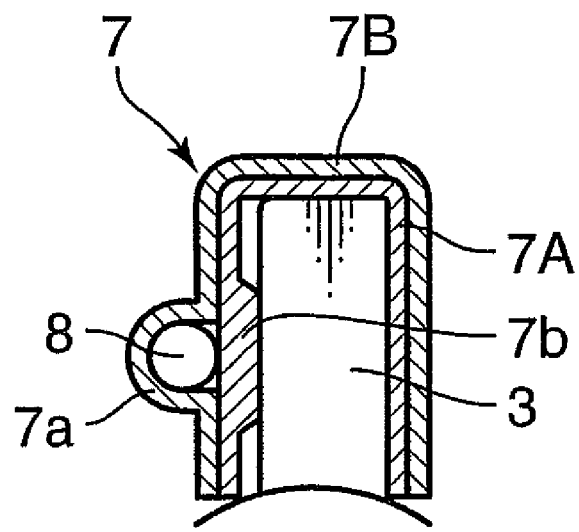
FIGS. 8A and 8B are sections corresponding to the one along the line VIIB-VIIB in FIG. 7A and showing other constructions.
Figure 8B:
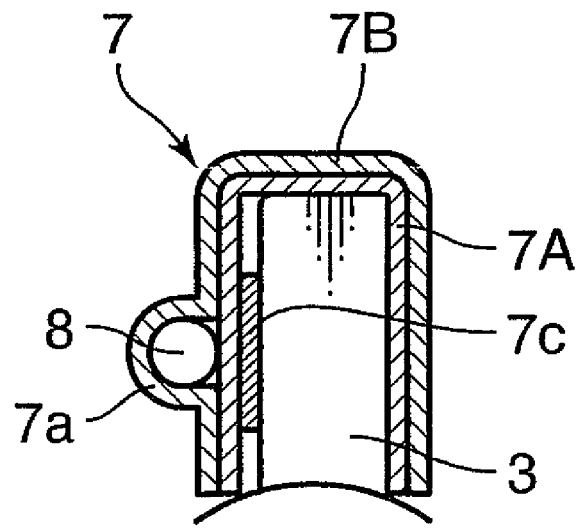

Further, it may be possible to add a desired aligning shape to a main body of a dental mouthpiece. For example, a hard bulging portion 7b is formed on the inner surface of an inner layer 7A in a dental mouthpiece 7 shown in FIG. 8A, and a constant force (aligning force) is applied to the teeth 3g, 3h to be aligned by a pressing force of the bulging portion 7b. It is also possible to join a hard bulging sheet 7c with the inner surface of the inner layer 7A as shown in FIG. 8B and to apply a constant force (aligning force) to the teeth 3g, 3h to be aligned by the pressing force of the bulging sheet 7c. The position of the bulging portion 7b or the bulging sheet 7c differs as a matter of fact if the teeth 3g, 3h to be aligned differ.

Figure 7A:
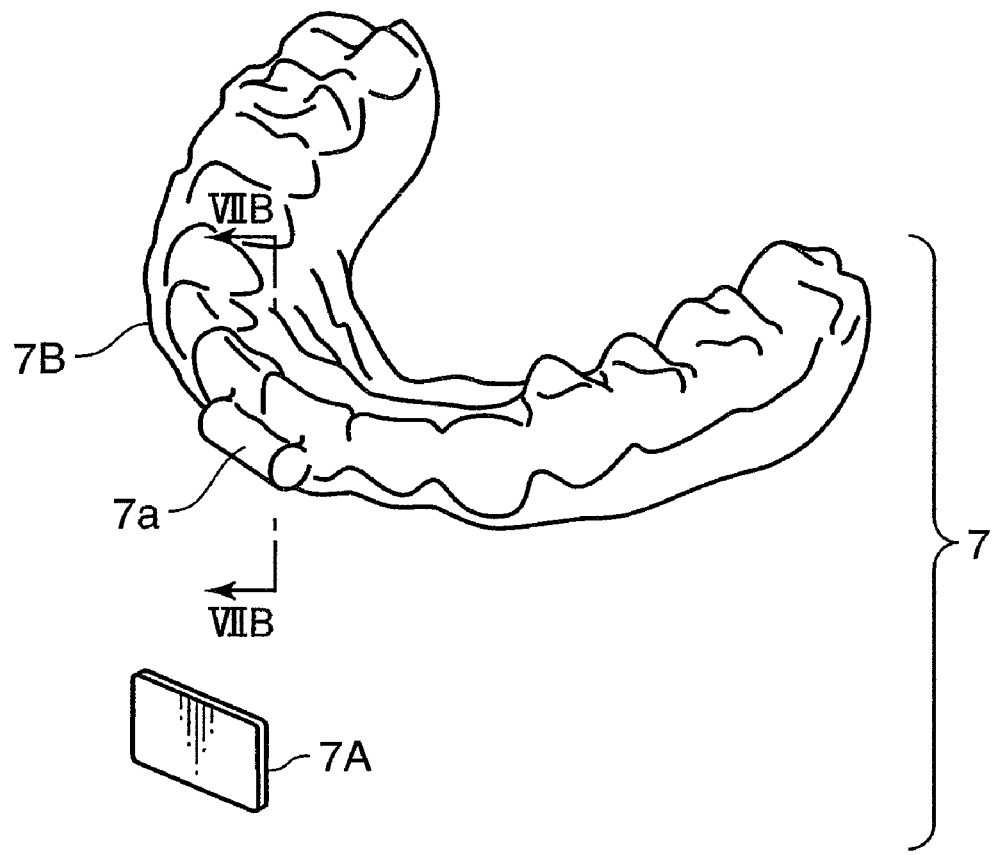
Figure 7B:
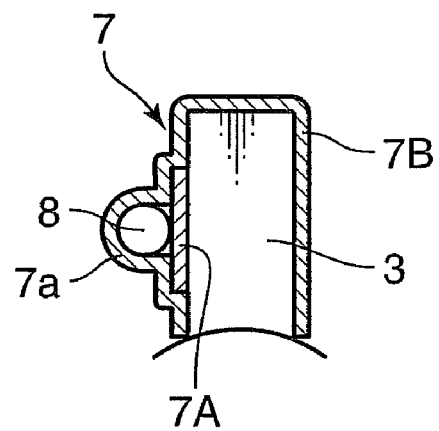

In the appliance whose outer layer 7B is directly mounted on the teeth 3 as shown in FIGS. 7A and 7B, it is possible to integrally form a hard bulging portion on the inner surface of the outer layer 7B or to join a hard bulging sheet with this inner surface. If the inner layer 7A in the form of a rectangular piece shown in FIGS. 7A and 7B is hard itself, the constant force (aligning force) can be applied to the teeth 3g, 3h to be aligned by the pressing force of this inner layer 7A. This structure increases the practical value of the appliance since the constant aligning force and the vibration force can be applied to the teeth 3g, 3h to be aligned without mounting the orthodontic wire 5 on the teeth 3.

Figure 18:
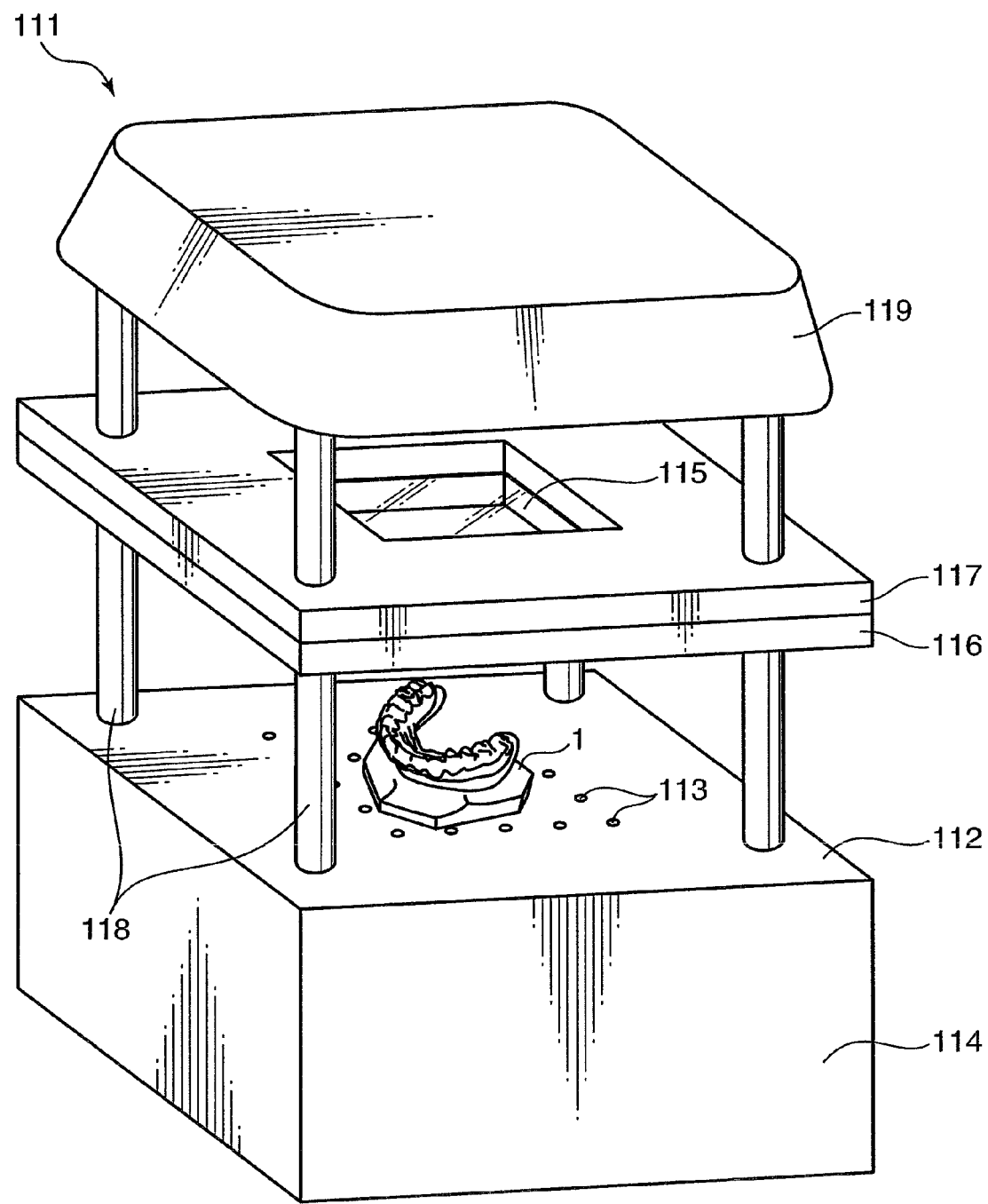
FIG. 18 is a perspective view showing one example of a dental mouthpiece producing apparatus according to the invention.

FIG. 18 is a perspective view showing a producing apparatus 111 as one example of an apparatus for producing the dental mouthpiece 7. This producing apparatus 111 is provided with a main body 114, a plurality of supporting columns 118 standing on the main body 114, a pair of sheet fixing devices 116, 117 supported on these supporting columns 118 in such a manner as to be movable upward and downward along the supporting columns 118 and adapted to sandwich an EVA sheet 115 from above and below, and an electric heater 119 mounted on the supporting columns 118. The main body 114 has a stage 112 on which the dental cast 1 can be placed, and has an unillustrated built-in pump for sucking air through a multitude of suction holes 113 formed in the stage 112.

Figure 19:
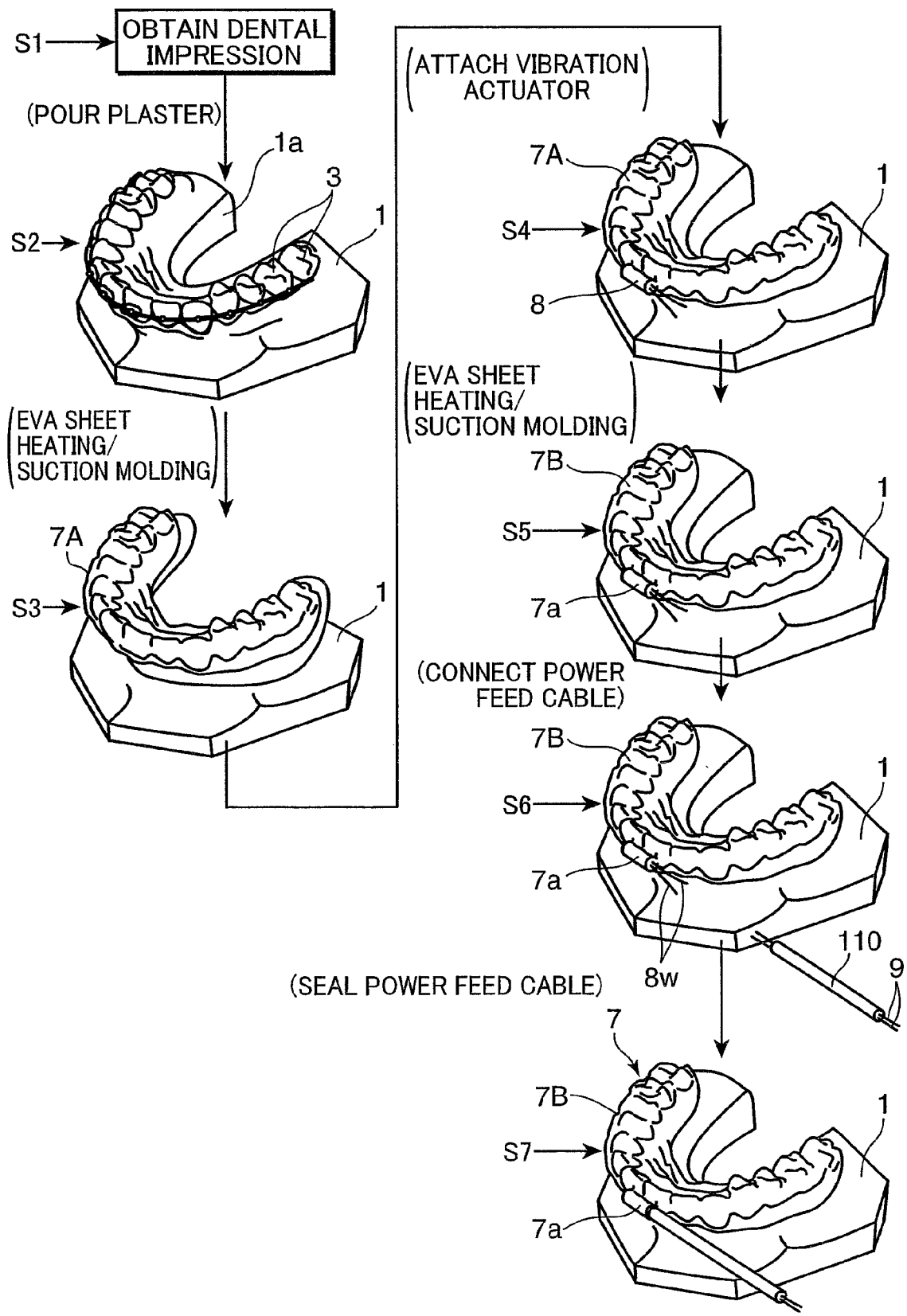
FIG. 19 is a diagram showing a first example of a dental mouthpiece producing method of the invention using the producing apparatus shown in FIG. 18.

FIG. 19 is a diagram showing a first example of a method for producing the dental mouthpiece 7 using the aforementioned producing apparatus 111. What should be first noted here is that the production of the dental mouthpiece 7 proceeds with the inner layer 7A and the outer layer 7B mounted on the dental cast 1. The dental cast 1 is placed on the stage 112 of the producing apparatus 111 in Step S3. On the other hand, the EVA sheet 115 is sandwiched between the sheet fixing devices 116, 117. Specifically, this sheet is heated and softened at a position near the electric heater 119 by the sheet fixing devices 116, 117 being lifted up to this position along the supporting columns 118. After the softening, the EVA sheet 115 is gradually placed on the dental cast 1 as the sheet fixing devices 116, 117 are lowered.

Figure 21A:
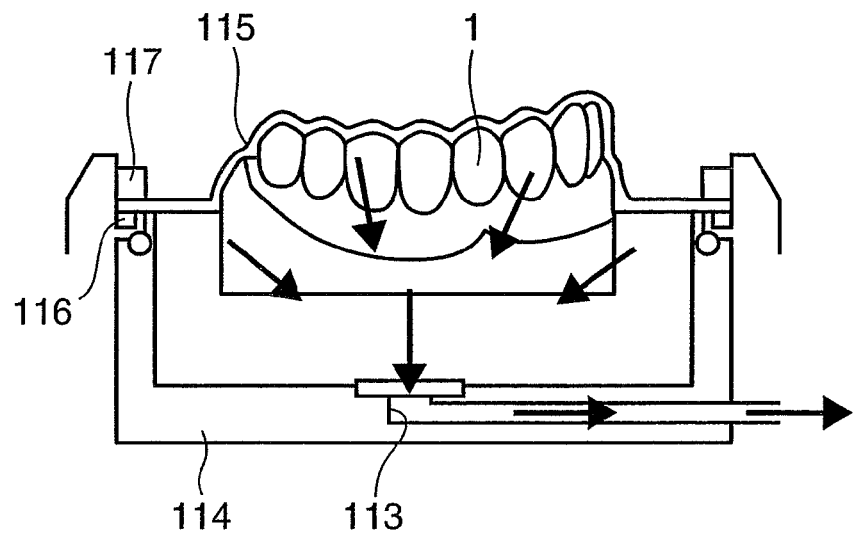
FIGS. 21A and 21B are diagrams showing the process of casting a dental mouthpiece using an EVA sheet.

At this time, air is sucked through the air suction holes 113, thereby generating an air flow to closely attach the EVA sheet 115 to the dental cast 1. In order to enable this suction, a cut 1a is made in the dental cast 1. This suction enables precise dental impression. The principle of such suction casting is only schematically shown in FIG. 21A. The electric heater 119 may also be lowered as the sheet fixing devices 116, 117 are lowered. This downward movement of the electric heater

Figure 21B:
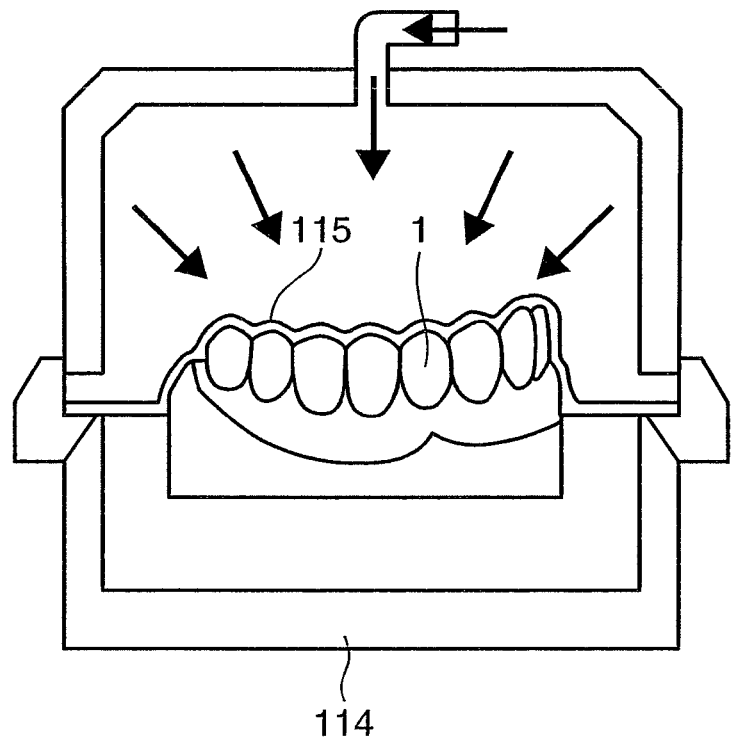

119 enables continuous heating. Alternatively, as shown in FIG. 21B, the dental mouthpiece can be cast by pressurizing air around the EVA sheet 115. This pressurization and the suction may be applied in combination.

The inner layer 7A is completed by the above casting. Up to Step S3, this method is the same as the conventional dental mouthpiece producing method. FIG. 19 is shown in FIGS. 2 to 11 on page 15 of "Not Only Mouth Guard! Casting Machine Application Manual" (cowritten by Maeda and Matsuda, published by Quintessence Publisher).

What should be noted next is that a vibrating element such as the electric motor 8 can be mounted in the inner layer 7A in Step S4 while the inner layer 7A is still hot. The material of the dental mouthpiece 7, particularly the above EVA exhibits high viscosity in its molten state to such an extent as to be used also as a main ingredient of so-called hot bond. Accordingly, the inner layer 7A having a high temperature immediately after being cast in a half molten state in Step S3 as described above exhibits high viscosity until it is cooled. An adhesive force given by the material of the inner layer 7A due to the remaining heat of the inner layer 7A can be utilized to mount the vibrating element. Specifically, it is sufficient to press the vibrating element such as the electric motor 8 against the inner layer 7A while the inner layer 7A still has a high temperature. In this way, the vibrating element can be temporarily fixed without using special fixing means such as adhesive.

If the adhesive force by the viscosity of the inner layer 7A is insufficient, such a shortage may be compensated for. For example, the vibrating element such as the electric motor 8 may be provided with a projection and the inner layer 7A may be formed with a part engageable with this projection, or the heated EVA may be poured into parts to be fixed as auxiliary adhesive.

What should be further noted is that the vibrating element such as the electric motor 8 can be sealed airtight in the inner layer 7A and the outer layer 7B in Step S5 shown in FIG. 19. Specifically, similar to Step S3, the heated EVA sheet 115 is placed on the inner layer 7A fitted with the vibrating element as described above, and an actuator is caused to suck. In this way, the outer layer 7B is formed and the vibrating element is sealed between the outer layer 7B and the inner layer 7A.

The softening temperature of the EVA sheet 115 as the material for the inner layer 7A and the outer layer 7B is set lower than the heat resistant temperature of the vibrating element. For example, if the electric motor 8 having a heat resistant temperature of 100° C. is used as the vibrating element, an EVA sheet having a softening point of 60 to 70° C. is selected as the EVA sheet 115. The use of such an EVA sheet enables the EVA sheet to be directly mounted on the vibrating element and the outer layer 7B to be cast by melting while enabling problems caused by an excessive temperature rise of the vibrating element to be securely prevented. "Bioplast" (product name) can be cited as an example of the EVA having such a low softening point.

If the heat resistant temperature of the vibrating element is even higher, materials having higher softening points can be used instead of EVA materials. Specifically, polyolefin materials having softening points of about 100° C. such as "MG-21" (product name) or PET-E materials having softening points between 100 and 200° C. such as "Duran" (product name) can be used.

After the dental mouthpiece 7 is fabricated in this way, EVA is peeled off from a part of the outer layer 7B corresponding to lead wires 8w of the electric motor 8, and the power feed cable 9 is connected with the lead wires 8w in Step S6 of FIG. 19. Thereafter, in Step S7, an end of an EVA tube 110 mounted on the power feed cable 9 is locally heated by means of a drier or the like to seal a connected part with the outer layer 7B airtight, thereby completing the dental mouthpiece 7.

The method for producing the dental mouthpiece 7 according to the first example has an advantage of reducing operation steps since the dental mouthpiece 7 can be fabricated with one dental impression. For example, a method shown in FIG. 12 requires two dental impressions. Specifically, after the inner layer 7A is competed, a second dental impression is performed using the impression material with the electric motor 8 or its dummy mounted in the inner layer 7A, and a plaster cast is formed again. After the EVA sheet 115 is placed on this plaster cast to form the outer layer 7B, the inner layer 7A having the actual electric motor 8 mounted therein and the outer layer 7B are welded.

Further, the method for producing the dental mouthpiece 7 according to the first example enables the production of a high-quality dental mouthpiece having high airtightness. Specifically, the inner layer 7A and the EVA sheet for the outer layer 7B softened by being uniformly and entirely heated by the heat of the mounted EVA sheet for the outer layer 7B become half molten to be naturally united. Thus, airtightness is higher, for example, as compared to the case where the inner layer 7A and the outer layer 7B already hardened are bonded to each other. Further, there are no inconveniences in the case of dental impression using a dummy such as problems of forming a clearance between the inner layer 7A and the outer layer 7B and making it impossible to fit the inner layer 7A into the outer layer 7B. This enables the production of a high-quality dental mouthpiece.

Figure 20:
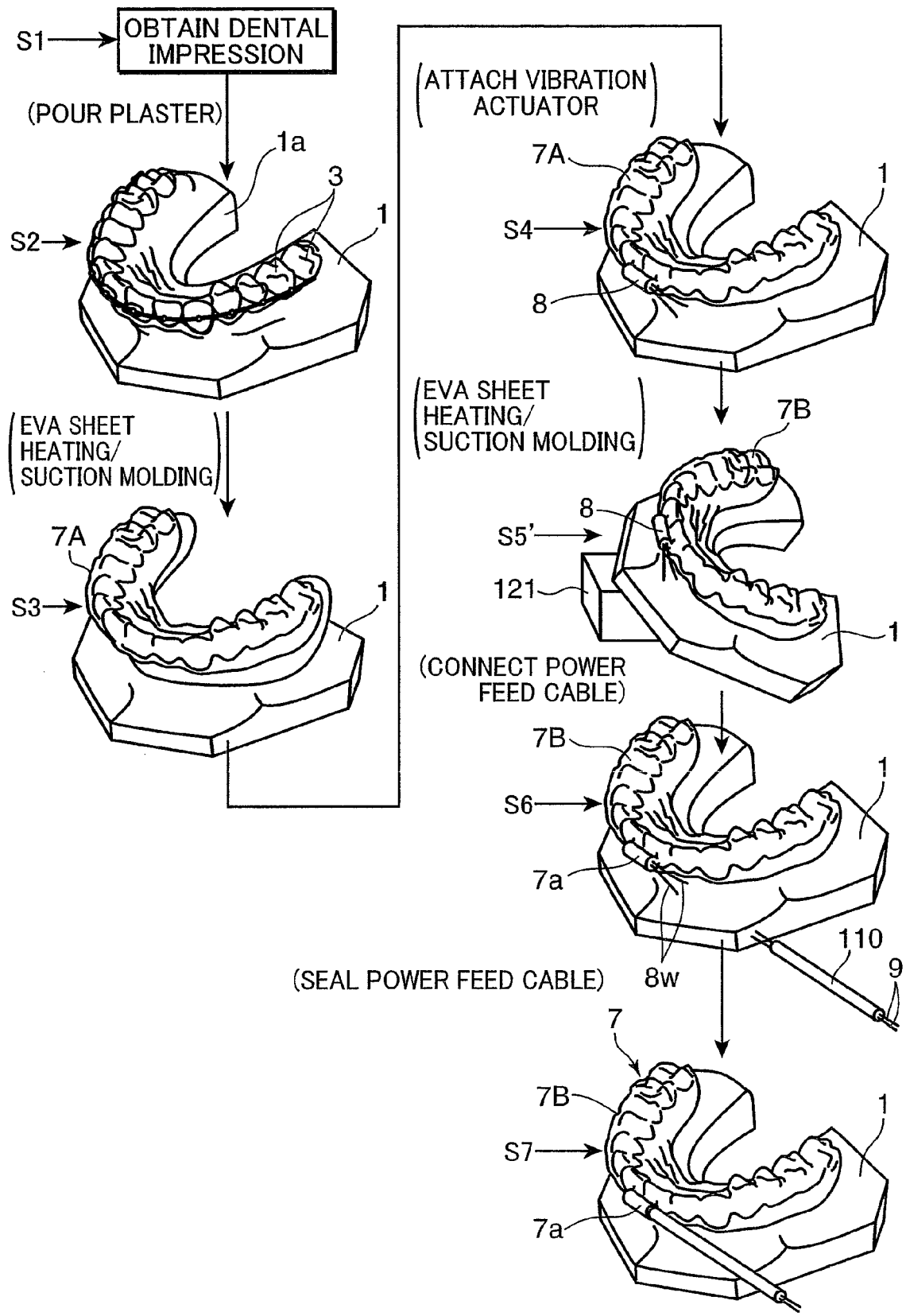
FIG. 20 is a diagram showing a second example of the dental mouthpiece producing method of the invention using the producing apparatus shown in FIG. 18.

FIG. 20 is a diagram showing a method for producing the dental mouthpiece according to a second example. Since this producing method is similar to the one according to the first example shown in FIG. 19, elements common to both examples are identified by common step numbers and are not described.

What should be noted in the producing method according to this second example is that the step of forming the outer layer 7B in Step S5 shown in FIG. 19 is changed to Step S5' shown in FIG. 20. In Step S5', the dental cast 1 having the inner layer 7A fitted with the vibrating element such as the electric motor 8 mounted thereon is set in an inclined state on the stage 112 shown in FIG. 18. This inclination is for preventing the dental cast 3 from being hidden from an air flow by the electric motor 8. This inclination can be made by placing a rest 121 as shown in FIG. 20 below a part of the dental cast 1 where the electric motor 8 is mounted.

It is sufficient for the material for the inner layer 7A and the outer layer 7B to have a softening point lower than the heat resistant temperature of the vibrating element such as the electric motor 8 and to be harmless to human bodies. The material is arbitrarily selected based on hardness required for the respective pieces 7A, 7B after casting within such a range as to meet these conditions. However, it is preferable to use a soft resin as the material. The use of the soft resin has advantages of alleviating stimuli given to the teeth and gums from the vibrating element, reducing loads given to the teeth and gums, mitigating discomfort such as pains, and improving wearing comfort as compared to hard dental mouthpieces.

On the other hand, the use of a hard resin as the material has advantages of enabling the dental mouthpiece to be precisely cast, less deformation of the dental mouthpiece by the storage environment, and easier quality maintenance. Accordingly, a hard resin may be used in the case of attaching more importance to these advantages.

Further, the material for the inner layer 7A and the one for the outer layer 7B may differ. For example, a dental mouthpiece having an overlaid structure comprised of an inner layer 7A made of a soft resin and an output layer 7B made of a hard resin has advantages that the inner layer 7A effectively alleviates impacts of a vibrating element to reduce loads on teeth to be aligned and gums, and the outer layer 7B made of the hard resin is easy to store because it is difficult to deform by the environment. Conversely, a dental mouthpiece having an overlaid structure comprised of an inner layer 7A made of a hard resin and an output piece 7B made of a soft resin has advantages that the outer layer 7B made of the soft resin absorbs impacts during sport and everyday life to effectively suppress damages of the dental mouthpiece and the teeth on which the dental mouthpiece is mounted resulting from the impacts, and the inner layer 7A made of the hard resin enables production of a dental mouthpiece having a precise inner shape. Further, this dental mouthpiece can be more easily kept in shape than those entirely made of the soft resin.

Further, even in a dental mouthpiece made up of a single layer without having an overlaid structure as above, it is possible to mixedly provide soft parts, i.e. those for weakly transmitting stimuli to the teeth 3 and hard parts, i.e. those for strongly transmitting stimuli to the teeth 3.

Resins used for the material of the dental mouthpiece are: EVAs→polyolefins→polyesters and the like in a decreasing order of softness. Even the same material has different compound ratios and hardnesses depending on products. Most EVAs are soft materials having a shore hardness of about 80 to 90 and widely used as the material for soft dental mouthpieces. Conversely, most polyesters are hard materials and widely used as the material for hard dental mouthpieces. There are soft polyolefins and hard polyolefins depending on their compound ratios, but polyolefins are generally used as materials having hardnesses between the EVAs and the polyesters.

Next, dental mouthpieces according to ninth to fifteenth embodiments are described with reference to FIGS. 22 to 28. Each of the dental mouthpieces according to these embodiments has dividing portions by dividing specified parts other than a part corresponding to teeth 3g, 3h to be aligned. These dividing portions suppress the transmission of mechanical vibration generated by a vibrating element so that the mechanical vibration acts restrictedly on the teeth 3g, 3h to be aligned. Although an electric motor 8 is shown as the vibrating element in FIGS. 22 to 28, the vibrating element may be other actuators, for example, a permanent magnet.

Figure 22:
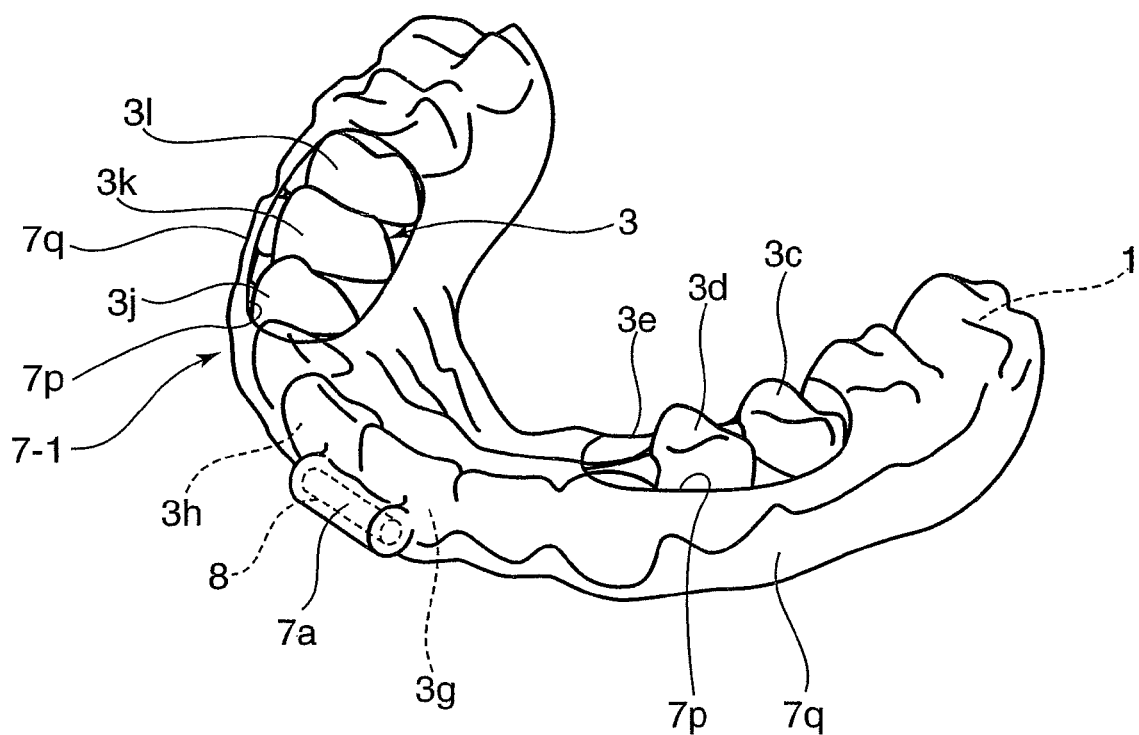
FIG. 22 is a perspective view showing a state where a dental mouthpiece according to a ninth embodiment of the invention is mounted on teeth.

FIG. 22 shows a dental mouthpiece 7-1 according to the ninth embodiment. The dividing portions of this dental mouthpiece 7-1 are cutout portions 7p. These cutout portions 7p are formed by cutting out tooth crown portions of the dental mouthpiece 7-1 except at the part corresponding to the teeth 3g, 3h to be aligned. For example, elliptical cutouts are made in the tooth crown portions for teeth 3c to 3e, 3j to 3l in FIG. 22. Dental root portions 7q left in the dental mouthpiece 7-1 at the parts where the cutout portions 7p are formed integrally connect parts before and after the cutout portions 7p.

Figure 23:
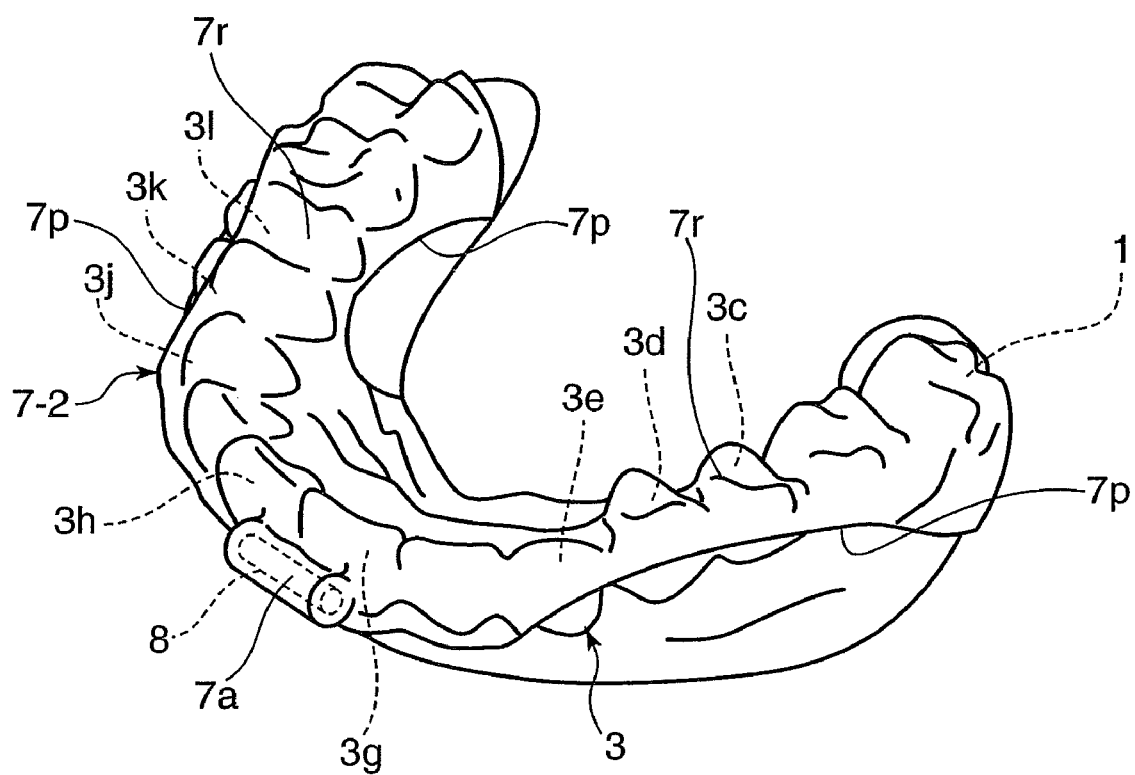
FIG. 23 is a perspective view showing a state where a dental mouthpiece according to a tenth embodiment of the invention is mounted on teeth.

FIG. 23 shows a dental mouthpiece 7-2 according to the tenth embodiment. The dividing portions of this dental mouthpiece 7-2 are also cutout portions 7p. These cutout portions 7p are formed by cutting out tooth root portions of the dental mouthpiece 7-2 except at the part corresponding to the teeth 3g, 3h to be aligned. For example, elliptical cutouts are made in the tooth root portions for the teeth 3c to 3e, 3j to 3l in FIG. 23. Tooth crown portions 7r left in the dental mouthpiece 7-2 at the parts where the cutout portions 7p are formed integrally connect parts before and after the cutout portions 7p.

In the dental mouthpieces 7-1, 7-2, the electric motor 8 for generating mechanical vibration is stored at the part corresponding to the teeth 3g, 3h to be aligned, and the cutout portions (dividing portions) 7p for suppressing the transmission of the mechanical vibration are formed in the parts other than the one corresponding to the teeth 3g, 3h to be aligned. This enables the partial and precise application of vibration to the teeth 3g, 3h to be aligned.

The cutout portions 7p are formed by a post-processing of, e.g. cutting off the tooth crown portions or the tooth root portions of the dental mouthpiece 7 shown in FIG. 1 using a cutter knife or the like. Accordingly, the dental mouthpieces 7-1, 7-2 having these cutout portions 7p can be easily produced. For example, a dental mouthpiece having the above cutout portions 7p can be easily produced through this post-processing from a dental mouthpiece actually worn by a user.

By connecting the parts before and after the cutout portions 7p by the tooth root portions 7q or the tooth crown portions 7r left in the dental mouthpieces 7-1, 7-2, the shapes of the dental mouthpieces 7-1, 7-2 can be so kept as to be entirely mountable on the teeth 3. Such shapes facilitate an operation of mounting the dental mouthpieces 7-1, 702 on the teeth 3, thereby enabling the electric motor 8 to be precisely positioned at the part corresponding to the teeth 3g, 3h to be aligned in the worn state.

Figure 24:
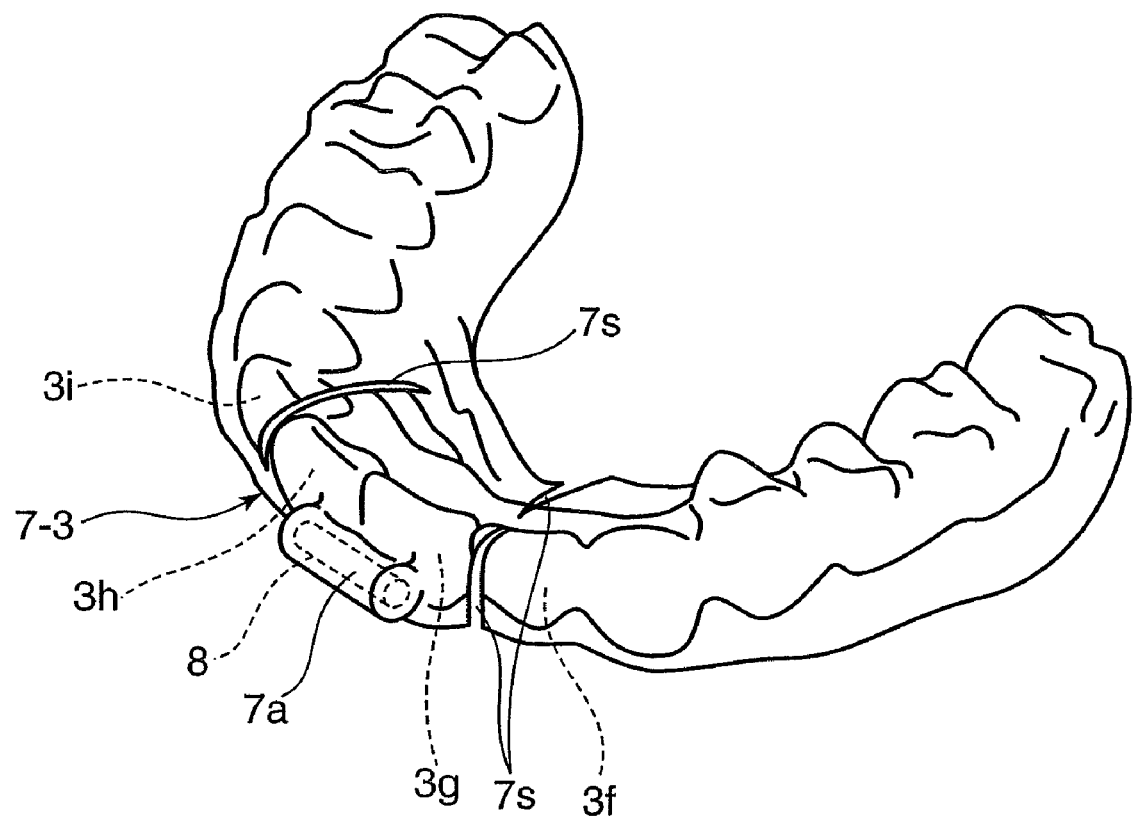
FIG. 24 is a perspective view showing a dental mouthpiece according to an eleventh embodiment of the invention.

FIG. 24 shows a dental mouthpiece 7-3 according to the eleventh embodiment. The dividing portions of this dental mouthpiece 7-2 are slit portions 7s formed in parts of the dental mouthpiece 7-3 except a part corresponding to the teeth 3g, 3h to be aligned. These slit portions 7s are formed in parts between the teeth 3f, 3g and between the teeth 3h, 3i in FIG. 24, and parts before and after the respective slit portions 7s are integrally connected. The right slit portions 7s in FIG. 24 extend from a tooth root side toward a tooth crown side, whereas the left slit portion 7s extends from the tooth crown side toward the tooth root side. In the present invention, the directions of these slit portions are not limited.

The dental mouthpiece 7-3 according to this eleventh embodiment can achieve functions and effects similar to those of the dental mouthpieces 7-1, 7-2.

Figure 25:
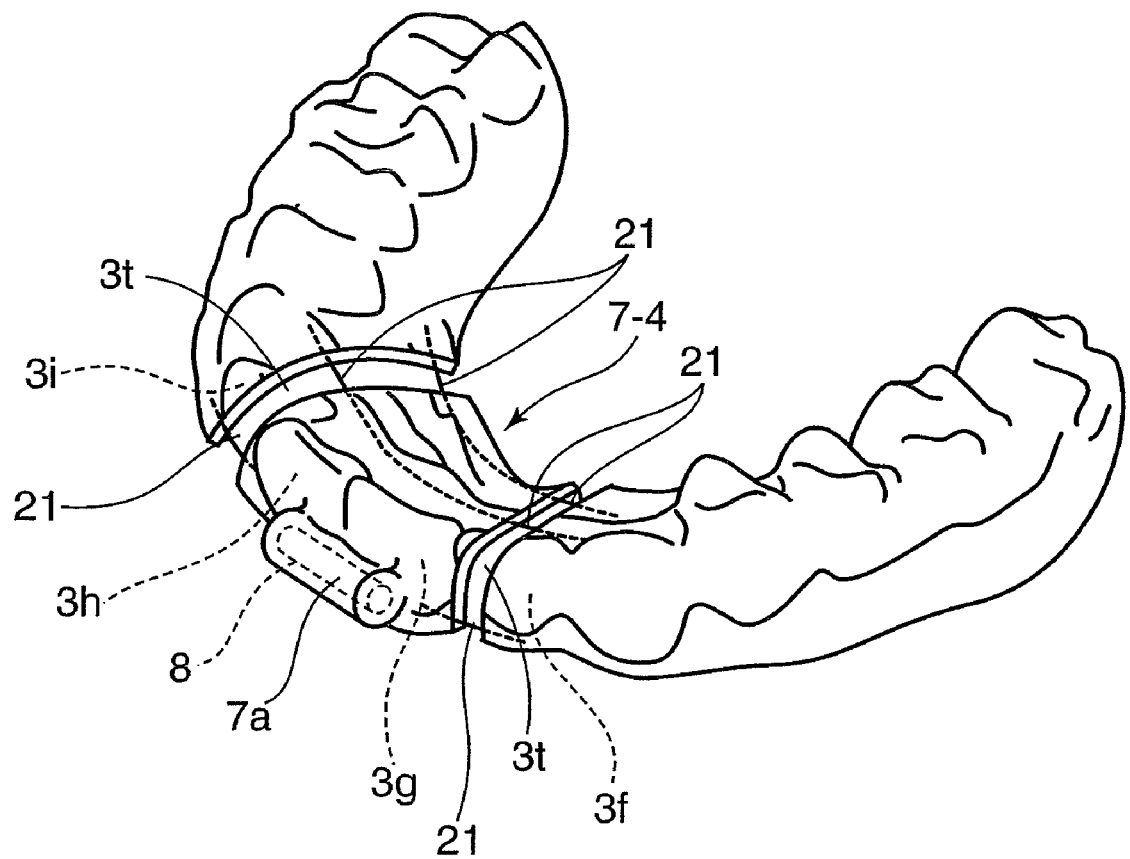
FIG. 25 is a perspective view showing a dental mouthpiece according to a twelfth embodiment of the invention.

FIG. 25 shows a dental mouthpiece 7-4 according to the twelfth embodiment. The dividing portions of this dental mouthpiece 7-4 are cut portions 7t formed by cutting parts except at the one corresponding to the teeth 3g, 3h to be aligned. In FIG. 25, the cut portions 7t are formed by making cuts between the teeth 3f, 3g and between 3h, 3i, and parts before and after the respective cut portions 7t are integrally connected, for example, by means of wires 21 or the like insert-cast in the dental mouthpiece 7-4.

The dental mouthpiece 7-4 according to this twelfth embodiment can also achieve functions and effects similar to those of the dental mouthpieces 7-1, 7-2 and 7-3.

Figure 26:
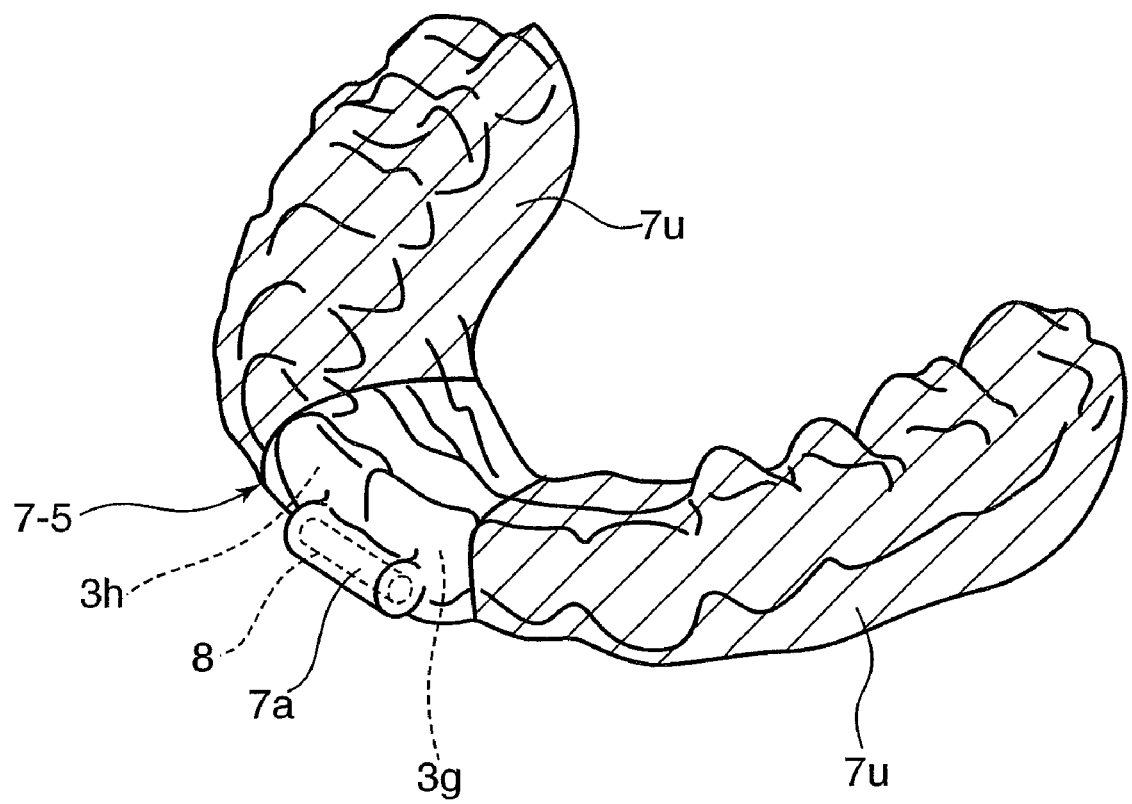
FIG. 26 is a perspective view showing a dental mouthpiece according to a thirteenth embodiment of the invention.

FIG. 26 shows a dental mouthpiece 7-5 according to the thirteenth embodiment. The dividing portions of this dental mouthpiece 7-5 are soft portions 7u made of a soft material. In this dental mouthpiece 7-5, the part corresponding to the teeth 3g, 3h to be aligned is made of an ordinary mouthpiece material, whereas the other parts (parts hatched with oblique lines in FIG. 26) are made of the soft material less likely to transmit the mechanical vibration to form the soft portions 7u.

The dental mouthpiece 7-5 according to this thirteenth embodiment can also achieve functions and effects similar to those of the dental mouthpieces 7-1, 7-2, 7-3 and 7-4. Further, the dental mouthpiece 7-5 has an advantage of having no clearances such as the cutout portions 7p and the slit portions 7s.

Figure 27:
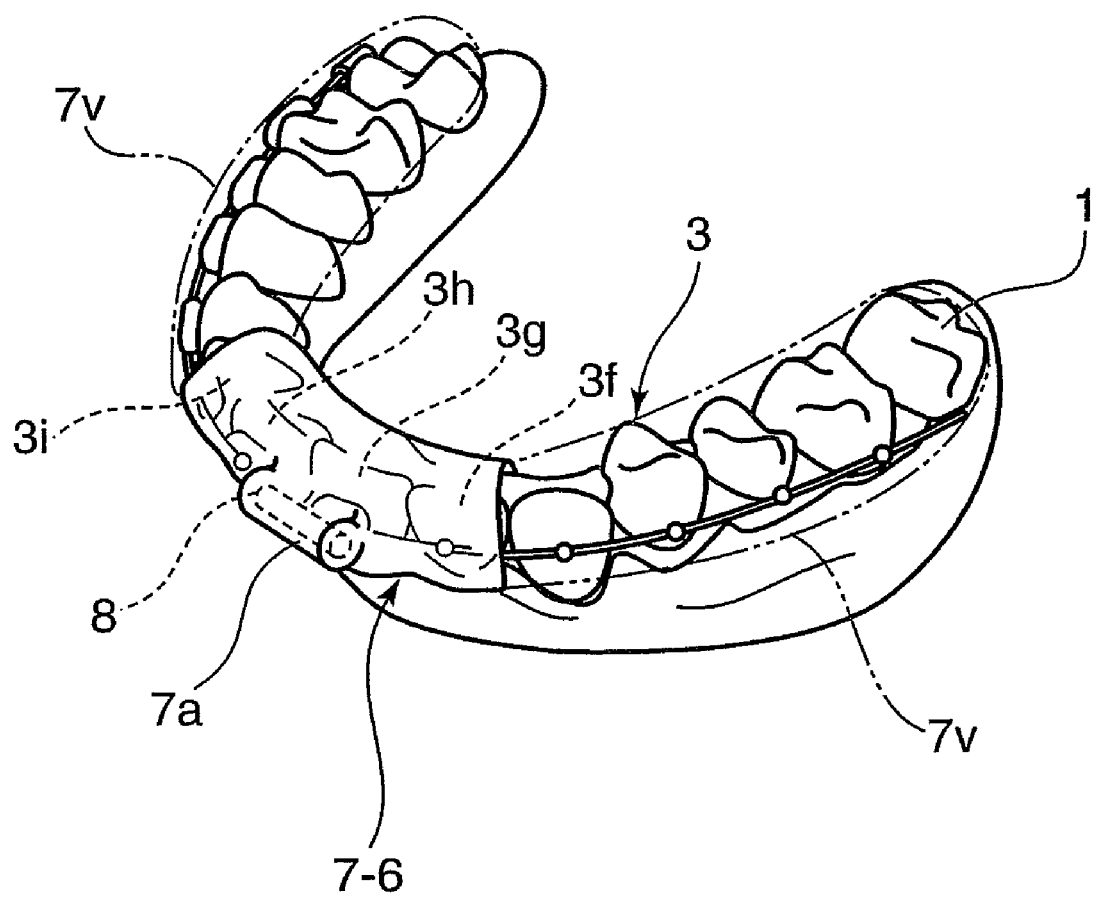
FIG. 27 is a perspective view showing a state where a dental mouthpiece according to a fourteenth embodiment of the invention is mounted on teeth.

FIG. 27 shows a dental mouthpiece 7-6 according to the fourteenth embodiment. The dividing portions of this dental mouthpiece 7-6 are cutoff portions 7v shown by chain double-dashed line. These cutoff portions 7v are formed by cutting off parts of the dental mouthpiece 7-4 at parts at least except the one corresponding to the teeth 3g, 3h to be aligned (teeth 3f, 3i near the teeth 3g, 3h to be aligned are also included in FIG. 27). Accordingly, this dental mouthpiece 7-6 is mounted only on the teeth 3g, 3h to be aligned (or on the teeth 3g, 3h to be aligned and their neighboring teeth 3f, 3i).

The dental mouthpiece 7-6 according to this fourteenth embodiment can also achieve functions and effects similar to those of the dental mouthpieces 7-1, 7-2, 7-3, 7-4 and 7-5.

The dental mouthpiece 7-6 may be mounted on only a single tooth. For example, the dental mouthpiece 7-6 may be so shaped and constructed as to be mounted only on one tooth 3g or 3h to be aligned.

In the case where all the teeth 3a to 3n are to be aligned, the dental mouthpiece 7-6 may be individually mounted on each of the teeth 3a to 3n to be aligned. In such a case, the dental mouthpieces 7-6 can be successively detached from the teeth for which orthodontic treatment has been finished. Alternatively, the dental mouthpiece 7-6 can be successively mounted and detached. For example, a treatment is first conducted by mounting the dental mouthpiece 7-6 on the teeth at the back side, and the dental mouthpiece 7-6 is detached after the orthodontic treatment is finished. A subsequent treatment is conducted by mounting the dental mouthpiece 7-6 on the teeth before the already treated teeth. In this way, the dental mouthpiece 7-6 can be successively mounted on and detached from the teeth from the posterior tooth side toward the front tooth side.

Figure 28:
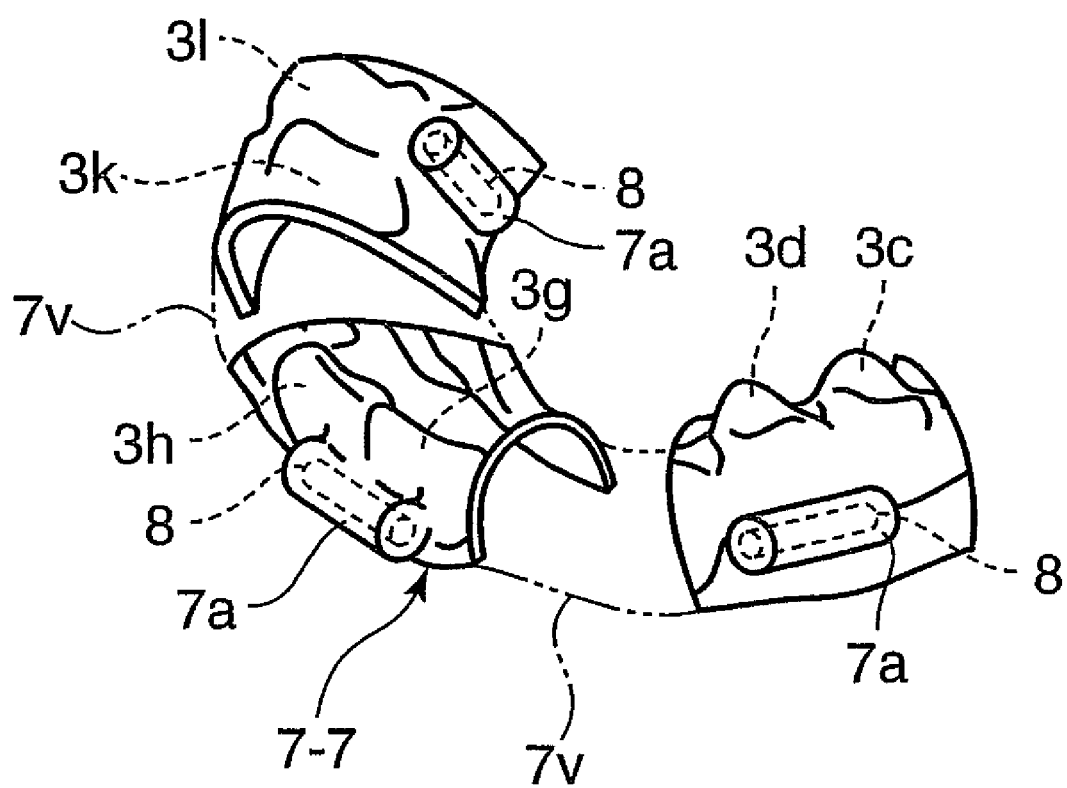
FIG. 28 is a perspective view showing a dental mouthpiece according to a fifteenth embodiment of the invention.

FIG. 28 shows a dental mouthpiece 7-7 according to the fifteenth embodiment. The dividing portions of this dental mouthpiece 7-7 are cutoff portions 7v (see chain double-dashed line) formed by cutting off the dental mouthpiece 7-7 except at parts corresponding to the teeth 3c, 3d to be aligned, the teeth 3g, 3h to be aligned and the teeth 3k, 3l to be aligned. Accordingly, the dental mouthpiece 7-7 is mounted only on the teeth 3c, 3d to be aligned, the teeth 3g, 3h to be aligned and the teeth 3k, 3l to be aligned.

The dental mouthpiece 7-7 according to this fifteenth embodiment can also achieve functions and effects similar to those of the dental mouthpieces 7-1, 7-2, 7-3, 7-4, 7-5 and 7-6.

The dental mouthpiece 7-7 is divided into a plurality of (three in this example) mutually independent segments by the cutoff portions (dividing portions) 7v. In this construction, the direction and intensity of the vibration to be applied can be changed for each segment, which enables adaptations to various teethes and bites. One or more vibrating elements (electric motor(s) 8 and/or permanent magnet(s) 15) can be stored for each segment. In the case of storing a plurality of vibrating elements, the kind (e.g. electric motor or permanent magnet) of the vibrating elements, the directions and intensities of the vibration can be different from each other.

Since the parts before and after the divided sections are integrally connected to each other in the dental mouthpieces 7-1 to 7-4 according to the ninth to twelfth embodiments, each dental mouthpiece is entirely formed by a single segment, but the parts before and after the dividing portions can be seen as the mutually independent segments since the respective dividing portions suppress the transmission of the mechanical vibration. Accordingly, in a construction in which vibrating elements such as the electric motors 8 are stored in the segments before and after the dividing portions similar to the dental mouthpiece 7-7 according to the fifteenth embodiment, the direction and intensity of the vibration to be applied can be changed for each segment, thereby enabling adaptations to various teethes and bites. Further, it is also possible to store one or more vibrating elements in each segment.

Since the dividing portions are the cutout portions 7p, the slit portions 7s or the cut portions 7t in the dental mouthpiece 7-1 to 7-4 according to the ninth to twelfth embodiments, the segments unnecessary for the treatment by a treatment plan or the segments having used for the already finished orthodontic treatment can be locally removed by being cut at the dividing portions if the vibrating elements are stored in the respective segments before and after the dividing portions. It is more preferable to have such a construction that the parts cut at the dividing portions can be reconnected. This construction can be realized, for example, by mounting fittings attachable to and detachable from each other, magnetic elements attracting each other, adhesive materials or the like at the cut positions.

The dental mouthpieces 7-1 to 7-7 according to the above embodiments are not limited to those having an inner and outer overlaid structure comprised of the inner layer 7A and the outer layer 7B. In short, it is sufficient to store the vibrating element at the part corresponding to the tooth to be aligned. For example, a casing storing the electric motor 8, a button battery 11' and the permanent magnet 15 may be joined with a main body of a dental mouthpiece having a normal single-layer structure at a position near the tooth to be aligned.

Figure 29:
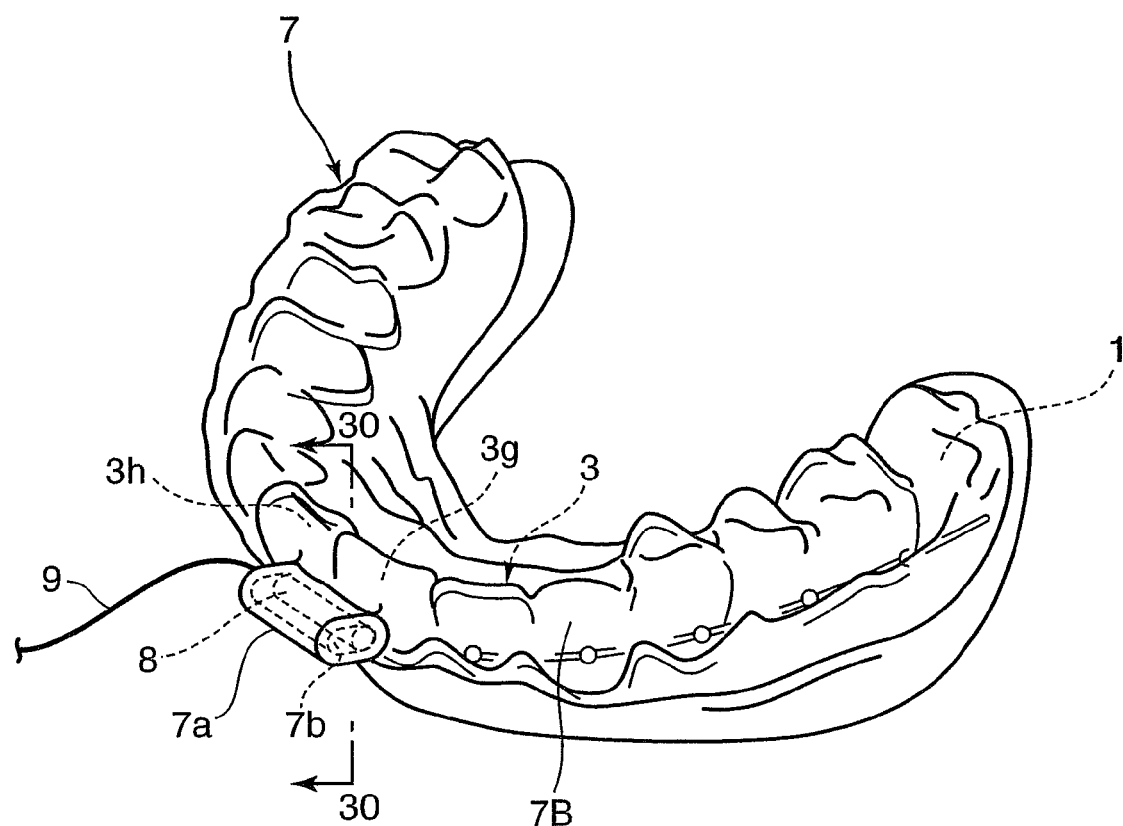
FIG. 29 is a perspective view showing a state where a dental mouthpiece according to a sixteenth embodiment of the invention is mounted on teeth of the lower dental arch of a user.
Figure 30:
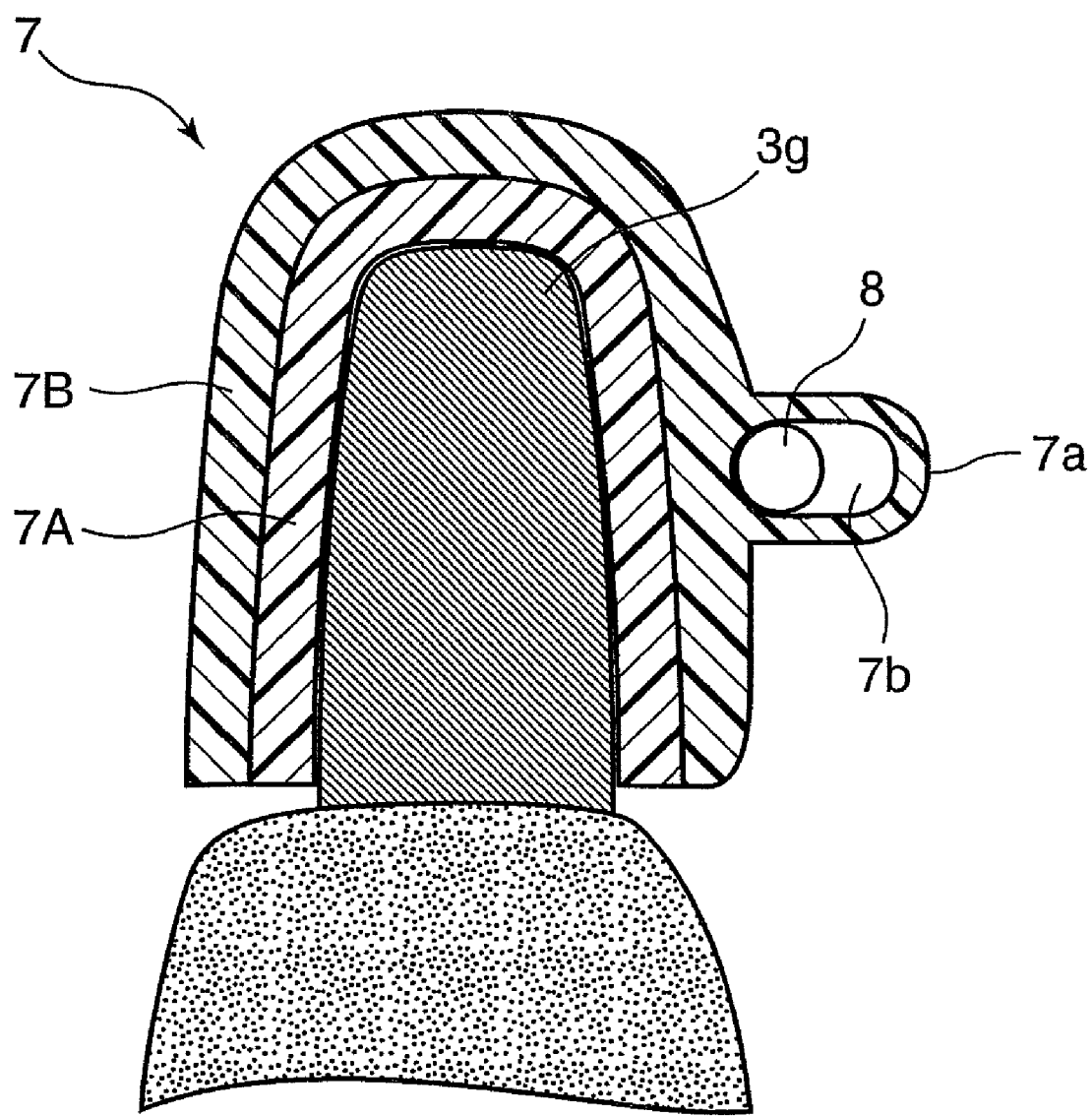
FIG. 30 is a section along the line 30-30 in FIG. 29.
Figure 31:
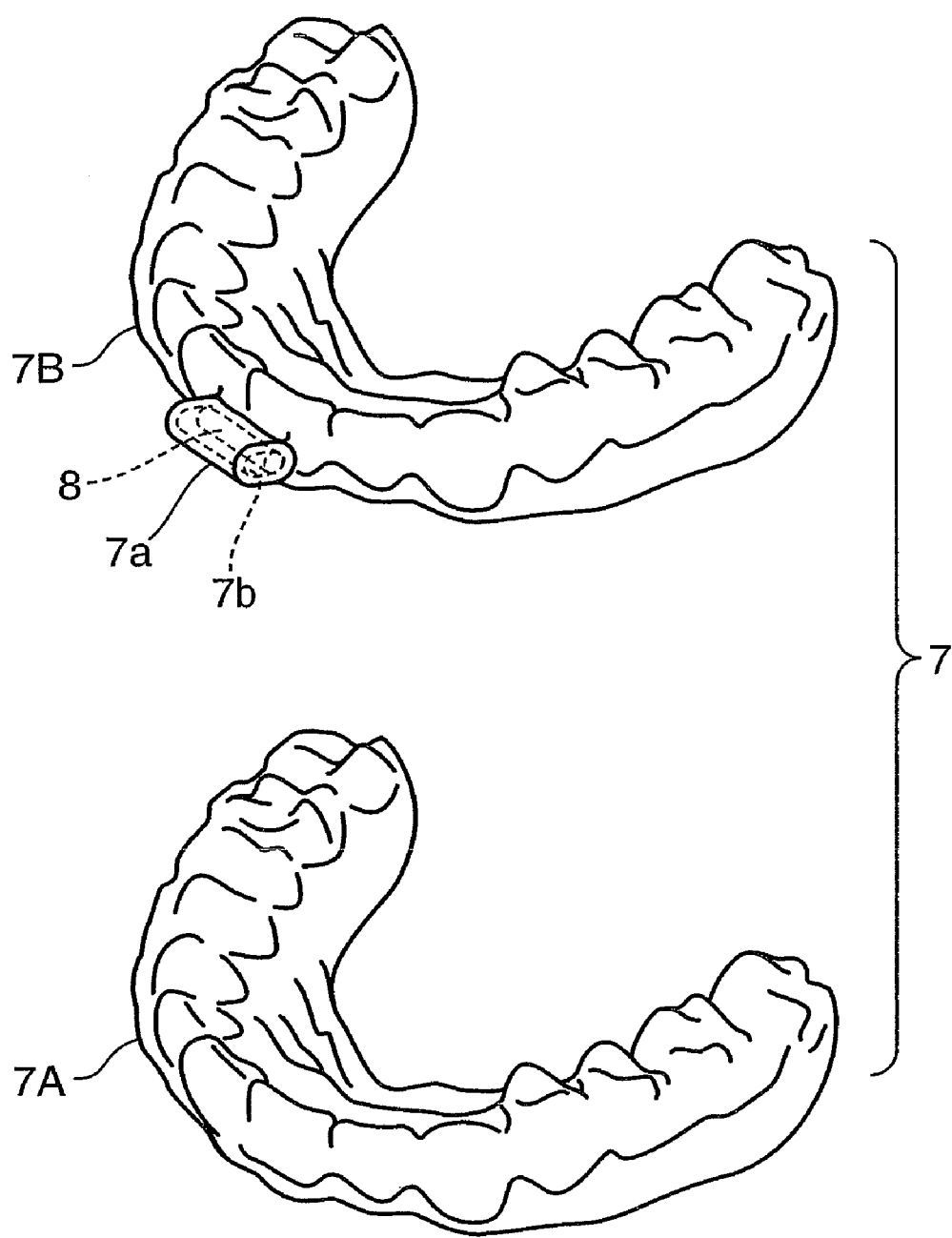
FIG. 31 is an exploded perspective view showing the dental mouthpiece according to the sixteenth embodiment of the invention when viewed from topside.

FIG. 29 is a perspective view showing a state where a dental mouthpiece according to a sixteenth embodiment of the invention is mounted on the lower dental arch of a user, and FIG. 30 is a section along the line 30-30 in FIG. 29.

The dental mouthpiece 7 according to this embodiment is characterized by the shape of a storage space of a vibrating element storing portion. This storage space is so shaped as to provide the vibrating element with a play permitting the vibrating element itself to move in the storage space.

In FIG. 29, an outer layer 7B constituting the dental mouthpiece 7 is formed with a bulge portion 7a similar to the first embodiment, and an electric motor 8 as a vibrating element is stored in this bulge portion 7a. This electric motor 8 has a cylindrical shape and is stored in the bulge portion 7a in such a posture that a direction of the central axis thereof is a horizontal direction (transverse direction) along the teeth 3.

On the other hand, a storage space 7b formed in the bulge portion 7a, i.e. a space for storing the electric motor 8 has a cylindrical shape whose cross section normal to longitudinal direction has an elliptical shape longer in horizontal direction. Accordingly, the shape of the storage space 7b is larger than the outer shape of the electric motor 8 and provides a clearance or a play extending in horizontal direction (inward and outward directions of the buccal cavity).

The storage space 7a according to this embodiment permits the electric motor 8 to be displaced along horizontal direction (inward and outward directions of the buccal cavity) without completely restraining the electric motor 8, i.e. provides the electric motor 8 with a play. Accordingly, a vibration load generated by the electric motor 8 as the vibrating element causes the electric motor 8 itself to vibrate along the direction of the above clearance (horizontal direction) and to collide with the wall surface defining the storage space 7b. This vibration load amplifies vibration to be applied to the teeth 3 of the user wearing the dental mouthpiece 7, thereby further improving the orthodontic effect by that much.

Figure 32A:
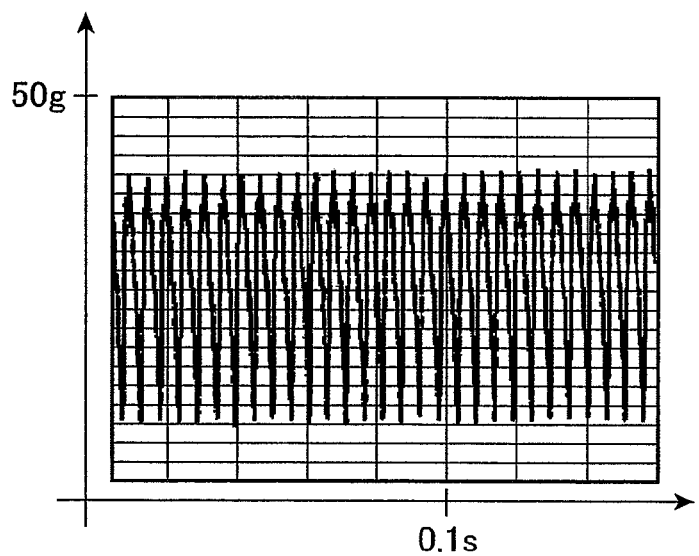
FIG. 32 is a graph showing an experiment result of the inventors of the present application.
Figure 32B:
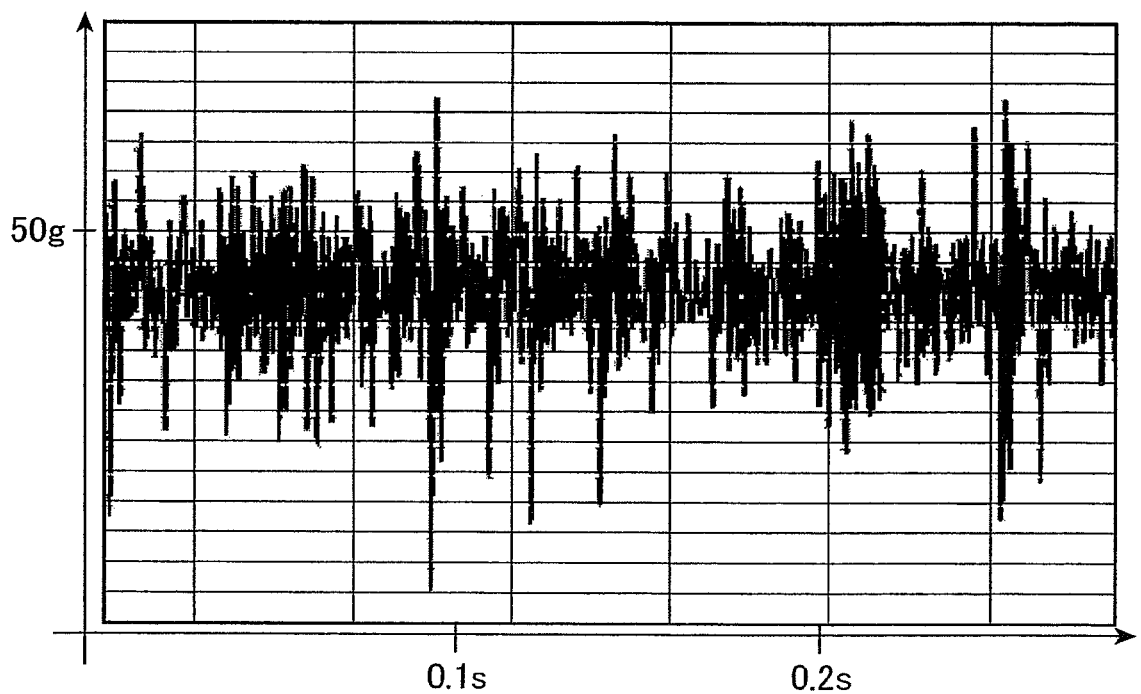

FIG. 32 are graphs showing an experiment result obtained by the inventors of the present application. FIG. 32A shows the amplitude of vibration to be applied to the teeth 3g, 3h to be aligned from a dental mouthpiece 7 whose storage space 7b has a shape equal to the outer shape of the electric motor 8, i.e. a dental mouthpiece 7 in which the electric motor 8 is completely restrained in the storage space 7 as a reference example, and FIG. 32B shows the amplitude of vibration in the case where a play is provided in the storage space 7b as shown in FIG. 29.

FIG. 32A shows that regular vibration of about 200 Hz is applied with a vibration load of about 30 g by the eccentric weight of the electric motor 8 in the case where the electric motor 8 is completely restrained in the storage space 7b. On the other hand, FIG. 32B shows that vibration is irregular, but the vibration load is increased (doubled) up to about 60 g in the case where there is the play.

In this embodiment, the direction of the play (direction of the clearance) coincides with a direction conforming to the aligning direction of the teeth 3g, 3h to be aligned in the storage space 7b. This largely contributes to the promotion of the orthodontic effect.

Figure 33:
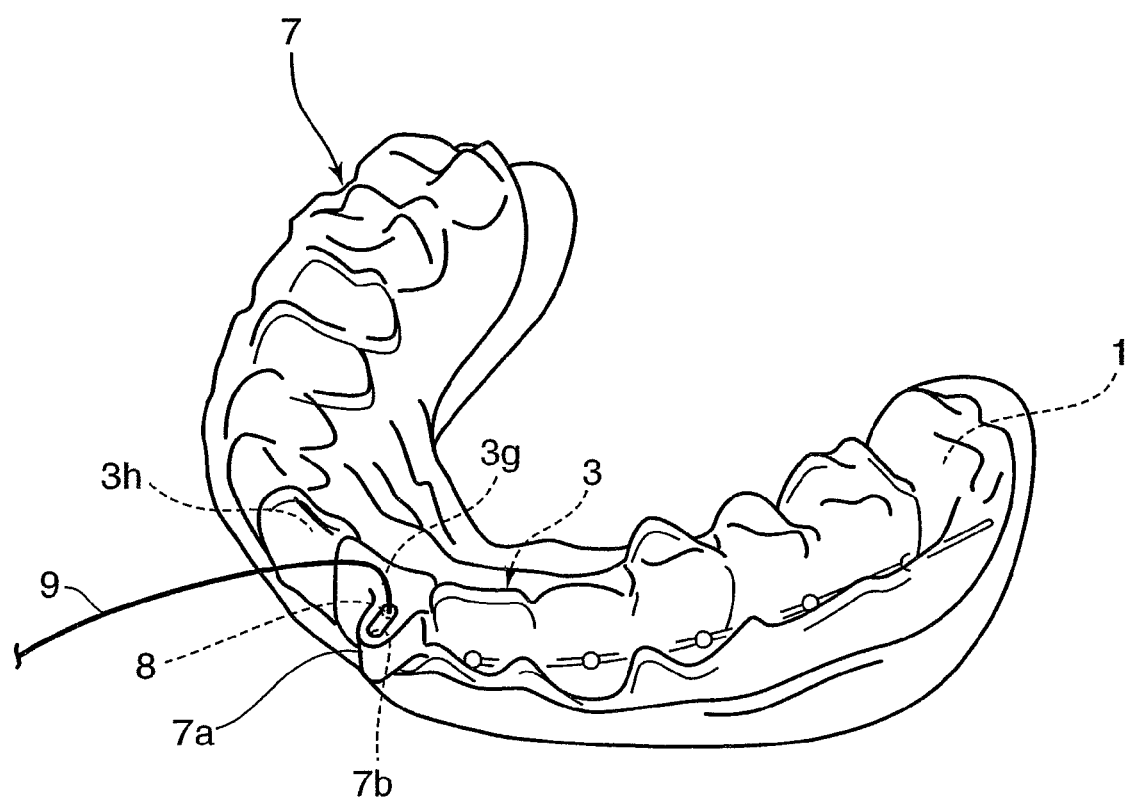
FIG. 33 is a perspective view of an example of a dental mouthpiece similar to the dental mouthpiece according to the sixteenth embodiment of the invention, but adopting a different orthodontic method.

For example, in the case of retracting a tooth sticking out forward and in the case of pulling a retracted tooth forward, the direction of the clearance may coincide with forward and backward directions. Further, in the case of aligning a twisted tooth, the direction of the clearance may coincide with a direction in which the tooth should be twisted back and which is substantially normal to the tooth surface. In an example shown in FIG. 33, the direction of the clearance is set to be substantially normal to the right half of the tooth surface of the tooth 3g to be aligned, which is supported to be twisted in counterclockwise direction when viewed from above.

A vibration effect utilizing such a clearance enables the application of the vibration load having high directivity to the teeth. For example, even if a vibrating element exemplified by the electric motor 8 and having high directivity cannot be used in light of cost and size and, instead, an inexpensive and small-sized rotary motor or vibration motor has to be used, sufficient stimuli can be given to promote the orthodontic effect by applying a vibration load having high directivity to the tooth to be aligned.

Figure 34:
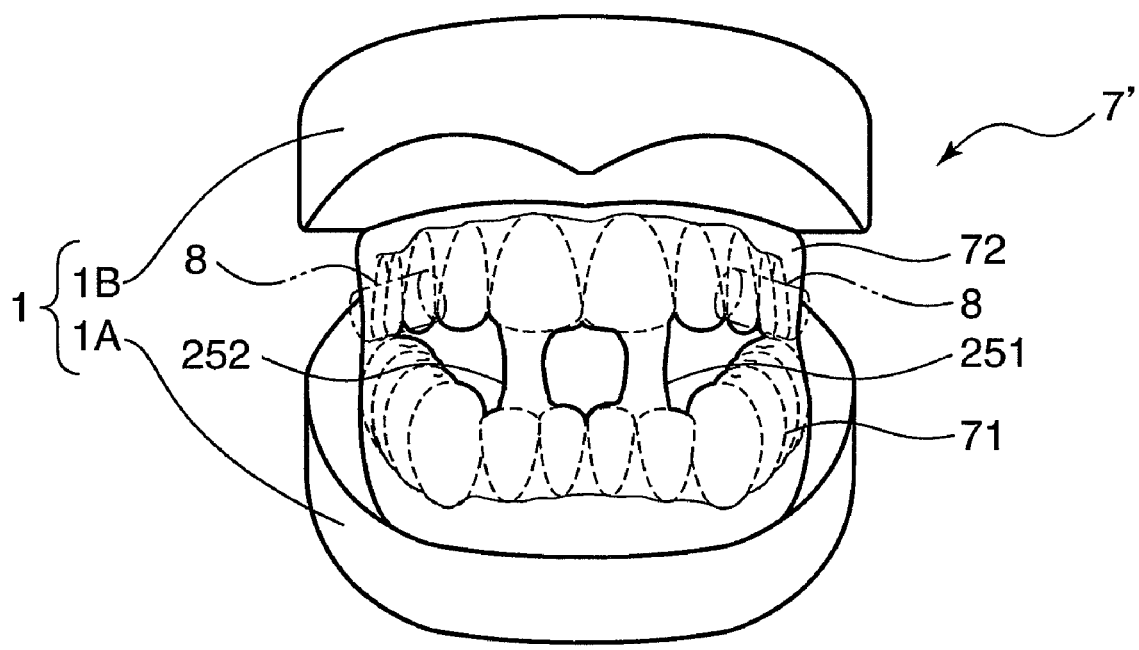
FIG. 34 is a perspective view showing a state where a dental mouthpiece according to a seventeenth embodiment of the invention is mounted on a dental cast of a user.

A seventeenth embodiment of the present invention is described with reference to FIG. 34. FIG. 34 is a perspective view showing a state where a dental mouthpiece 7' according to one embodiment of the present invention is mounted on a dental cast 1 of a user. The dental mouthpiece 7' of this embodiment includes a lower layer 71 corresponding to a dental cast 1A of the lower dental arch, an upper layer 72 corresponding to a dental cast 1B of the upper dental arch, connecting members 251, 252 connecting both layers 71, 72 at positions distanced from teeth to be aligned, and electric motors 8 as one example of a vibrating element. The upper layer 72 is mountable on the upper teeth, and the lower layer 71 is mountable on the lower teeth.

The lower layer 71 and the upper layer 72 of this dental mouthpiece 7' are both produced using an apparatus equivalent to the producing apparatus 111 shown in FIG. 18 by a method equivalent to the producing method shown in FIG. 19. Thereafter, the connecting members 251, 252 are formed in the following manner.

First, the lower layer 71 and the upper layer 72 produced as above are mounted on corresponding dental casts 1A, 1B of the dental cast 1 having the bite thereof adjusted. Subsequently, EVA columns having the opposite ends thereof heated to be molten are caused to stand at specified positions of the lower layer 71 with both dental casts 1A, 1B opened, and then the dental casts 1A, 1B are closed up to a specified angle. In this way, the ends of the EVA columns at, an opposite side come into contact with the upper layer 72. The EVA columns become the connecting members 251, 252 connecting both layers 71, 72 by being cooled in this state, whereby a pair of upper and lower dental mouthpieces 7' is completed.

Figure 35:
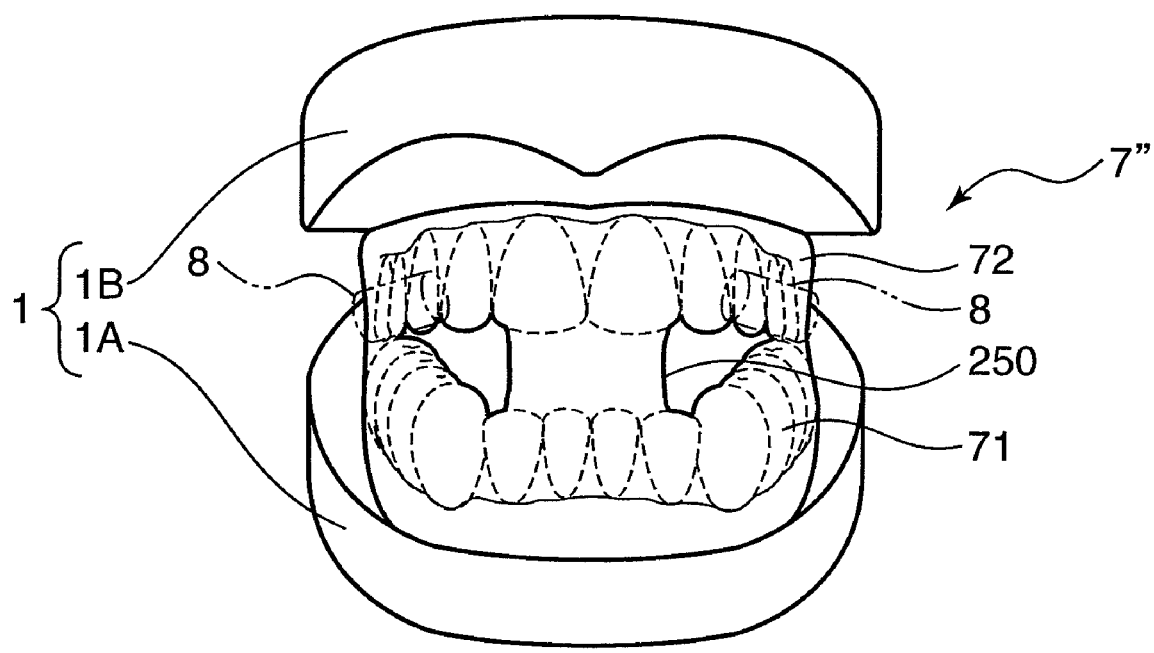
FIG. 35 is a perspective view showing a state where a dental mouthpiece according to an eighteenth embodiment of the invention is mounted on teeth.

The connecting members 251, 252 are provided at the positions distanced from the teeth to be aligned between the upper and lower layers 72, 71. For example, if the teeth to be aligned are left and right molar teeth (e.g. teeth 3a to 3d and 3k to 3n in the teeth shown in FIG. 1) and the vibrating elements such as the electric motors 8 are built in the dental mouthpiece 7' at positions near these teeth, the connecting members 251, 252 may be formed at the positions near the front teeth (central incisors) 3g, 3h as shown in FIG. 34. Alternatively, only a single connecting member 250 may be formed as in a dental mouthpiece 7" shown as an eighteenth embodiment in FIG. 35. On the other hand, if the teeth to be aligned are front teeth (lateral incisors) 3f, 3i and front teeth (canine teeth) 3e, 3j shown in FIG. 1 and the vibrating element such as the electric motor 8 is built in at the position shown in FIG. 2, the connecting members may be formed at positions near the left and right posterior teeth (e.g. at positions of the teeth 3c, 3d and teeth 3k, 3l of FIG. 1 or at their neighboring positions).

Figure 36:
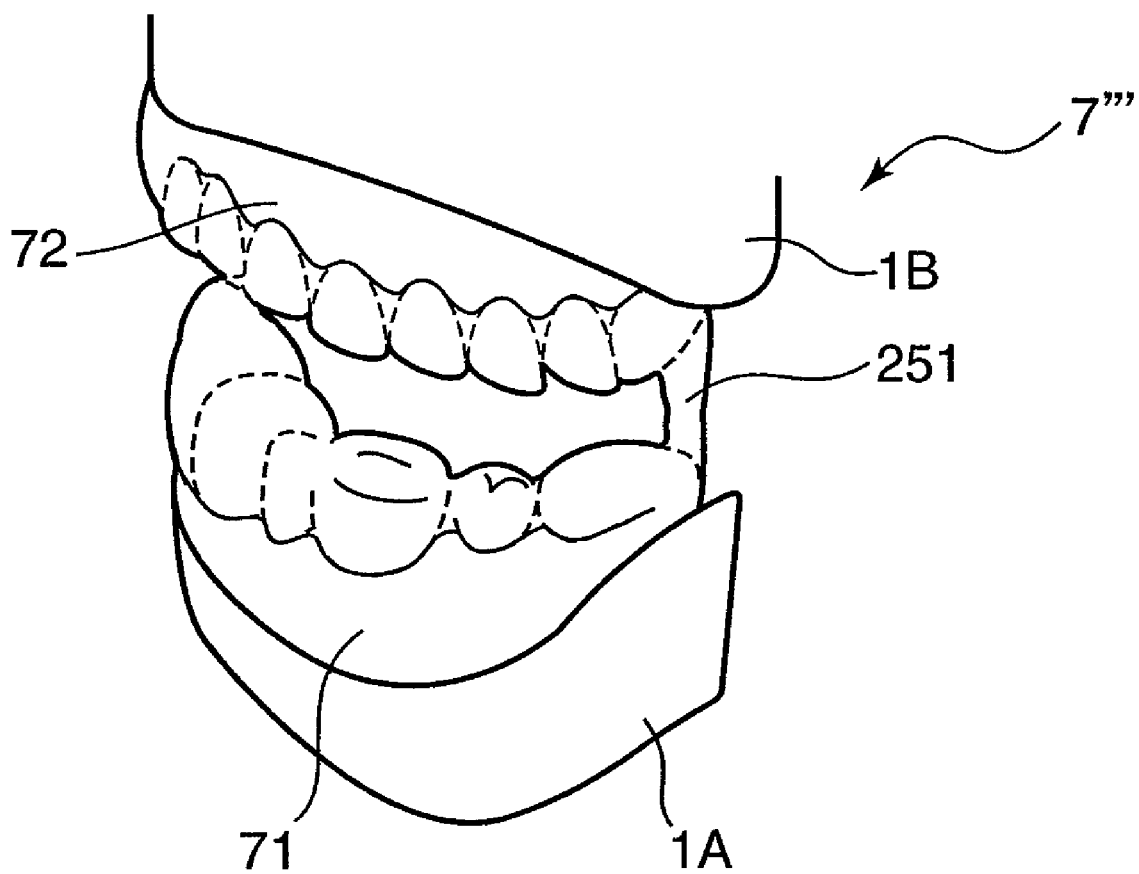
FIG. 36 is a perspective view showing a state where a dental mouthpiece according to a nineteenth embodiment of the invention is mounted on teeth.

In a dental mouthpiece 7''' shown as a nineteenth embodiment in FIG. 36, the left and right connecting members (only left connecting member 251 is shown in FIG. 36) are provided at positions more toward the posterior teeth than the molar teeth. The connecting members provided at such positions enable no load caused by the bite to be applied to any of the front teeth (central incisors) 3g, 3h, the front teeth (lateral incisors) 3f, 3i, the front teeth (canine teeth) 3e, 3j, the molar teeth 3a to 3d, 3k to 3n as shown in FIG. 1. In other words, the open state can be kept. Such a dental mouthpiece is suitable in the case of aligning the entire teeth.

In the dental mouthpieces including the respective connecting members, the biting state (bite force and biting surfaces) of the upper layer 72 and the lower layer 71 can be kept constant at the position(s) where the vibrating element such as the electric motor 8 is provided. This prevents a change in the vibration transmission mode caused by an unconscious behavior of the user to bite the electric motor 8 or its neighboring part. In other words, this eliminates the need for the user to make an effort to keep the dental mouthpiece open, whereby a good orthodontic effect can be obtained by continuing to apply specified vibration to the teeth to be aligned while reducing burdens on the user.

The inner surface form of the dental mouthpiece according to the present invention is preferably in conformity with the dental cast 1 of the user wearing braces including the orthodontic wire 5 and the brackets 4. The dental mouthpiece reflecting the shape of the braces can be mounted on the teeth wearing the braces, and can be used in combination with the braces.

Figure 37:
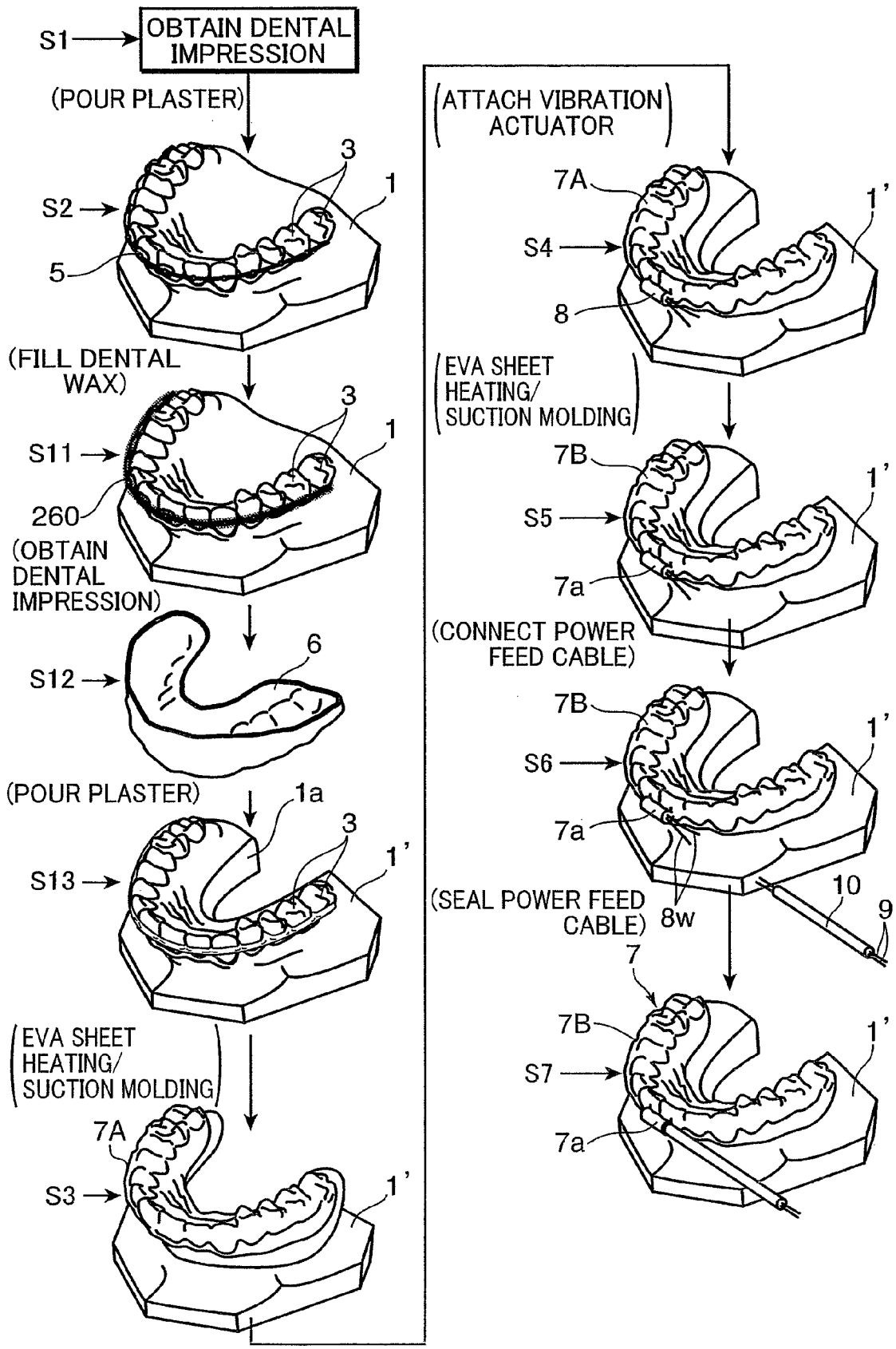
FIG. 37 is a diagram showing a method for producing a dental mouthpiece having an inner surface form in conformity with a user's dental cast having braces mounted thereon.

FIG. 37 is a diagram showing a method for producing such a dental mouthpiece. What should be noted here is that a dental impression is obtained with the brackets 4 and the orthodontic wire 5 mounted on the dental cast 1 (Step S1) and the dental cast 1 is completed (Step S2). Thereafter, dental wax 260 is filled into clearances in parts of the dental cast 1 corresponding to the brackets 4 and the orthodontic wire 5 to thereby eliminate unevenness in Step S11. So-called "paraffin wax" or the like can be used as the dental wax. This material is solid at normal temperature, and is used in liquid state by being heated and molten using an alcohol lamp or the like.

This method reduces burdens on the user as compared to the method according to which the wax is used upon obtaining the dental impression in Step S1, i.e. the method according to which the dental impression is obtained after nontoxic wax or the like that can be washed away with water is filled into clearances of the brackets 4 and the orthodontic wire 5 with the user wearing the brackets 4 and the orthodontic wire 5.

Further, in Step S12, the inner surface form of the impression material 6 obtained using silicon corresponds to an envelope of the outer shape of the braces including the bracket 4 and the orthodontic wire 5. This shape is such a shape capable of avoiding the interference of the unevenness of the braces with the inner surface of the dental mouthpiece to be cast, and a clearance is defined between the inner surface of the impression material and the buccal surface of the teeth 3. Thereafter, plaster is poured into the impression material 6 and taken out after being hardened, whereby a dental cast 1' actually used for the production of the dental mouthpiece 7 is completed. Processes after Step S13 are equivalent to the method shown in FIG. 19.

The inner surface form of the inner layer 7A of the dental mouthpiece 7 thus produced conforms to the dental cast 1 of the user wearing the braces including the orthodontic wire 5 and the brackets 4. In other words, since the inner surface of this inner layer 7 reflects the shape of the braces, the dental mouthpiece 7 is mountable on these braces, which enables the simultaneous use of the dental mouthpiece 7 and the braces.

Further, since the inner surface form of the inner layer 7A corresponds to the shape of the braces including the orthodontic wire 5 and the brackets 4 after having the unevenness reduced and reflects this uneven shape as clearances, the interference of the sharp orthodontic wire 5 and the brackets 4 with the inner layer 7A can be reduced. This prevents the braces from being displaced or coming off and the dental mouthpiece 7 from being damaged when the braces and dental mouthpiece 7 are mounted and detached.

Figure 38:
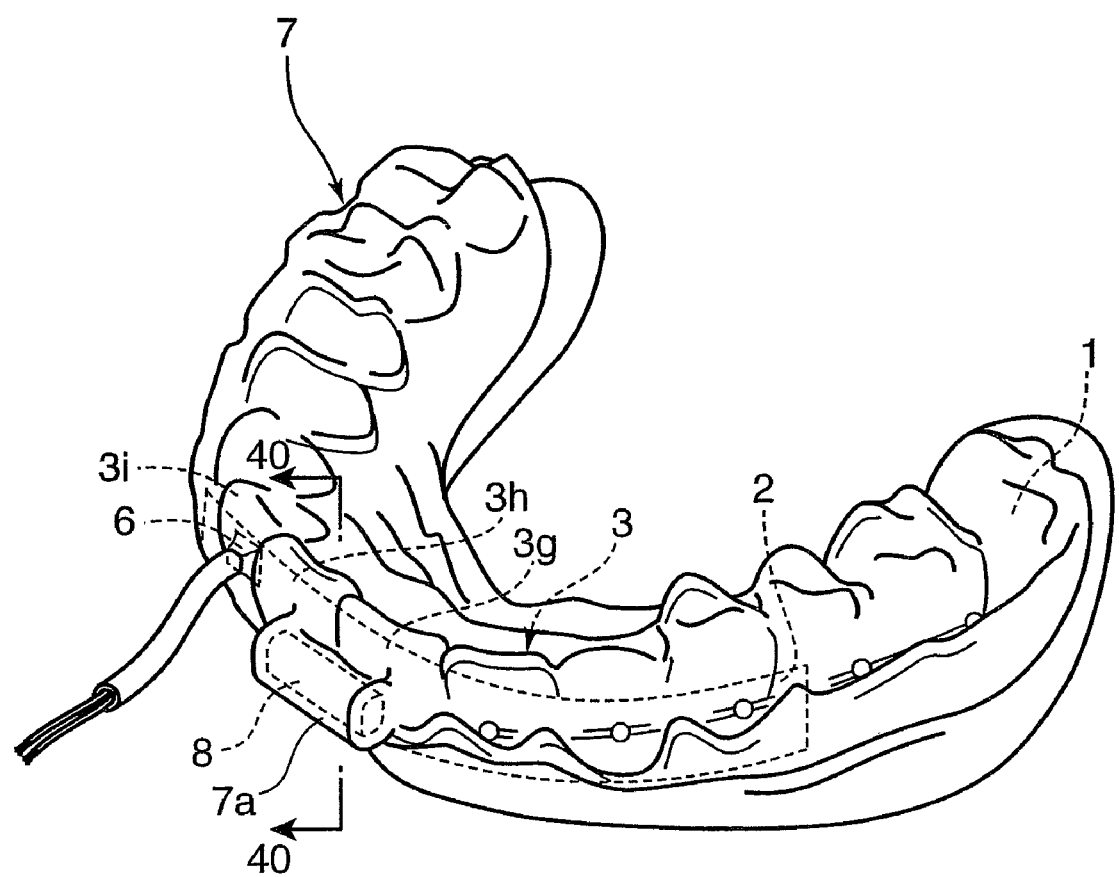
FIG. 38 is a perspective view showing a state where a mouthpiece according to a twentieth embodiment of the invention is mounted on a user's lower dental arch.
Figure 39:
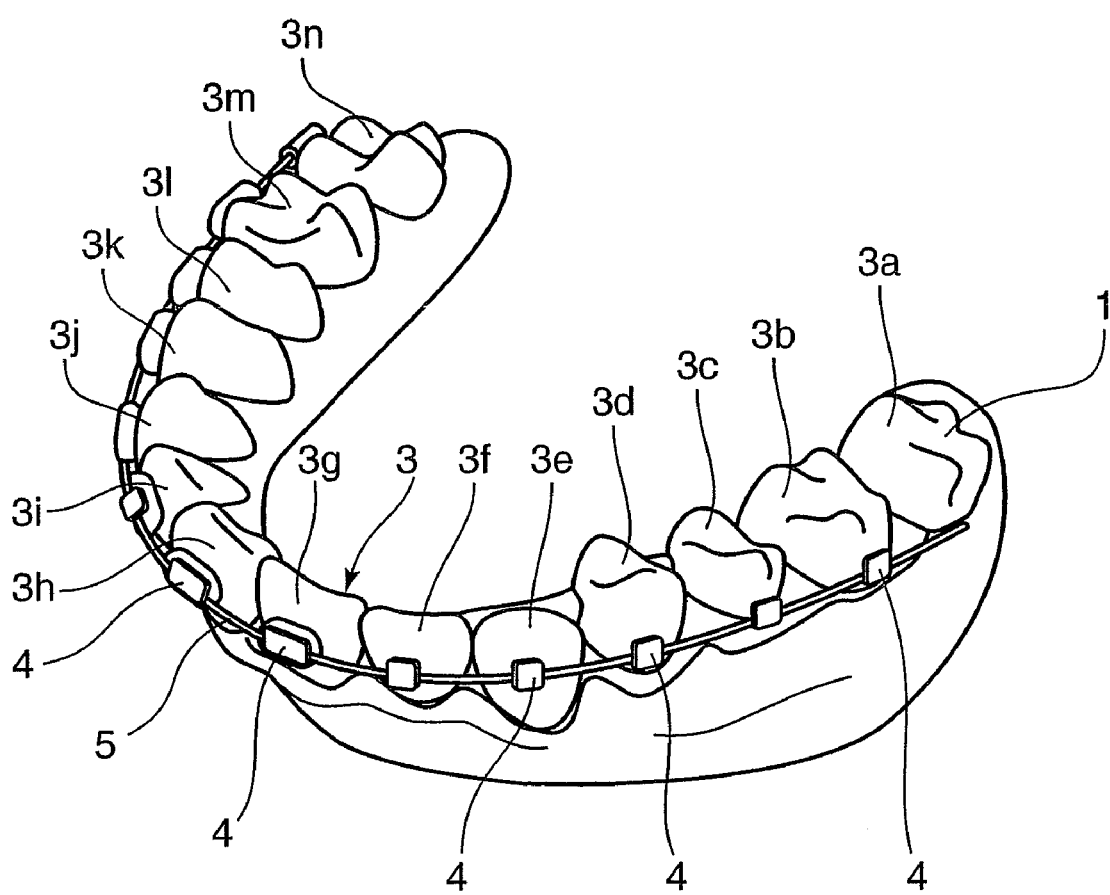
FIG. 39 is a perspective view of a dental cast of the user's lower dental arch.
Figure 40:
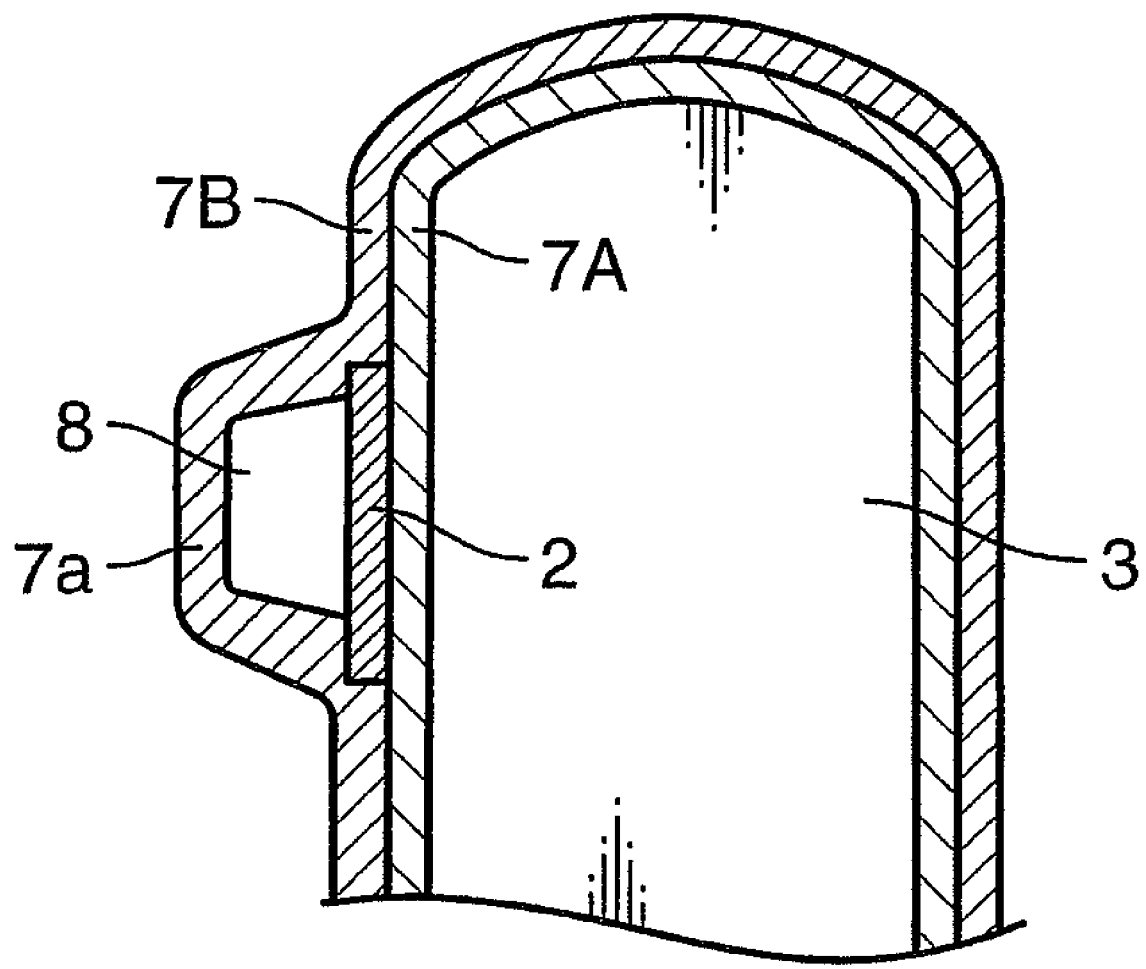
FIG. 40 is a section along the line 40-40 in FIG. 38.

FIG. 38 is a perspective view showing a state where a dental mouthpiece 7 according to a twentieth embodiment of the present invention is mounted on a user's lower dental arch, FIG. 39 is a perspective view of a dental cast 1 of the user's lower dental arch and FIG. 40 is a section along the line 40-40 in FIG. 38.

The orthodontic appliance according to this embodiment is characterized by including a flexible board 2 on which an electric motor 8 as a vibrating element is mounted and incorporating both the electric motor 8 and the flexible board 2 into the dental mouthpiece 7.

Figure 41:
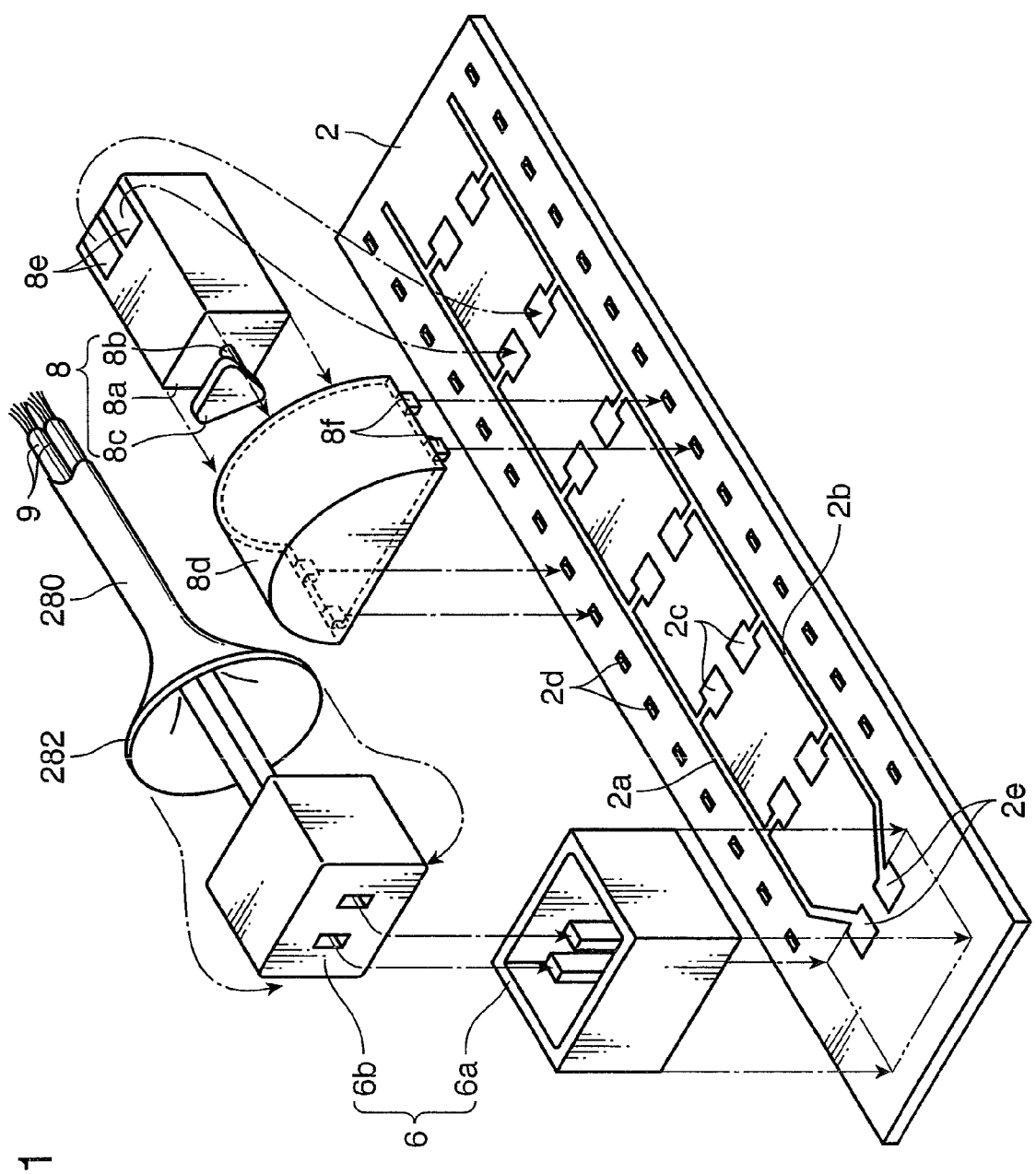
FIG. 41 is an exploded perspective view showing the constructions of a vibration actuator and a flexible board.
Figure 42:
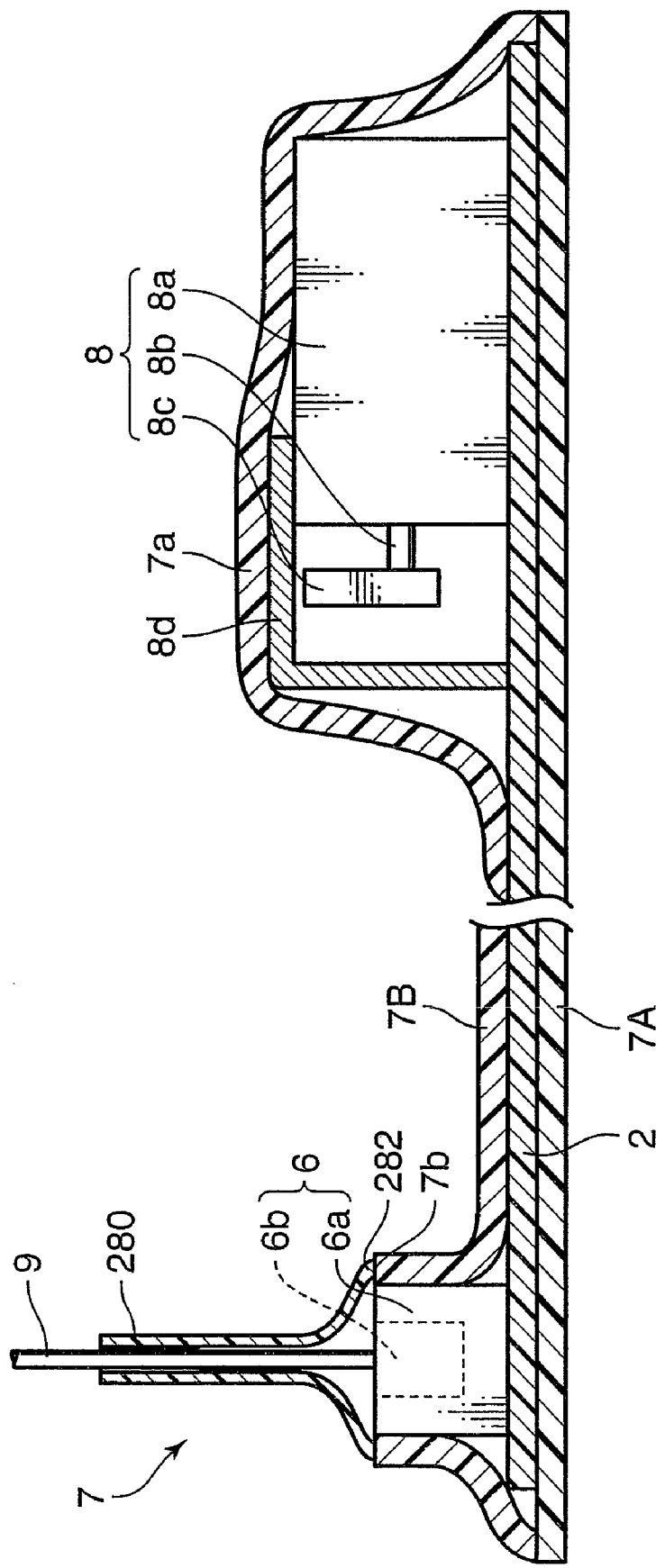
FIG. 42 is a section of the dental mouthpiece according to the twentieth embodiment of the invention, an electric motor built in the dental mouthpiece and a flexible board.

FIG. 41 is an exploded perspective view showing the construction of the electric motor 8 and the flexible board 2, and FIG. 42 is a section of the dental mouthpiece 7 having these built therein.

The electric motor 8 includes a motor main body 8a, a rotary shaft 8b and an eccentric weight 8c mounted on this rotary shaft 8b, and generates mechanical vibration of the rotations of the rotary shaft 8b and the eccentric weight 8c. The electric motor 8 is of the unpacked type having the eccentric weight 8c thereof exposed to the outside. Accordingly, if this electric motor 8 is built in the dental mouthpiece 7 together with the flexible board 2 as it is, the eccentric weight 8c touches inner surface of the dental mouthpiece 7 (e.g. inner surface of a bulge portion 7a for the storage of the vibrating element shown in FIG. 38) and the like, and this touch might hinder the rotation of the eccentric weight 8c.

In order to prevent this inconvenience, a cover member 8d is provided on the flexible board 2. This cover member 8d is made of metal or the like, has a semicylindrical shape with a closed top and covers the eccentric weight 8c in such a manner as to ensure a space for the rotation of the eccentric weight 8c.

The flexible board 2 is in the form of a strip extending in a direction along the teeth 3 as shown in FIG. 38 and has a circuit for introducing an electric power to the motor main body 8a. Specifically, this flexible board 2 is formed with a pair of wiring patterns 2a, 2b extending in the longitudinal direction thereof, and lands 2c used to solder terminals 8e provided on the motor main body 8a are formed at a plurality of positions of the respective wiring patterns 2a, 2b.

Even if this flexible board 2 is formed to have a standardized shape, it can be commonly used for a plurality of users whose teeth to be aligned differ from each other. In other words, even if the teeth to be aligned differ from user to user, the use of the flexible board 2 is enabled by selecting the lands 2c at positions corresponding to the teeth to be aligned (e.g. teeth 3g, 3h to be aligned shown in FIG. 38) as those to which the terminals 8e of the motor main body 8a are soldered. It is also possible to mount a plurality of electric motors 8 on one flexible board and to simultaneously drive them.

The enlargement of the lands 2c of the flexible board 2 strengthens the soldering of the terminals 8e to the lands 2c. This soldering has a remarkably lower probability of breaking than a power feed path formed by a lead wire directly drawn out from the electric motor 8, i.e. forms a power feed path having higher reliability. Further, the use of the flexible board 2 neither damages the dental mouthpiece 7 nor hurts the buccal cavity.

The electric motor 8 may be either a direct-current (DC) motor or an alternating-current (AC) motor. In the former case, the intensity and cycle of the vibration can be made adjustable by feeding a power from a battery via a switch and a variable resistor. The rotating speed of the motor main body 8a, i.e. vibration frequency (number of vibration) of the motor main body 8a is preferably about several Hz to several 100 Hz.

In order to mount the cover member 8d, a plurality of locking holes 2d aligned in the longitudinal direction of the flexible board 2 are perforated at each of the opposite lateral edges of the flexible board 2. On the other hand, projections 8f are formed at the bottom of the cover member 8d and fittable into arbitrary locking holes 2d. By changing the locking holes 2d into which the projections 8f are fitted, the arranged position of the cover member 8d on the flexible board 2 is changed. Accordingly, regardless of to which lands the motor main body 8a is soldered, the cover member 8d can be temporarily fixed at such a position as to cover the eccentric weight 8c by a corresponding selection of the suitable locking holes 2d into which the projections 8f of the cover member 8d are to be fitted. If the mount position of the motor main body 8a on the flexible board 2 is fixed, the lands 2c and the locking holes 2d may be provided only at one position.

The flexible board 2 having the electric motor 8 and the cover member 8d mounted thereon is sealed between the inner layer 7A and the outer layer 7B of the dental mouthpiece 7 in the same manner as described above, and the cover member 8d is fixed to the flexible board 2. Accordingly, even if the electric motor 8 of the unpacked type is used, the normal operation thereof can be guaranteed.

A board side connector 6a for the connection of the flexible board 2 and an external circuit of the dental mouthpiece 7 is provided at one end of the flexible board 2 with respect to longitudinal direction. For example, a two-pin connector produced by Japanese Solderless Terminals Manufacturing Co., Ltd. (JST Mfg. Co., Ltd.) is used as this board side connector 6a. Terminals of this board side connector 6a are soldered to lands 2e formed at ends of the wiring patterns 2a, 2b at one side. Besides the electric motor 8, a control circuit and a power source therefor may be mounted on the flexible board 2. In the case of mounting the control circuit, the board side connector 6a may further include a pin for the transmission of a control signal. Further, in the case of mounting the power source, the connector 6a may be used for the on-off control and power control.

On the other hand, a lead-wire side connector 6b is provided at ends of power feed cables (lead wires) 9 to be drawn out, and is connected with the board side connector 6a. These lead-wire side connector 6b and board side connector 6a form the connector 6 electrically connecting the flexible board 2 and the power feed cables 9.

The use of the connector 6 facilitates a wiring operation between the flexible board 2 and the external circuit. Specifically, as described in detail later, the wiring operation with the outside is performed only by exposing a part of the sealed flexible board 2 corresponding to the connector 6a, connecting the lead-wire side connector 6b with the exposed connector 6a and sealing the exposed part again. This method remarkably simplifies the wiring operation as compared to a method including steps of exposing the wiring patterns 2a, 2b of the sealed flexible board 2 and sealing the exposed parts again after the power feed wires 9 to be drawn out are soldered.

A direction in which the power feed cables 9 are drawn out by this connector 6 is preferably perpendicular to the flexible board 2, i.e. perpendicular to the tooth surface in light of wearing comfort and the connecting operation of the connectors 6a, 6b. Normally, the connector 6 is set at a position corresponding to the front teeth 3g, 3h in view of facilitation to take the lead wires out of the buccal cavity. If the teeth to be aligned are the front teeth 3g, 3h, the position of the connector 6 needs to be changed to a proximate position (e.g. position corresponding to the tooth 3i in FIG. 38). Such a change can be accomplished by displacing the built-in position of the flexible board 2 in the dental mouthpiece 7. An unnecessary part of the flexible board 2 may be built in the dental mouthpiece 7 while being folded or may be cut off.

The power feed cables 9 are covered by an EVA tube 280 made of the same material as the dental mouthpiece 7. The use of this EVA tube 280 enables the drawn-out portions of the power feed cables 9 to the outside to be also sealed airtight. Specifically, the airtight sealing of the drawn-out portions of the power feed cables 9 to the outside of the dental mouthpiece 7 is realized by a method including a step of exposing a part of the board side connector 6 sealed in the dental mouthpiece 7 as described above, a step of connecting the lead-wire side connector 6b with this connector 6a and a step of uniting an end 282 of the EVA tube 280 with a part exposed for the connection of the two connectors 6a, 6b, for example, by melting.

If the connection of the flexible board 2 and the external circuit of the dental mouthpiece 7 is unnecessary, the connector 6 can be omitted. In such a case, no control is necessary from the external circuit to strengthen or weaken the vibration. An exemplary case is such that the power source and the control circuit are also mounted on the flexible board 2 as described above and the electric motor 8 can be turned on and off through the operation of a push-push switch at a thinned part of the outer layer 7B.

If the flexible board 2 is built in the dental mouthpiece 7, the external appearance of the appliance is determined only by the dental mouthpiece 7. Since the power feed cables do not touch the buccal cavity with this appliance, electrical safety can be ensured and an improvement in wearing comfort can be expected. Further, the entire appliance is compact and convenient to carry around, and the practical value thereof is high.

Figure 43:
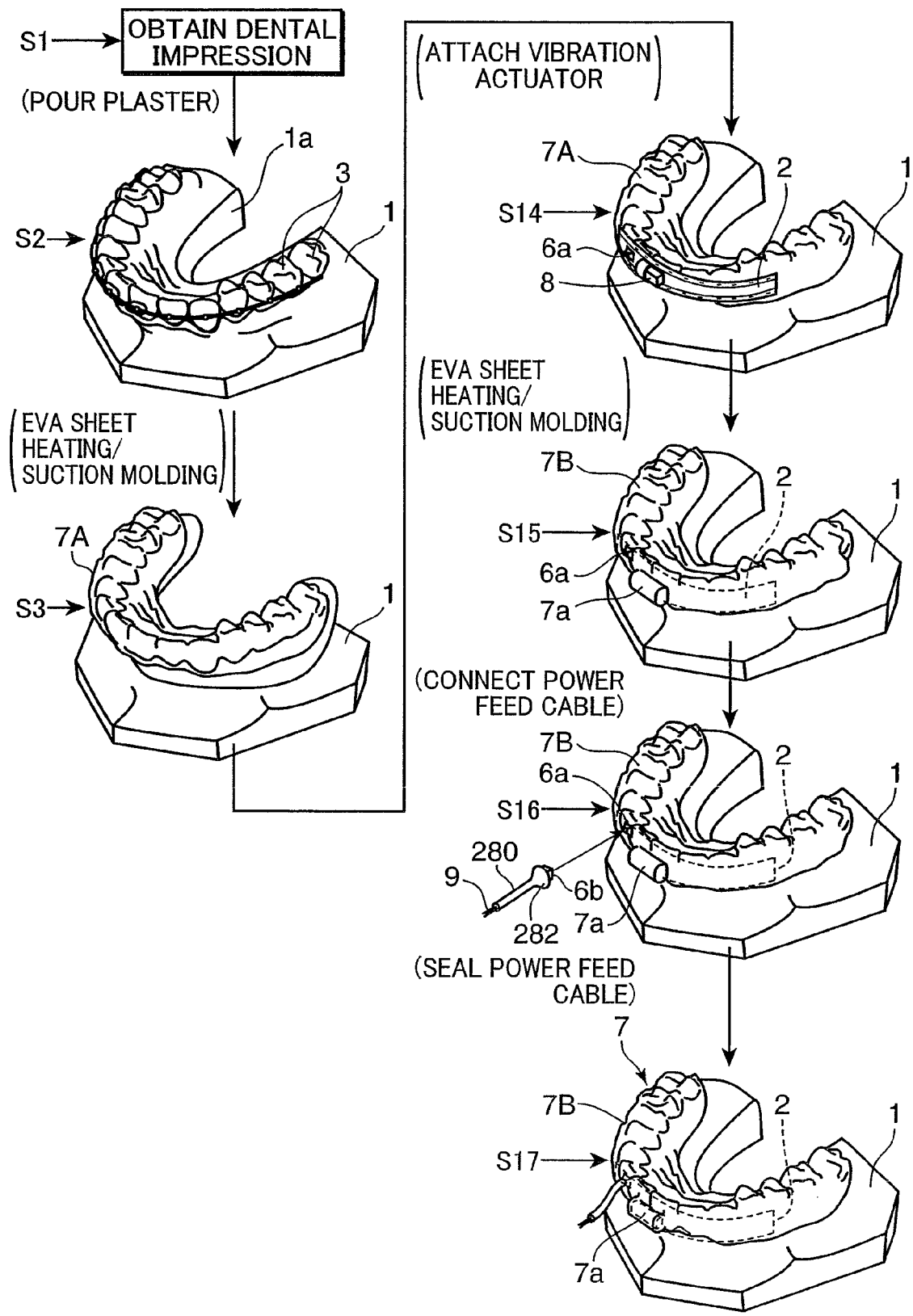
FIG. 43 is a diagram showing a method for producing the dental mouthpiece according to the twentieth embodiment of the invention.

FIG. 43 is a diagram showing a method for producing the dental mouthpiece 7 according to this embodiment. Up to the completion of the inner layer 7A (Step S3), this method is the same as the dental mouthpiece producing method shown in FIG. 19.

After the completion of the inner layer 7A, the flexible board 2 having the electric motor 8 and the connector 6a mounted thereon is attached onto the inner layer 7A while the inner layer 7A is still hot. The material of the dental mouthpiece 7, particularly the EVA, has high viscosity when being molten to such an extent as to be used as a main raw material of so-called hot bond. Accordingly, the inner layer 7A immediately after being cast from the half molten EVA in Step S3 still has heat and exhibits high viscosity until being cooled. The flexible board 2 can be temporarily fixed without particularly using fixing means such as adhesive only by pressing the flexible board 2 against the inner layer 7A utilizing an adhesive force of the material of the inner layer 7A given by the remaining heat of the inner layer 7A.

In Step S15, the outer layer 7B is formed by placing the heated EVA sheet on the inner layer 7A having the flexible board 2 attached thereto as described above as in Step S3 and applying air suction. At this time, the flexible board 2, the electric motor 8 and the connector 6a are sealed airtight between the inner layer 7A and the outer layer 7B.

In Step S16, the EVA forming the outer layer 7B is stripped at a part corresponding to the board side connector 6a in the dental mouthpiece 7 formed in this way, and the lead-wire side connector 6b is connected with the connector 6a. In Step S17, the end portion 282 of the EVA tube 280 mounted on the power feed cables 9 are connected at a suitable position of the outer layer 7B by being locally heated using a drier or the like, and this connected part is sealed airtight. In this way, the dental mouthpiece is completed.

In order to easily insert the power feed cables 9 into the EVA tube 280, the end portion 282 of the tube 280 at an insertion side is preprocessed to be widened as shown in FIGS. 41 and 42. This widening process is realized, for example, by a method including a step of mounting a tubular body having a heat insulating property on the tube 280 and pulling only the end portion 282 from this tubular body, and a step of softening the pulled-out end portion 282 by locally heating it using a drier or the like and inserting a conical body into the end portion 282 to deform the end portion 282 into a shape conforming to the outer circumferential surface of this conic body. The power feed cables 9 connected with the lead-wire side connector 6b are inserted for the connection in Step S16 with the tubular body mounted thereon. This enables complete waterproofing from the dental mouthpiece 7 to the pulled-out portions of the power feed cables 9.

Figure 44:
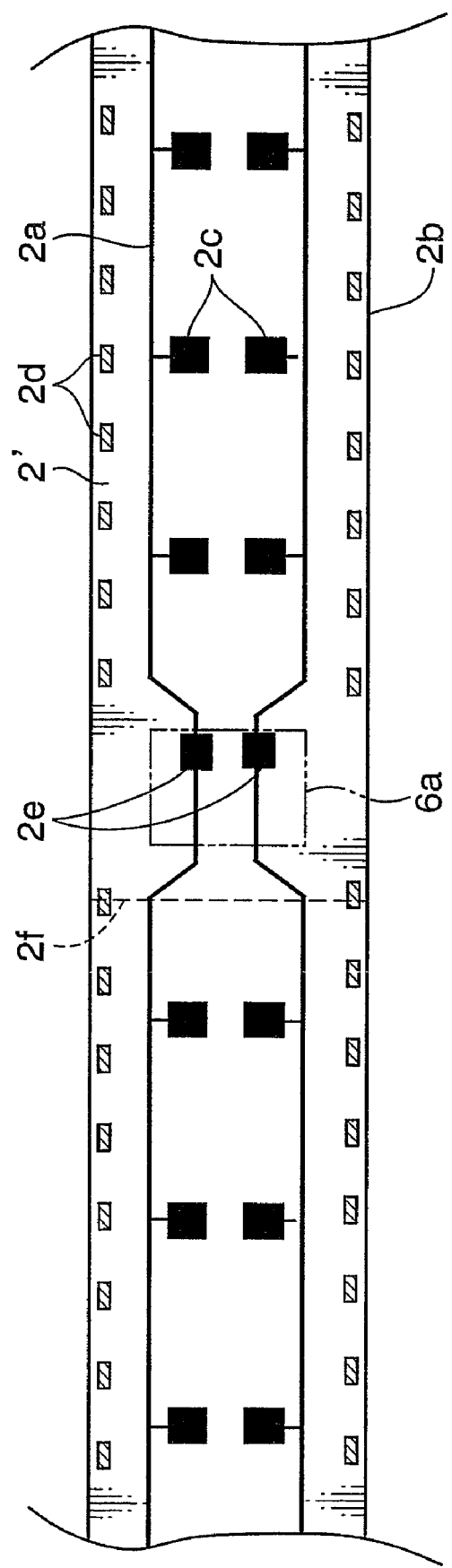
FIG. 44 is a plan view of a flexible board in a dental mouthpiece according to a twenty first embodiment of the invention.

FIG. 44 is a plan view of a flexible board 2' used in an orthodontic appliance according a twenty first embodiment of the present invention. This flexible board 2' is similar to the flexible board 2, and portions of both equivalent to each other are identified by the same reference numerals and are not described.

What should be noted in this flexible board 2' is that the board side connector 6a is mounted at a longitudinal middle position of the flexible board 2' and the flexible board 2' extends toward the opposite sides in directions along the teeth 3 with this connector 6a as a center. Accordingly, this flexible board 2' is suitable for the orthodontic alignment of the molar teeth at the opposite sides since the board side connector 6a is mounted at the position corresponding to the front teeth if the flexible board 2' is used as it is.

This flexible board 2' is characterized by perforation 2f formed at one side of the connector 6a to facilitate the separation of the flexible board 2'. In the flexible board 2' separated at the perforation 2f, the board side connector 6a is located at an end with respect to longitudinal direction. This enables the position where the power feed cables 9 are drawn out from the board side connector 6a to be located at the position of the molar teeth (back side) similar to the aforementioned flexible board 2, and enables the use of the flexible board 2' for the orthodontic alignment of the front teeth.

The opposite ends of the flexible board 2' may be suitably cut off in conformity with the size of a user's mouth. This enables the use of the common flexible board 2' regardless of tooth (teeth) to be aligned and the size of the user's mouth.

According to the present invention, the vibrating element (e.g. electric motor 8) is not necessarily fixed to the lands of the flexible board as described above. For example, the vibrating element may be slidably mounted on the flexible board. This sliding movement enables the positions of the vibrating element on the flexible board to be changed.

As described above, the present invention is directed to an orthodontic appliance for aligning teeth including a tooth to be aligned, the appliance comprising a vibrating element for generating mechanical vibration and applying this vibration to the tooth to be aligned, and a dental mouthpiece having the vibrating element built therein and mountable on the teeth with the vibrating element built therein. Since the vibrating element for generating mechanical vibration (mechanical stimuli) is built in the dental mouthpiece to be mounted on the teeth in this appliance, the vibrating element can efficiently apply vibration to the tooth to be aligned. Further, the storage of the vibrating element in the dental mouthpiece enables a treatment to be easily and safely continued at any desired time, for example, at home without going to a dental clinic.

It is preferable that the dental mouthpiece includes an inner layer and an outer layer to be superimposed on the outer side of the inner layer; and that a vibrating element storing portion for storing the vibrating element is formed between the inner layer and the outer layer. This construction facilitates the storage of the vibrating element into the dental mouthpiece. Since the mechanical vibration of the vibrating element is transmitted to the tooth to be aligned via the superimposed part of the dental mouthpiece having an overlaid structure, this vibration can be more softly transmitted as compared to the case where mechanical vibration is directly transmitted to the tooth to be aligned. Further, the dental mouthpiece is water-washable and, thus, hygienic if the vibrating element is hermetically stored in the dental mouthpiece.

Specifically, it is preferable that the outer layer includes an outward projecting bulge portion; and that the vibrating element is stored between the inner side of the bulge portion and the outer side of the inner layer. This structure enables the storage of the vibrating element into the dental mouthpiece without enlarging the entire dental mouthpiece.

The vibrating element storing portion is more preferably formed at a part of the dental mouthpiece corresponding to the tooth to be aligned.

For example, a motor is preferably used as the vibrating element. In order to make this vibrating element more inexpensive, the motor preferably includes an eccentric rotary portion rotatable about a specified axis and having a center of gravity at a position deviated from this axis. For example, this eccentric rotary portion preferably includes a rotary shaft and an eccentric weight mounted on this rotary shaft such that the center of gravity thereof is deviated from the center of the rotary shaft and adapted to generate mechanical vibration by rotating together with the rotary shaft.

The vibrating element may be a linear motor having a moving element that reciprocally vibrates.

If the appliance according to the present invention further comprises a battery as a direct-current power source and the motor is a DC motor driven by the direct-current power source and electrically connected with the battery, a treatment can be made, for example, outdoors.

Further, if the battery is stored in the vibrating element storing portion together with the motor, the wearing comfort becomes improved because a cable does not expose out of the mouth, and carrying of the appliance is more convenient.

The vibrating element is more preferably built in the dental mouthpiece in such an orientation that the direction of the vibration generated by the vibrating element is substantially normal to the teeth. This can improve vibration transmission efficiency.

The vibrating element may be a permanent magnet for generating mechanical vibration in response to a magnetic field generated by magnetic field generating means arranged outside the dental mouthpiece. The use of this permanent magnet makes the entire appliance smaller.

The dental mouthpiece may be so shaped as to be mountable on braces mounted on the teeth to align the tooth to be aligned or may be so shaped as to apply an aligning force to the tooth to be aligned.

The former dental mouthpiece preferably has an inner surface form conforming to the dental cast of the user wearing the braces. Since the inner surface form of this dental mouthpiece reflects the shape of the braces, the dental mouthpiece can be mounted on the braces. This realizes the simultaneous use of the braces and the dental mouthpiece.

The inner surface form of such a dental mouthpiece is preferably a shape corresponding to an envelope of the outer shape of the braces and capable of avoiding the interference of the unevenness of the braces with the inner surface of the dental mouthpiece. Such a shape has the following advantages.

Stimuli from the vibrating element to the teeth are alleviated to prevent the gums to be hurt by the stimuli.

Wearing comfort is improved.

The production of the dental mouthpiece is facilitated.

Damages of the gums by the edges and the like of the dental mouthpiece can be prevented.

The dental mouthpiece may be so shaped as to be mountable on the entire teeth or may be so shaped as to be mountable on a part of the teeth. The former shape enables the positional relationship between the tooth to be aligned and the vibrating element to be more precisely set. The latter shape can make the dental mouthpiece smaller.

Further, it is more preferable that the dental mouthpiece includes a dividing portion at a part thereof except at the one corresponding to the tooth to be aligned; and that this divided portion suppresses the transmission of mechanical vibration so that the mechanical vibration generated by the vibrating element acts restrictedly on the part including the tooth to be aligned.

This construction enables the vibration to be restrictedly applied to the tooth to be aligned.

The dental mouthpiece including the dividing portion preferably includes, for example, any one of the following constructions in order to facilitate the production thereof.

a) The dividing portion of the dental mouthpiece is a cutout portion formed by cutting out either a tooth root portion or a tooth crown portion of the dental mouthpiece except at the tooth to be aligned, and the other part integrally connect parts of the dental mouthpiece before and after the cutout portion.

b) The dividing portion of the dental mouthpiece is a slit portion formed in a part of the dental mouthpiece except at the tooth to be aligned, and parts of the dental mouthpiece before and after this slit portion are connected to each other.

c) The dividing portion of the dental mouthpiece is a cut portion formed by cutting a part of the dental mouthpiece except at the tooth to be aligned, and parts of the dental mouthpiece before and after this cut portion are connected via a member separate from the one forming the cut portion.

d) The dividing portion of the dental mouthpiece is a cutoff portion formed by cutting off a part of the dental mouthpiece except at the tooth to be aligned, and this cutoff portion is defined in such a position that the dental mouthpiece has a shape fittable for only the tooth to be aligned.

e) The dividing portion of the dental mouthpiece is a cutout portion formed by cutting out either a tooth root portion or a tooth crown portion of the dental mouthpiece except at the tooth to be aligned, and parts of the dental mouthpiece before and after the cutout portion are integrally connected by the remaining part of the dental mouthpiece.

It is more preferable that the dental mouthpiece includes a storage space for storing the vibrating element inside; and that this storage space has such a shape as to provide the vibrating element with a play permitting the vibrating element itself to move in the storage space.

The play permits the vibrating element itself to move in the storage space by a vibration load generated by the vibrating element. The vibrating element permitted to make such movements collides with the inner surface of the dental mouthpiece enclosing the storage space. Loads caused by this collision can increase the vibration applied to the teeth of the user wearing the dental mouthpiece. This enables stimuli sufficient to promote the orthodontic effect to be applied to the tooth to be aligned while using a vibrating element that is small-sized and lightweight and generates a small vibration load.

The storage space is particularly preferably shaped such that a clearance is formed in the storage space in a direction corresponding to an aligning direction of the tooth to be aligned. Such a shape enhances the directivity of the vibration to be applied to the tooth to be aligned. For example, even if only the vibrating element having a low vibration directivity (e.g. inexpensive and small-sized rotary motor or vibration motor) can be used because of cost and size, a vibration load having high directivity can be applied to the teeth.

The dental mouthpiece preferably comprises an upper layer to be mounted on an upper teeth and a lower layer to be mounted on a lower teeth, the vibrating element being built in at least one of the upper and lower layers; and a connecting member connecting the upper layer and the lower layer at a position distanced from the tooth to be aligned.

The connecting member keeps the biting state (bite force and biting surfaces) of the upper and lower layers constant at the position where the vibrating element is built in, thereby preventing the user from unconsciously biting the vibrating means and its neighboring part and the bite from changing a way of transmitting the vibration. As a result, a desired orthodontic effect can be obtained by continuing to apply desired vibration to the tooth to be aligned while reducing burdens by eliminating the need for the user to make an effort to keep the dental mouthpiece open.

The position of the connecting member is not limited. For example, the dental mouthpiece having the connecting member disposed at a position corresponding to the front teeth is suitable for the dental alignment of the molar teeth since it can ensure a constant biting state at a part corresponding to the molar teeth by preventing the application of loads given by the bite to this part. Further, the dental mouthpiece having the connecting member disposed at a position corresponding to the molar teeth is suitable for the dental alignment of the front teeth since it can ensure a constant biting state at a part corresponding to the front teeth by preventing the application of loads given by the bite to this part. Furthermore, the dental mouthpiece having the connecting member disposed at a position more toward the back side than the molar teeth is suitable for the dental alignment of the entire teeth since it can be kept open by preventing the application of loads given by the bite to parts corresponding to both the front teeth and the molar teeth.

It is preferable that the orthodontic appliance according to the present invention further comprises a flexible board on which the vibrating element is to be mounted; and that this flexible board includes a circuit for introducing power to the vibrating element and is built in the dental mouthpiece together with the vibrating element.

The flexible board forms a power feeding path for introducing power to the vibrating element mounted thereon. This power feeding path has a fairly lower likelihood of breaking as compared to, for example, a power feeding path formed by drawing a lead wire out from the vibrating element. Further, the use of the flexible board neither damages the dental mouthpiece nor hurts the buccal cavity. Beside the vibrating element, it is also possible to mount a control circuit and a power source for the vibrating element on the flexible board.

Further, if a board side connector for the external connection is mounted on the flexible board, a wiring operation for connecting the vibrating element and an external circuit of the dental mouthpiece can be facilitated. This wiring operation is carried out, for example, by a method comprising a step of exposing a part of the sealed flexible board corresponding to the board side connector from the dental mouthpiece, a step of connecting a lead-wire side connector attached to a lead wire to be drawn out with the exposed board side connector, and a step of sealing the exposed part again. This method remarkably simplifies the wiring operation as compared to a method including a step of exposing a wiring pattern of the sealed flexible board from the dental mouthpiece, a step of soldering a lead wire to be drawn out to the wiring pattern, and a step of sealing the exposed part again.

Further, with an appliance comprising a lead wire drawn out from the board side connector and a tube made of the same material as the dental mouthpiece and adapted to cover the lead wire, a part where the lead wire is drawn out from the dental mouthpiece can also be sealed utilizing the tube. Specifically, a part of the sealed flexible board corresponding to the board side connector is exposed from the dental mouthpiece, and the lead-wire side connector connected with the lead wire to be drawn out is connected with this board side connector. Thereafter, a drawn-out portion is sealed airtight by performing a step of uniting an end of the tube with the exposed part for the connection of the connectors, for example, by melting this end of the tube.

More preferably, the flexible board is so built in the dental mouthpiece as to extend in the direction of the teeth and formed with a wiring pattern extending in the longitudinal direction thereof, a plurality of lands used to solder the vibrating element being formed at a plurality of positions of the wiring pattern.

With this flexible board, even if the shape of the flexible board is standardized beforehand, the vibrating element can be arranged at an optimal position by selecting the land to which the vibrating element should be soldered from those provided on the flexible board. This enables the vibrating element to be mounted on the flexible board at a most suitable position for the tooth to be aligned even if the tooth to be aligned differs from user to user, with the result that the versatility of the flexible board can be improved and the cost of the appliance can be reduced. It is also possible to mount a plurality of vibrating elements on one flexible board and to simultaneously drive them.

If the vibrating element includes a motor having an output shaft and an eccentric weight mounted on the output shaft, a cover member for covering the eccentric weight is more preferably so fixed to the flexible board as to define a space necessary for the rotation of the eccentric weight. This cover member effectively suppresses the hindrance of the eccentric weight to the satisfactory rotation of its own by the contact of the eccentric weight with the inner surface of the dental mouthpiece.

The present invention is also directed to a method for producing an orthodontic appliance comprising a vibrating element for generating mechanical vibration and applying the vibration to a tooth to be aligned of a user, and a dental mouthpiece having the vibrating element built therein and mountable on teeth of the user including the tooth to be aligned with the vibrating element built therein, the orthodontic appliance promoting dental alignment by transmitting the mechanical vibration to the tooth to be aligned, the method comprising: a first step of forming an inner layer constituting an inner part of the dental mouthpiece by placing a sheet member having a heat softening property on a dental cast of the user with the sheet member heated to be softened and closely attaching the sheet member onto the dental cast; a second step of mounting the vibrating element on the inner layer; and a third step of setting the inner layer having the vibrating element mounted thereon on the dental cast of the user, placing a sheet member having a heat softening property on the inner layer with the sheet member heated to be softened, and closely attaching the softened sheet member to the inner layer, thereby forming an outer layer constituting an outer part of the dental mouthpiece and sealing the vibrating element airtight between the outer layer and the inner layer.

According to this method, the dental mouthpiece having the inner and outer layers can be efficiently produced. Specifically, one dental impression is sufficient to form the outer layer, thereby reducing the number of operation steps. According to this method, instead of reheating the hardened inner layer and outer layer and bonding those to each other, the sheet member of the inner layer and that of the outer layer half molten by the heat of the mounted outer layer and the heat transferred from the outer layer to the inner layer are naturally united. Therefore, a dental mouthpiece having high airtightness and high quality can be formed.

In the second step, the vibrating element can be attached to the inner layer utilizing an adhering force of the material of the inner layer given by the remaining heat of the inner layer. This method obviates the need for another fixing means such as adhesive or enables the vibrating element to be simply temporarily fixed to the inner layer while reducing a used amount of another fixing means.

In the first step, a sheet member made of a resin whose softening temperature is lower than the heat resistant temperature of the vibrating element is preferably used as the sheet member for forming the inner layer.

This construction enables the sheet member for forming the inner layer to be placed on the vibrating element while avoiding the trouble of the vibrating element due to a high temperature.

What is claimed is:

1. An orthodontic appliance for aligning teeth including a tooth to be aligned, the appliance comprising:
   a vibrating element that generates mechanical vibration and applies the vibration to the tooth to be aligned, the vibrating element including a driven element and a driver that drives the driven element to generate the mechanical vibration; and
   a dental mouthpiece including an inner layer and an outer layer superimposed on an outer side of the inner layer, the dental mouthpiece having the vibrating element, including both of the driven element and the driver encapsulated within the dental mouthpiece and mountable on the teeth with the vibrating element encapsulated therein, wherein:
   the inner layer has a shape conforming to the teeth to which the mouthpiece is attached,
   the vibrating element is provided on an outer surface of the inner layer, and
   the outer layer has a shape conforming to the shape of the inner layer and an inner surface joined, in an airtight manner, to the outer surface of the inner layer, a portion of the outer layer including a bulge portion that projects outward so as to have a shape conforming to a shape of the vibrating element, and the vibrating element is received between an inner surface of the bulge portion and the outer surface of the inner layer.

2. An orthodontic appliance according to claim 1, wherein the vibrating element storing portion is formed at a part of the dental mouthpiece corresponding to the tooth to be aligned.

3. An orthodontic appliance according to claim 1, wherein the driver is a motor that drives the driven element.

4. An orthodontic appliance according to claim 3, wherein the driver is connected to the driven element, and the driven element includes an eccentric rotary portion rotatable about a predetermined axis and having a center of gravity at a position deviated from the axis.

5. An orthodontic appliance according to claim 4, wherein the eccentric rotary portion includes a rotary shaft and an eccentric weight mounted on the rotary shaft such that the center of gravity thereof is deviated from the center of the rotary shaft and is configured to generate mechanical vibration by rotation together with the rotary shaft.

6. An orthodontic appliance according to claim 3, wherein the driver is a linear motor connected to the driven element, and the driven element comprises a moving element that reciprocally vibrates.

7. An orthodontic appliance according to claim 3, further comprising a battery as a direct-current power source, wherein the motor is a DC motor driven by the direct-current power source and electrically connected with the battery.

8. An orthodontic appliance according to claim 7, wherein the battery is stored in the dental mouthpiece, together with the DC motor.

9. An orthodontic appliance according to claim 3, wherein the motor is built within the dental mouthpiece in such an orientation that the direction of vibration generated by the motor and driven element is substantially normal to the teeth.

10. An orthodontic appliance according to claim 1, wherein the dental mouthpiece is so shaped as to be mountable on braces mounted on the teeth in such a manner as to align the tooth to be aligned.

11. An orthodontic appliance according to claim 10, wherein the dental mouthpiece has an inner surface form conforming to a dental cast of a user wearing the braces.

12. An orthodontic appliance according to claim 11, wherein the inner surface form of the dental mouthpiece is a shape corresponding to an envelope of the outer shape of the braces and capable of avoiding the interference of the unevenness of the braces with the inner surface of the dental mouthpiece.

13. An orthodontic appliance according to claim 1, wherein the dental mouthpiece is so shaped as to be mountable on the entire teeth.

14. An orthodontic appliance according to claim 1, wherein the dental mouthpiece is so shaped as to be mountable on a part of the teeth.

15. An orthodontic appliance according to claim 1, wherein the dental mouthpiece includes a dividing portion at a part thereof except the one corresponding to the tooth to be aligned; and the dividing portion suppresses the transmission of the mechanical vibration generated by the vibrating element so that the mechanical vibration is restricting to acting on the part including the tooth to be aligned.

16. An orthodontic appliance according to claim 15, wherein the dividing portion of the dental mouthpiece is a cutout portion formed by cutting out either one of a tooth root portion and a tooth crown portion of the dental mouthpiece except at the tooth to be aligned; and the other part integrally connects parts of the dental mouthpiece on each side of the cutout portion.

17. An orthodontic appliance according to claim 15, wherein the dividing portion of the dental mouthpiece is a slit portion formed in a part of the dental mouthpiece except at the tooth to be aligned; and parts of the dental mouthpiece on each side of the slit portion are connected to each other.

18. An orthodontic appliance according to claim 15, wherein the dividing portion of the dental mouthpiece is a cut portion formed by cutting a part of the dental mouthpiece except at the tooth to be aligned, and parts of the dental mouthpiece on each side of this cut portion are connected via a member separate from the one forming the cut portion.

19. An orthodontic appliance according to claim 15, wherein the dividing portion of the dental mouthpiece is a cutoff portion formed by cutting off a part of the dental mouthpiece except at the tooth to be aligned, and the cutoff portion is defined in such a position that the dental mouthpiece has a shape fittable for only the tooth to be aligned.

20. An orthodontic appliance according to claim 1, wherein the dental mouthpiece includes a storage space for storing the vibrating element inside; and the storage space has such a shape as to provide the vibrating element with a play permitting the vibrating element itself to move in the storage space.

21. An orthodontic appliance according to claim 20, wherein the storage space is shaped such that a clearance is formed in the storage space in a direction corresponding to an aligning direction of the tooth to be aligned.

22. An orthodontic appliance according to claim 1, wherein the dental mouthpiece includes an upper layer to be mounted on upper teeth and a lower layer to be mounted on lower teeth, the vibrating element being built in at least one of the upper and lower layers; and a connecting member connecting the upper layer and the lower layer at a position spaced from the tooth to be aligned.

23. An orthodontic appliance according to claim 1, further comprising a flexible board on which the vibrating element is to be mounted, wherein the flexible board includes a circuit for introducing power to the vibrating element and is built in the dental mouthpiece together with the vibrating element.

24. An orthodontic appliance according to claim 23, wherein a board side connector for connecting the flexible board and an external circuit of the dental mouthpiece is mounted on the flexible board.

25. An orthodontic appliance according to claim 24, further comprising a lead wire drawn out from the board side connector mounted on the flexible board; and a tube made of the same material as the dental mouthpiece and adapted to cover the lead wire.

26. An orthodontic appliance according to claim 23, wherein the flexible board is so built in the dental mouthpiece as to extend in the direction of the teeth and formed with a wiring pattern extending in the longitudinal direction thereof, a plurality of lands used to solder the vibrating element being formed at a plurality of positions of the wiring pattern.

27. An orthodontic appliance according to claim 23, wherein the driver includes a motor having an output shaft and the driven element includes an eccentric weight mounted on the output shaft; and a cover member for covering the eccentric weight is so fixed to the flexible board as to define a space necessary for the rotation of the eccentric weight.

* * * * *